(12) United States Patent
Bough et al.

(10) Patent No.: US 11,524,116 B2
(45) Date of Patent: Dec. 13, 2022

(54) ASSEMBLY FOR A DRUG DELIVERY DEVICE AND DRUG DELIVERY DEVICE

(71) Applicant: SANOFI, Paris (FR)

(72) Inventors: Joshua Bough, Cambridge (GB); Rosemary Burnell, Cambridge (GB)

(73) Assignee: Sanofi, Paris (FR)

(*) Notice: Subject to any disclaimer, the term of this patent is extended or adjusted under 35 U.S.C. 154(b) by 298 days.

(21) Appl. No.: 16/619,629

(22) PCT Filed: Jun. 8, 2018

(86) PCT No.: PCT/EP2018/065156
§ 371 (c)(1),
(2) Date: Dec. 5, 2019

(87) PCT Pub. No.: WO2018/224648
PCT Pub. Date: Dec. 13, 2018

(65) Prior Publication Data
US 2020/0155767 A1 May 21, 2020

(30) Foreign Application Priority Data
Jun. 9, 2017 (EP) .................................... 17305698

(51) Int. Cl.
*A61M 5/315* (2006.01)
(52) U.S. Cl.
CPC ...... *A61M 5/31541* (2013.01); *A61M 5/3158* (2013.01); *A61M 5/31528* (2013.01);
(Continued)
(58) Field of Classification Search
CPC .......... A61M 5/31541; A61M 5/31528; A61M 5/31553; A61M 5/3158; A61M 5/31593; A61M 2005/3154
See application file for complete search history.

(56) References Cited

U.S. PATENT DOCUMENTS

| 2016/0045666 A1* | 2/2016 | Wilden | A61M 5/31553 604/207 |
| 2017/0173268 A1* | 6/2017 | Enggaard | A61M 5/31536 |
| 2017/0209651 A1* | 7/2017 | Moser | A61M 5/31585 |

FOREIGN PATENT DOCUMENTS

| CN | 206120870 | 4/2017 |
| EP | 0615762 | 9/1994 |

(Continued)

OTHER PUBLICATIONS

International Preliminary Report on Patentability in Application No. PCT/EP2018/065156, dated Dec. 10, 2019, 8 pages.
(Continued)

*Primary Examiner* — Dung T Ulsh
(74) *Attorney, Agent, or Firm* — Fish & Richardson P.C.

(57) ABSTRACT

A drug delivery device includes a housing and a movable member, which is arranged to be rotatable in an incrementing direction and a decrementing direction, the movable member being operatively coupled to an energy storage member and biased to rotate into the decrementing direction by energy stored or storable in the energy storage member. Rotation of the movable member in the incrementing direction increases the energy stored in the energy storage member. The drug delivery device also includes a locking system including a locking feature, a block feature, and a release member, wherein the locking feature is arranged to cooperate with the block feature to form a releasable locking interface configured such that, when the releasable locking interface is established, rotational movement of the movable member relative to the housing is blocked in the decrementing direction, and when the releasable locking interface is released, the movable member is rotatable in the decrementing direction.

20 Claims, 18 Drawing Sheets

(52) U.S. Cl.
CPC .... *A61M 5/31553* (2013.01); *A61M 5/31593* (2013.01); *A61M 2005/3154* (2013.01)

(56) References Cited

FOREIGN PATENT DOCUMENTS

| | | |
|---|---|---|
| EP | 3006068 | 4/2016 |
| JP | H06-296691 | 10/1994 |
| JP | 2017-505177 | 2/2017 |
| WO | WO 2014/166905 | 10/2014 |
| WO | WO 2014/166920 | 10/2014 |
| WO | WO 2016/001300 | 1/2016 |
| WO | WO 2016/012278 | 1/2016 |
| WO | WO 2016/055628 | 4/2016 |

OTHER PUBLICATIONS

International Search Report and Written Opinion in Application No. PCT/EP2018/065156, dated Jul. 25, 2018, 12 pages.

\* cited by examiner

A

B

ASSEMBLY FOR A DRUG DELIVERY DEVICE AND DRUG DELIVERY DEVICE

CROSS-REFERENCE TO RELATED APPLICATIONS

The present application is a national stage entry of International Patent Application No. PCT/EP2018/065156, filed on Jun. 8, 2018, and claims priority to Application No. EP 17305698.7, filed on Jun. 9, 2017, the disclosures of which are incorporated herein by reference.

TECHNICAL FIELD

The present disclosure relates to an assembly, e.g., for a drug delivery device, and to a drug delivery device.

BACKGROUND

Drug delivery devices do have a widespread use, such as for self-administration by a user which has not undergone a formal medical training. Accordingly, the devices have to function reliably and accurately as, otherwise, the user's health is put to serious risk.

SUMMARY

The present disclosure provides a novel or improved assembly, such as for a drug delivery device. Particularly, an improved drug delivery device is provided. This is achieved by the subject matter defined in the independent claims, but not necessarily only by the claimed subject matter as the present disclosure may contain further advantageous features and combinations thereof. Advantageous embodiments and refinements are subject of the dependent claims and disclosed throughout the specification.

An aspect of the present disclosure relates to an assembly, particularly an assembly for a drug delivery device. Another aspect relates to a drug delivery device comprising the assembly or elements of the assembly. Accordingly, features described below with respect to the assembly do apply as well for the drug delivery device and vice versa. Further, features described in conjunction with different embodiments or aspects may be combined with one another and also with arbitrarily selected features from a claim or all features of one claim or a plurality of claims.

In an embodiment, the drug delivery device comprises, preferably in addition to the assembly, a reservoir, particularly a cartridge, which comprises a, preferably liquid, drug or drug formulation. The reservoir may hold a plurality of doses of the drug. The size of the dose to be delivered by the drug delivery device may be set by the user. The size of the dose may be varied by the user and is, preferably, not exclusively defined by the design of the mechanism of the drug delivery device as in so-called fixed dose devices. Consequently, the user may influence how much drug is dispensed per dose. The drug delivery device may be a pen-type device.

In particular, the drug delivery device may be a drug delivery device for separating and delivering a number of pre-settable doses, preferably multiple pre-settable doses, of a liquid drug formulation from the reservoir. The reservoir is preferably an undivided reservoir. Particularly, in an undivided reservoir, the drug formulation is expediently not provided in a way pre-packaged into several doses or units but rather as a continuous volume in a single cavity within the reservoir. From the continuous volume the doses can be separated off during or for dose delivery.

The drug delivery device and/or a component of the assembly or the drug delivery device may have a proximal end and a distal end. In this disclosure, "distal end" is used to designate an end, which is or is to be arranged closest to the dispensing end of the device, whereas "proximal end" is used to designate an end, which is or is to be arranged furthest away from the distal end of the drug delivery device. The term "distal direction" is used to indicate a, particularly axial, direction towards the distal end or away from the proximal end, and the term "proximal direction" is used to indicate a, particularly axial, direction away from the distal end or towards the proximal end. The distal direction and the proximal direction may be used to designate axial directions and, particularly collinear, axial directions with opposite orientations.

In an embodiment, the assembly comprises a housing. The housing may have a tubular shape and may be designed to house and protect further components of the assembly or the drug delivery device. The housing may be designed to be connected—either releasably, e.g. for a reusable device, or permanently, e.g. for a disposable device—to a reservoir or cartridge holder, which is designed to receive and retain the reservoir or cartridge with the drug. The housing may further be arranged to protect and/or house the further elements, members or components of the assembly, which are described in more detail below.

In an embodiment, the assembly comprises a movable member. The movable member may be arranged to be rotatable in two opposite rotational or angular directions with respect to the housing. Particularly, the movable member is rotatable in a first rotational or angular direction and in a second rotational or angular direction with respect to the housing, where the first direction may in the following be referred to as incrementing direction and the second direction may in the following be referred to as decrementing direction. The movable member may be mounted rotatably with respect to the housing, where axial displacement of the movable member with respect to the housing may be restricted or even prevented. The incrementing direction of rotation may be that direction, which is used for setting a desired operation condition, e.g. a dose of a desired size, for the assembly. The decrementing direction may be a correction direction, which is used to correct the operating condition, in case the mechanism has been incremented too far, e.g. to decrease the size of the dose.

In an embodiment, the assembly comprises a locking system. The locking system may be designed to releasably lock the movable member against rotation in a particular rotational direction relative to the housing, such as in the decrementing direction. This ensures that, before a rotation of the movable member in the decrementing direction is possible, the releasable lock has to be released, such that the probability that the assembly is decremented accidentally is reduced considerably.

In an embodiment, the assembly comprises a locking feature, a release member and/or a block feature. The locking system may comprise the respective feature or member.

In an embodiment, the locking feature is arranged to cooperate with the block feature to form or establish a releasable locking interface. The locking feature may be arranged to engage or abut the block feature to form or establish the releasable locking interface. The releasable locking interface is expediently configured such that, when the releasable locking interface is established, rotational movement of the movable member relative to the housing is blocked in the decrementing direction, preferably only in the decrementing direction. In this case, "blocking" expediently means that rotation in the decrementing direction is not allowed at all. When the interface is established, rotation of the movable member relative to the housing in the incrementing direction may be allowed. Thus, the assembly may be incremented when the interface is established. When the releasable locking interface is released, the movable member is preferably rotatable in the decrementing direction, e.g. at least in a limited way, preferably only in a limited way or in a non-limited way. Consequently, by releasing the locking interface, the mechanism or assembly can be decremented, i.e. the movable member may rotate in the decrementing direction.

In an embodiment, the locking feature and the block feature are provided on different components or members.

In an embodiment, the locking feature is part of, firmly connected to or formed by a locking member. The locking member may comprise one or a plurality of locking features. If a plurality of locking features is provided, the locking features are preferably uniformly disposed or distributed in the angular or circumferential direction, particularly on or over the locking member. The locking features may be axially aligned. That is to say, the locking features may be arranged at corresponding axial positions. The locking features may be designed alike. The locking features are expediently rigid features. Specifically, all locking features may have the same configuration.

In an embodiment, the block feature is part of, firmly connected to or formed by a block member. The block member may comprise one or a plurality of block features. If a plurality of block features is provided, the block features are preferably uniformly disposed or distributed in the angular or circumferential direction, particularly on or over the block member. The block features may be axially aligned. That is to say, the block features may be arranged at corresponding axial positions. The block features may be designed alike. The block features are expediently rigid features. Specifically, all block features may have the same configuration.

In an embodiment, when the releasable locking interface is established, for releasing the interface, the locking feature may be movable relative to the block feature. The locking feature may be movable axially and/or radially with respect to the block feature, preferably only axially or only radially, for releasing the releasable locking interface and/or re-establishing the releasable locking interface. The directions for releasing the interface and re-establishing the interface may be opposite directions.

In an embodiment, the number of locking features is different from the number of block features, e.g. greater than or less than the number of block features.

In an embodiment, the block feature is rigid or rigidly mounted.

In an embodiment, the locking feature is flexible or flexibly mounted. The locking feature may be resilient or resiliently mounted. Accordingly, once the locking feature has been displaced relative to the block feature, the resilient restoring force may tend to move the block feature back to its original position, for example into engagement or abutment with the block feature. The resiliency may, for example, be used to release or re-establish the releasable locking interface.

In an embodiment, the release member is rotatable relative to the housing, the block feature, the locking feature, the block member and/or the locking member, e.g. at least in a limited way, preferably only in a limited way or in a non-limited way. The release member may be rotatable between a first angular position and a second angular position. The release member may be rotated starting from the first angular position towards and into the second angular position and, preferably, vice versa. In the first angular position, the releasable locking interface is expediently established. Consequently, when the release member is in the first angular position, rotation of the movable member in the decrementing direction is blocked. In the second angular position, the releasable locking interface is expediently released at least temporarily, preferably only temporarily or permanently. In this way, at least a limited rotation of the movable member in the decrementing direction may be allowed. The minimum angle by which the movable member may rotate in the decrementing direction may be defined by a unit increment, which is discussed further below.

In an embodiment, in the first angular position of the release member, the locking feature and the block feature are engaged or abut in order to establish the releasable locking interface. In the second angular position, the locking feature and the block feature are expediently disengaged to release the releasable locking interface.

In an embodiment, the assembly is configured such that the rotation of the release member from the first angular position to the second angular position causes the release of the releasable locking interface. For example, rotation of the release member may be converted into axial and/or radial movement of the locking feature relative to the block feature. As another example, the rotation of the release member may be used to remove a support from the locking feature which prevented a disengagement movement of the locking feature relative to the block feature, thereby enabling disengagement of locking feature and block feature.

In an embodiment, the second angular position is angularly offset from the first angular position, particularly in the decrementing direction.

In an embodiment, the axial position of the release member with respect to the housing and/or the locking feature is the same in the first and second angular positions. Alternatively, the release member may have different axial positions with respect to the locking feature and/or the housing in the first angular position and in the second angular position. Specifically, the release member may be axially shifted, when being rotated from the first angular position to the second angular position. For example, in the second angular position, the release member may be arranged more proximally than in the first angular position.

In an embodiment, the assembly is switchable between two different configurations, particularly two different axial configurations, preferably when the release member is in the first angular position. The two configurations may be a decrementing configuration and a driving configuration. The decrementing configuration may be a configuration, where the rotation of the movable member relative to the housing in the incrementing and decrementing directions is generally possible, where for the rotation in the decrementing direction, the release member has to be rotated. The driving configuration may be a configuration where the movable member is rotatable, preferably driven to rotate, in the decrementing direction. In the driving configuration, the movable member may be coupled to other components than in the decrementing configuration. A selective decrementing rotation of the movable member may no longer be possible in the driving configuration. In the decrementing configuration, the releasable locking interface is expediently established and may be selectively released by rotating the release member towards or into the second angular position. In the driving configuration, the releasable locking interface is expediently released, preferably permanently, at least until the mechanism is switched back again into the decrementing configuration. In order to switch between the driving configuration and the decrementing configuration, the locking feature and the block feature are preferably axially displaceable relative to one another. The locking feature may be displaced axially relative to the block feature, particularly in the distal direction, or vice versa in order to switch the assembly from the decrementing configuration into the driving configuration. In this way, axial movement is used to switch into the driving configuration, where rotational movement is used to release the locking interface in the decrementing configuration. The assembly may be switched from the decrementing configuration into the driving configuration and vice versa. Consequently, when the desired operation condition of the assembly has been set and the set operation condition has been verified by the user, which implies that a decrementing operation is not necessary any more, the mechanism can be switched into the driving configuration.

In an embodiment, the release member is axially displaceable, particularly in the distal direction, in order to switch the assembly from the decrementing configuration into the driving configuration. The release member may be coupled to either the block feature or the locking feature to move these features axially relative to one another to switch from the decrementing configuration into the driving configuration.

In an embodiment, a biasing member is provided which biases the block feature or member, the locking feature or member and/or the release member into the axial position for the decrementing configuration. In this way, the assembly may be switched automatically from the driving configuration into the decrementing configuration by means of the biasing member, without any user action being required.

In an embodiment, the movable member is operatively coupled to an energy storage member. The energy storage member may be a spring, such as a torsion spring. The spring may be coupled to the housing or fixed at the housing to provide a counter bearing. The movable member may be biased or biasable to rotate into the decrementing direction by energy stored or storable in the energy storage member. Rotation of the movable member in the incrementing direction preferably increases the energy stored in the energy storage member. The releasable locking interface may react a force or torque, which tends to rotate the movable member in the decrementing direction and is transferred to the movable member via the energy storage member when the interface is established. The energy or a part thereof can be released by releasing the interface in order to decrement the mechanism when rotating the release member towards or into the second angular position.

In an embodiment, energy stored within the energy storage member, preferably by the user which performs a rotation of the movable member in the incrementing direction, can be used to assist or perform one, an arbitrarily selected plurality of, or all of the following operations:
  releasing the releasable locking interface,
  re-establishing the releasable locking interface after it has been released,
  rotating the release member from the first angular position towards or into the second angular position,
  rotating the release member from the second angular position towards or into the first angular position,
  disengaging block feature and locking feature by, particularly radially and/or axially, displacing the locking feature relative to the block feature,
  re-engaging block feature and locking feature by, particularly axially and/or radially, displacing the locking feature relative to the block feature,
  driving relative radial and/or axial movement between the locking feature and the block feature,
  driving rotation of the movable member in the decrementing direction in the decrementing configuration,
  driving rotation of the movable member in the decrementing or driving direction in the driving configuration.

In an embodiment, the movable member is rotatable in the incrementing direction relative to the housing only by multiples, particularly by whole-number multiples, of a unit increment. One unit increment may be or correspond to the minimum size of a dose which can be set, for example. During a decrementing operation, the minimum unit decrement, that is to say the minimum amount by which the movable member has to be or can be rotated in the decrementing direction during a decrementing operation, may be greater than or equal to the unit increment. That is to say, the mechanism may be decremented unit increment by unit increment or only by a plurality of unit increments during a single decrementing operation. During decrementing, all of the previously incremented unit increments may be decremented in a single decrementing operation. The maximum unit decrement may be greater than or equal to the minimum unit decrement.

In an embodiment, the angular distance between the first angular position and the second angular position of the release member may be 90° or less, such as 40° or less, or 20° or less.

In an embodiment, the angular distance between the first angular position and the second angular position may correspond to and/or be defined by one unit increment or more unit increments, such as some whole number multiple of one unit increment. Alternatively, the angular distance may be unrelated to the unit increment.

In an embodiment, the assembly comprises at least one unidirectional interface, preferably a unidirectional rotational interface. This interface may allow relative rotation of one component forming the interface relative to the other component forming the interface in one rotational direction only, when it is established. Preferably, the unidirectional interface defines the unit increment, which expediently is defined by the minimum angle by which the movable member can be rotated. The unidirectional interface may be formed between a static component, such as the housing, and a rotating component which is rotatable in the incrementing direction, such as the movable member or a component coupled to the movable member rotationally at least in the decrementing configuration. The unidirectional interface may be a releasable interface.

When the release member is in the first angular position and the assembly is in the decrementing configuration, the unidirectional interface is expediently established, e.g. permanently or only temporarily. Thus, when the release member is in the first angular position and expediently the assembly is in the decrementing configuration, rotation of the movable member relative to the housing is permitted in the incrementing direction only. When the assembly is in the driving configuration, the unidirectional interface is preferably released. Relative axial movement between the components establishing the interface may be used for this purpose.

In an embodiment, the assembly comprises a dosing member. The dosing member may be arranged to be rotatable in the incrementing direction to increment or increase the size of the set dose, which is to be delivered by the device or the assembly, and in the decrementing direction to decrease or decrement the size of the dose. For doing so, the dosing member may be rotatable, preferably at least in limited way, in the incrementing direction and/or the decrementing direction. The release member may be coupled to or formed by the dosing member. The coupling between release member and dosing member may be such that axial and/or rotational relative movement between release member and dosing member is prevented.

In an embodiment, the movable member is coupled to, preferably axially and/or rotationally, or formed by a dose indication member. The dose indication member may comprise indicia which provide information to the user about the size of the currently set dose. A dose indication member may be a number sleeve, for example.

In an embodiment, in the decrementing configuration, the locking feature or member or the block feature or member is permanently rotationally locked relative to the housing against rotation in the decrementing direction and/or in the incrementing direction. The other feature or member, expediently the one which is not locked against rotation in the decrementing direction may be rotatable in the decrementing direction relative to the housing, but preferably only when the releasable locking interface has been released. The respective feature or member may be secured against relative rotation with respect to the housing in the decrementing configuration and in the driving configuration or rotational movement of the respective feature or member relative to the housing may be allowed in the driving configuration.

In an embodiment, the unidirectional interface is the releasable locking interface. Consequently, the interface, which defines the unit increment, may be used to establish the releasable locking interface and may be released to decrement the mechanism. Thus, the locking features and/or the block features may be arranged to define the unit increment.

In an embodiment, the unidirectional interface is different from the releasable locking interface. Thus, there may be two interfaces operative or established at the same time, i.e. the unidirectional interface and the releasable locking interface. The releasable locking interface is, preferably, arranged, as seen in the force path, between the unidirectional interface and the movable member. A separate component may be provided to establish the unidirectional interface and/or the releasable locking interface, where separate features for both interfaces may be integrated in a single component or formed in separate components.

In an embodiment, the unidirectional interface governs or determines rotation of the movable member in the incrementing direction and the releasable locking interface governs or determines the selective rotatability of the movable member in the decrementing direction.

In an embodiment, the respective interface, unidirectional interface and/or releasable locking interface, is a radial interface or an axial interface.

In an embodiment, for switching into the driving configuration of the assembly, the locking member and the block member are axially displaceable relative to each other. The locking member may be displaced axially relative to the block member or the block member may be displaced axially relative to the locking member. When switching from the decrementing configuration into the driving configuration, the unidirectional interface may be released. Alternatively or additionally, the releasable locking interface may be released.

In an embodiment, the locking features and/or the block features are arranged in a pitch which is determined by features used to define the unit increments. The number of locking and/or block features may be equal to the number of features used to define the unit increments.

In an embodiment, the releasable locking interface blocks relative rotational movement in both rotational directions. Consequently, when the releasable locking interface is established, relative rotational movement between the locking feature and the block feature may be prevented or blocked in both rotational directions.

In an embodiment, the assembly comprises a plurality of block features and/or locking features. This ensures that, when the assembly switches from the driving configuration back into the decrementing configuration, a defined relative angular orientation between locking feature(s) and block feature(s) is obtained more easily, which may be necessary for re-establishing the releasable locking interface. Particularly, any user induced rotation to re-establish the releasable locking interface may be avoided in this way or considerably reduced.

In an embodiment, the angular pitch, in which the block features and/or the locking features are arranged corresponds to or is determined by the angular pitch of features, for example ratchet features, which are used to form the unidirectional rotational interface and/or to define the unit increment.

In an embodiment, the assembly comprises a driven member. The driven member is preferably rotationally locked relative to the housing in the decrementing configuration. The driven member may be rotatable relative to the housing in the driving configuration of the assembly. For switching between the decrementing configuration and the driving configuration, the driven member may be axially displaceable relative to the housing. Axial movement of the release member, particularly in the distal direction, may be transferred to the drive member in order to switch from the decrementing configuration into the driving configuration. In the driving configuration, the driven member may be rotationally locked to the movable member. In the decrementing configuration, there is preferably no rotational lock between the movable member and the driven member. In the decrementing configuration, the movable member may be rotatable relative to the driven member when the movable member rotates in the decrementing or incrementing direction. The driven member may be coupled to a piston rod in order to drive distal movement of a piston rod to dispense drug.

In an embodiment, the locking member is selected from one of the following members: movable member, driven member, housing, a member different from the previous members. This does not imply that any of these members has to be present in the assembly mandatorily.

In an embodiment, the block member is selected from the following members: movable member, driven member, housing, a member different from the previous members. This does not imply that any of these members has to be present in the assembly mandatorily.

In an embodiment, the block member and the locking member are different members.

If the locking member is formed by a member different from the driven member and/or the movable member, the locking member may be permanently rotationally locked with respect to the housing in both rotational directions, i.e.

the incrementing direction and the decrementing direction. If the block member is formed by a member different from the driven member and/or the movable member, the block member may be permanently rotationally locked with respect to the housing in both rotational directions, i.e. the incrementing direction and the decrementing direction. Thus, for the respective member, i.e. the block member or the locking member, a permanently static component may be used. Alternatively, a component which is static in the decrementing configuration may be used, where this component can be movable, for example rotatable, in the driving configuration as, in the driving configuration, the locking system is not needed, as rotation of the movable member in the decrementing direction is desired.

In an embodiment, the release member is biased towards the first angular position or against displacement away from the first angular position towards the second angular position. Consequently, the first angular position may be the regular position of the release member. The bias force may have to be overcome, for example by the user, in order to move the release member into the second angular position. When the release member is in the second angular position, the bias force may tend to move the release member towards the first angular position. Alternatively, there may be no bias force in the second angular position.

In an embodiment, the release member is releasably rotationally locked in the second angular position relative to the housing and/or the locking feature. Particularly, rotation towards the first angular position and/or away from the first and second angular positions may be prevented by means of the releasable rotational lock in the second angular position. Particularly, in this way, it can be guaranteed, that the release member is stabilized in the second angular position until it is rotated back towards the first angular position in order to resume its regular operating position.

In an embodiment, in the decrementing configuration, in the first angular position of the release member, the locking feature may be supported against radial and/or axial movement out of or into engagement or abutment with the block feature. In the second angular position, the support may have been removed such that the releasable locking interface can be released by relative movement, e.g. relative radial and/or axial movement, between block feature and locking feature.

In an embodiment, the locking feature and/or the block feature is oriented in the radial direction.

In an embodiment, the locking feature and/or the block feature is oriented in an axial direction.

In the present disclosure, when a feature or member is recited to extend or to be oriented in the axial direction, it may have a free axial end. In the present disclosure, when a feature or member is recited to extend or be oriented in the radial direction, it may have a free radial end.

In an embodiment, locking feature and block feature are oriented in the same direction, e.g. axially or radially, or in different directions, e.g. one axially and the other one radially.

In an embodiment, the assembly comprises a support feature. The support feature is expediently rotatable relative to the locking feature between a first position and a second position. In the first position, the support feature expediently supports the locking feature, preferably radially and/or axially. Consequently, when the support feature is in the first position relative to the locking feature, radial or axial displacement of the locking feature is prevented. In this way, the locking feature may be kept in engagement or abutment with the block feature and the releasable locking interface may be stabilized or prevented from being released. In the second position, relative movement, e.g. radial and/or axial movement, between locking feature and block feature may be allowed. In the second position, the support feature may no longer support the locking feature, such that the locking feature can be displaced, e.g. radially and/or axially, out of abutment or engagement with the block feature thereby releasing the releasable locking interface established between the locking feature and the block feature. The assembly is expediently configured such that the support feature is in the first position, when the release member is in the first angular position, and the support feature is in the second position when the release member is in the second angular position. The locking feature may be arranged between the support feature and the block feature as seen in the radial or axial direction, when it is supported by the support feature.

In an embodiment, when the support feature is in the first position, the support feature stabilizes the locking feature against radial and/or axial displacement. In particular, the support feature stabilizes the locking feature against displacement, which would be effected on account of torque or force transferred, e.g. from the energy storage member, via the block feature to the locking feature. When the support feature is in the second position, the locking feature, particularly as it is no longer supported, may be displaced relative to the block feature, e.g. radially and/or axially, on account of the torque or force. Consequently, the torque or force transferred from the energy storage member can be used to release the releasable locking interface.

In an embodiment, the support feature is part of or firmly connected to a support member. The support member may be formed by the release member or by a separate member, which is preferably operatively coupled to the release member in particularly rotationally. The support member may thus follow rotational movement of the release member, when the release member is rotated from the first angular position to the second angular position.

In an embodiment, the block features extend or are oriented in the radial direction. The block features may be designed to be disengaged by relative radial movement between the locking feature and the block feature. The block features are preferably designed to cooperate with the locking feature in order to form a unidirectional radial ratchet interface, particularly as the releasable locking interface. The unidirectional radial ratchet interface preferably permits rotation of the movable member relative to the block member in the incrementing direction, but blocks rotation of the movable member relative to the block member in the decrementing direction.

In an embodiment, the locking feature is flexibly and/or resiliently displaceable, preferably in the radial direction, particularly with respect to the remainder of the locking member, which may be the movable member.

In an embodiment, the release member comprises a plurality of member features, preferably radially extending or radially oriented member features. The member features are preferably circumferentially or angularly disposed or distributed in a uniform way on or over the release member.

In an embodiment, the member features protrude radially with respect to the block features. Particularly, the radial extension of the member features is greater than the one of the block features. The member features preferably protrude with respect to the block feature by a length which is greater than or equal to one of the following values: radial extension of the locking feature, radial extension of the block features.

In an embodiment, the member features and the block features are adjusted to one another, such that at least one of, an arbitrarily selected plurality of, or all of the following characteristics are matched to one another, preferably equal:
- number of features,
- angular pitch, in which the features are distributed over the respective member,
- inclination, particularly with respect to the radial direction, of a side face delimiting the feature in a first angular direction, e.g. in the incrementing direction,
- inclination, particularly with respect to the radial direction, of a side face delimiting the feature in a second angular direction, e.g. the decrementing direction,
- angular width of the features at corresponding radial positions.

In an embodiment, the release member and the block member are arranged with respect to each other such that block features and member features overlap as seen in the axial direction, in particular, when the release member is in the first angular position.

In an embodiment, the axial extension of the locking feature(s) is greater than the axial extension of the block feature(s) and greater than the axial extension of the member feature(s). Particularly, the axial extension of the locking feature may be chosen such that the locking feature may interact with a block feature and a member feature, which are axially arranged in succession with respect to one another, simultaneously.

In an embodiment, the release member and the block member are arranged in axial succession, e.g. on one another in a stacked fashion, and preferably such that each member feature overlaps with a different one of the block features when the release member is in the first angular position.

In an embodiment, the release member comprises at least one release feature. The release feature expediently radially protrudes with respect to the block features in the assembly. When the release member is rotated relative to the block member, the movable member, the housing and/or the locking feature from the first angular position towards the second angular position, the locking feature is preferably displaced radially. The radial displacement is expediently achieved on account of an operative coupling or interaction between the locking feature and the release feature. The locking feature is preferably radially displaced until the releasable locking interface is released, thereby allowing rotation of the movable member relative to the block member in the decrementing direction. The release feature may be realised by one of the member features. As the release feature radially protrudes with respect to the block features, it can be maintained in cooperation with the locking feature, when the block features can no longer interact with the locking feature. Thus, a defined position of the locking feature may be maintained, even in the second angular position.

In an embodiment, the release member, particularly in addition to the release feature, comprises a stop feature. When the locking interface has been released, the movable member is preferably rotatable, e.g. in a limited way, in the decrementing direction relative to the release member. The relative rotational movement may be stopped when the locking feature abuts the stop feature. Consequently, the energy, which drives movement of the movable member in the decrementing direction, may be transmitted to the user, as the release member is expediently linked to the user, who controls the decrementing operation of the assembly. Thus, the user has increased confidence that the decrementing operation is successfully achieved. The stop feature may be realised by one of the member features, preferably by the one adjacent to the release feature.

In an embodiment, the stop feature and the release feature are formed by different member features. Particularly, stop feature and release feature may be formed by adjacent member features. Consequently, features as disclosed above with respect to member features may also be disclosed with respect to the release feature or the stop feature and vice versa.

In an embodiment, when the release member is in the first angular position, the locking feature is arranged in a first pocket defined between two block features and, preferably, simultaneously in a second pocket defined between two member features. The two pockets may be axially offset from one another. When the release member is rotated towards the second angular position, e.g. in the decrementing direction, the locking feature is expediently radially displaced out of the first pocket but remains in the second pocket. In the second angular position of the release member, the locking feature may be arranged in the second pocket.

In an embodiment, after the locking feature has disengaged the first pocket, the movable member is rotatable, e.g. in a limited way, relative to the release member, preferably until the locking feature abuts the member feature delimiting the second pocket in the decrementing direction. In this way, the drive torque or drive force exerted by the energy storing member may be transmitted to the user, in particular via the movable member, the locking feature, and the release member. As long as the user reacts the drive force or torque, the movable member does not rotate in the decrementing direction, although the force transferred to it tends to drive this movement. If the force or torque is no longer reacted, e.g. if the user releases the release member, then the drive torque can drive a decrementing rotation of the movable member, e.g. by one unit increment. As the release member is no longer maintained in the second angular position, it can rotate back into the first angular position relative to the locking feature. This rotation may be driven by the elastic or resilient force—e.g. on account of the resilient displacement of the locking feature performed previously to disengage locking feature and block features—which tends to re-engage the locking feature with the block features when the locking feature mechanically interacts with the release member.

In an embodiment, when the release member is rotated towards the first angular position, particularly starting from the second angular position relative to the housing, the locking feature may be displaced towards the block features and re-engage with the block features such that further rotation of the movable member in the decrementing direction is prevented as the releasable locking interface has been re-established.

In an embodiment, the release member and/or the block member are axially displaceable relative to the locking feature, e.g. in the distal direction, in order to switch into the drive configuration of the assembly. When the assembly is switched into the driving configuration, the locking feature may be disengaged from the block features and the member features. When the assembly is switched from the driving configuration back into the decrementing configuration, the locking feature may be arranged in a pocket between two different member features than it previously has been. Particularly, in the decrementing configuration, the locking feature may be consistently arranged in a pocket defined between the same two member features but during incrementing and decrementing be displaced into different pockets between adjacent block features.

In an embodiment, the release member comprises a circumferential track, preferably a closed circumferential track, e.g. an annular track. The track may extend angularly around the entire release member. In the driving configuration, the locking feature is expediently arranged within the track. In the decrementing configuration, the locking feature is expediently arranged outside of the track. The track may enable free rotation of the movable member relative to the release member in the driving configuration.

In an embodiment, the locking member is rotationally locked relative to the housing, preferably at least in the decrementing configuration, e.g. in the decrementing and the driving configuration or only in the decrementing configuration. The locking member may be formed by the driven member or a static component, for example.

In an embodiment, the block member is formed by the movable member.

In an embodiment, the locking member comprises a plurality of locking features, which are preferably oriented axially.

In an embodiment, in the first angular position of the release member, one locking feature and the block feature are engaged or abut to establish the releasable locking interface. In the second angular position, that particular locking feature and the movable member are disengaged to release the releasable locking interface.

In an embodiment, in the second angular position of the release member, the block feature engages or abuts a different locking feature to establish the releasable locking interface with that locking feature of the locking member. Thus the releasable locking interface may be released sequentially such that the movable member is allowed to rotate in the decrementing direction at least or only until the block feature abuts the subsequent locking feature.

In an embodiment, the locking features are circumferentially or angularly and preferably uniformly disposed on the locking member, e.g. ring-like. The locking features may extend or be oriented in the axial direction.

In an embodiment, the locking features are distributed in a comb-like structure over the locking member.

In an embodiment, the locking features are arranged to define the unit increment. Particularly, an angular extension of the locking features may define the unit increment.

In an embodiment, the respective locking feature is flexible or mounted flexibly in such a manner that it can be deflected, preferably axially and/or radially, e.g. in an elastic way. The respective locking feature may, however, react a rotational, angular or tangential load or force. Particularly, the locking feature is able to react the drive force or torque transferred to the locking feature from the energy storage member.

In an embodiment, the respective locking feature has at least one radial and/or axial face, preferably two faces, and/or at least one angular face, preferably two faces. The angular face may be designed to be exposed to the force or load. The radial or axial face may be designed to be contacted in order to maintain the locking feature in a defined radial or axial position, e.g. a radially or axially displaced position or a non-displaced position. One radial or axial face may be designed to interact with the support feature to maintain the axial or radial orientation or position of the locking feature, e.g. an undisplaced position. Thus, for example, one radial face may be designed to interact with the support feature to maintain the locking feature in a radially non-displaced position One radial or axial face, which expediently faces away from the previously mentioned radial or axial face, may be. designed to interact with the block feature to maintain the radially or axially displaced locking feature in a radially or axially displaced position. The respective angular face may be designed to be contacted to displace the locking feature radially or axially.

In an embodiment, the block feature is arranged to contact or contacts the angular face of a locking feature, particularly of only one locking feature. The angular face which is contacted by the block feature may delimit the locking feature in the incrementing direction. Preferably, the block feature contacts the radial or axial face of at least one second locking feature next to the first locking feature simultaneously to the angular face of the first locking feature. The second locking feature may have been radially or axially displaced and be maintained in the displaced state by the block feature.

In an embodiment, at least one of or both of the block feature and the locking feature have a side face which is inclined, particularly with respect to the radial or axial direction. The inclined side face abuts the other one of the block feature and the locking feature or, if both features do have inclined side faces, the inclined side faces abut. In this way, if a force or torque is transferred via the inclined side face to the locking feature, this results in a tendency to displace the locking feature axially or radially, particularly inwardly. This displacement may be used to release the releasable locking interface formed between a particular locking feature and the block feature. The side face of the locking feature may be the angular face discussed above.

In an embodiment, the block feature is arranged to contact a feature of the release member, when the release member is rotated in the incrementing direction, particularly together with the movable member. That is to say, the block feature may be designed to interact with the locking feature for achieving a releasable locking of the movable member against rotation in the decrementing direction and to interact with the release member in order to rotate the movable member in the incrementing direction.

In an embodiment, the support feature is arranged to support one or more locking features radially or axially in order to preserve the axial or radial orientation of the supported locking feature. The support feature may be arranged to support one or more locking features radially in order to preserve the radial position of the supported locking feature. The support feature may be arranged to support one or more locking features axially in order to preserve the axial position of the supported locking feature. The locking feature, of which the angular face is contacted by the block feature is expediently supported by the support feature.

In an embodiment, the assembly comprises a support member. The support member preferably comprises the support feature. The support member is expediently rotatable relative to the locking member to selectively support one or more locking features with the support feature, particularly radially.

In an embodiment, the support member is coupled with the release member to follow rotation of the release member, preferably in both rotational directions. Preferably, the coupling is configured to have a rotational clearance. Therefore, the release member may rotate relative to the support member before the support member follows rotation of the release member. In this way, it can be achieved that mechanical interaction between the block feature and the release member is removed before the support member is rotated, e.g. in the decrementing direction. Alternatively or additionally, it can be achieved, that the block feature is displaced, for example in the incrementing direction, relative to the locking features before the support feature is displaced in the incrementing direction. In this way, it can be facilitated that a locking feature can be radially or axially displaced, e.g. radially inwardly or outwardly, without the block feature and/or the support feature blocking the respective displacement.

In an embodiment, the rotational clearance is greater than or equal to the angular distance corresponding to or defined by one of the following values: one unit increment, two unit increments, three unit increments, four unit increments.

In an embodiment, the rotational clearance is defined by, corresponds to or is related to a whole number multiple of the unit increment. The rotational clearance may be defined by, correspond to or be related to one of the following values: one unit increment, two unit increments, three unit increments, four unit increments. Alternatively, the rotational clearance and the unit increment may be unrelated.

In an embodiment, the support feature is arranged to selectively support a locking feature such that it can withstand the load transferred to the supported locking feature via the block feature. If the locking feature is no longer supported, the load transferred to the locking features by the block feature does result in a displacement, particularly in the axial or radial direction, e.g. the inward direction, of that locking feature which, in turn, allows the movable member to rotate in the decrementing direction. Consequently, when the support feature is rotated in the decrementing direction, the block feature and, along with it, the movable member, may follow the rotation and also rotate in the decrementing direction, e.g. driven by the force or torque transferred from the energy storage member. The force of the energy storage member may be used for disengaging the unsupported locking feature and the block feature.

In an embodiment, when the release member is rotated in the decrementing direction from the first angular position towards the second angular position, the support member rotates in the same direction, thereby removing support from the one of the locking features. When the support has been removed, rotation of the movable member in the decrementing direction is allowed. Thereby, the no longer supported locking feature may be displaced, particularly axially or radially, e.g. inwardly.

In an embodiment, when the movable member has been rotated in the decrementing direction, the block feature expediently contacts the angular face of a subsequent locking feature. If that subsequent locking feature is supported against radial or axial displacement by the support feature, rotation in the decrementing direction of the movable member is stopped. When it is not supported, rotation in the decrementing direction is continued until the release member is no longer rotated and the block feature abuts the angular face of a locking feature, which is radially or axially supported by the support feature.

In an embodiment, the angular distance between the support feature and the block feature is less than the angular width of the locking features, particularly when the release member is in the first angular position. This ensures that radial movement of the locking feature is prevented by the support feature, in particular radial movement of that locking feature, which is contacted by the block feature. The angular distance may be increased during a decrementing operation until the no longer supported locking feature is displaced radially and the block feature also rotates in the decrementing direction.

In an embodiment, the support member or support feature is operatively coupled to the movable member. The coupling may be designed to establish or maintain a defined relative position, in particular an angular position, between the support feature and the movable member. The defined relative position may be the same relative position regardless of the absolute angular position of the movable member. In this way, it can be achieved that, if the movable member is rotated in the incrementing direction, the support feature follows this rotational movement and supports that locking feature which has just previously been passed by the block feature. The coupling may be a resilient coupling or a biased coupling, for example established by way of by a spring between the movable member and the support member, wherein the coupling may be configured to exert a force which tends to rotate the support member in the incrementing direction as well. In this way, it can be guaranteed that the support member follows rotational movement of the movable member in the incrementing direction, even if there is a rotational clearance between the release member and the support member. It can further be avoided that, if the dose has been incremented by one increment which might be indicated to the user via the movable member or number sleeve, and the user releases the movable member thereafter, the movable member rotates back in the decrementing direction until the block feature interacts with a supported locking feature. The coupling may be established by a spring, such as a biased compression spring which is provided between the movable member and the support member. In this way, the support member may follow rotation of the movable member, expediently even before a rotational clearance is closed between the support member and the release member.

In an embodiment, the support member is biased relative to the movable member. A bias spring, e.g. a compression spring, may be provided for this purpose, particularly between the movable member and the support member. The bias may tend to move the support member in the incrementing direction relative to the movable member, the block feature or the block member. The bias may have to be overcome or is increased by the user when the user rotates the release member in the decrementing direction.

In an embodiment, the support feature is biased into the first position at least when the release member is in the first angular position and, preferably, also when the release member is in the second angular position. This distinguishes the first angular position as the position assumed during regular operating position. The support feature may be provided on the release member. In this case, the first position of the support feature may coincide with the first angular position of the release member and the second position may coincide with the second angular position.

In an embodiment, the locking member, e.g. the locking feature, mechanically cooperates with the release member to releasably lock the release member in the second angular position, in particular when the release member has been rotated from the first angular position into the second angular position. The locking member may provide a, preferably resilient force, which hinders rotation of the release member back into the first angular position. However, if this force is overcome, for example by the user, this rotation can be achieved. When the release member is rotated back into the first angular position, the locking feature and the block feature may be re-engaged. Rotational movement of the release member relative to the locking feature from the second angular position to the first angular position may be used to drive the movement of the locking feature back into engagement with the block feature(s). In particular, the support feature may be used to displace the locking feature radially or axially while rotating from the second position to the first position.

In an embodiment, the locking member comprises, in addition to the locking feature, a unidirectional interface feature for establishing the unidirectional interface. Consequently, the locking member may be used as a clutch member. The clutch member may provide a clutch between the movable member and that member which is used as counterpart for the unidirectional interface, e.g. the housing. The interface of the clutch member to the movable member may be the releasable locking interface. The unidirectional interface may be formed by means of the unidirectional interface features. Consequently, the unidirectional interface and the releasable locking interface are different interfaces. This enables that the incrementing and decrementing mechanism can be governed by two different interfaces. The incrementing operation is governed by the unidirectional interface, whereas the releasable locking interface governs the decrementing operation. Independent tuning of the incrementing and decrementing operations is facilitated in this way.

In an embodiment, the locking feature is radially or axially displaceable relative to the unidirectional interface feature, in particular for releasing the releasable locking interface.

In an embodiment, the assembly comprises a stop feature. The stop feature may be arranged to limit rotation of the release member relative to the locking feature into the decrementing direction. The stop feature may define the second angular position. The stop feature may be provided on the locking member.

In an embodiment, the locking member may be the locking feature. For example, the locking member is a pin. The pin may be straight. The pin may have a length which is defined by an inner diameter of the block member. The pin may be received within the block member. The movable member may be used as the block member.

In an embodiment, the locking member or locking feature is axially displaceable, preferably only axially, from a locked position to an unlocked position relative to the block member for releasing the releasable locking interface. Expediently, the locking feature may be operatively coupled to the release member, such that the rotational movement from the first angular position towards the second angular position is converted into axial movement from the locked position towards the unlocked position. When the release member is in the first angular position, the locking feature is preferably in the locked position, e.g. abutting the block feature and/or to prevent rotation of the movable member in the decrementing direction. When the release member is in the second angular position the locking feature is preferably in the unlocked position, the releasable locking interface then being released.

In an embodiment, the block member comprises a guide track. The guide track may be provided to interact with the locking feature. The guide track may comprise at least two different types of sections, a locked section and an unlocked section. The locked section may be defined or limited by one or a plurality of block features, e.g. in only one or both angular directions. The locked section may extend axially or be oriented axially. The unlocked section may extend helically. As seen along the guide track, locked sections and unlocked sections may be alternatingly disposed. Consequently, as seen along the guide track, a first locked section is followed by a first unlocked section, which, again, is followed by a locked section, where the latter locked section may be the first locked section or a different locked section. The respective section may be defined by profiled features which delimit the section. The guide track may comprise one or more locked sections and one or more unlocked sections. The locking feature is provided to interact with the locked and unlocked sections.

In an embodiment, the assembly is configured such that, when the release member is in the first angular position, the locking feature is in the locked position and interacts with the locked section of the guide track. When the release member is rotated towards the second angular position, the locking feature may be displaced axially towards and/or into the unlocked position, where it can cooperate with the unlocked section.

In an embodiment, when the locking feature cooperates with a locked section of the guide track, the releasable locking interface is established. Thus, rotation in the decrementing direction of the block feature and, accordingly, the block member relative to the locking feature may be prevented. Therefore, in the locked position, the releasable locking interface may be established. When the locking feature cooperates with the unlocked section, relative rotation between locking feature and block feature in the decrementing direction is allowed. Consequently when and/or while the locking feature cooperates with the unlocked section, the releasable locking interface may be released. Preferably, on account of the helical configuration of the unlocked section, the relative rotation can be used to displace the locking feature axially from the unlocked position back into the locked position.

In an embodiment, the locking member or locking feature is operatively connected to the release member, e.g. in order to convert rotation of the release member into axial displacement of the locking feature, particularly from the locked position to the unlocked position and preferably vice versa. The locking member or locking feature may be operatively coupled to the release member via at least two interfaces, e.g. a helical interface and an axial interface. These interfaces may be established or operative simultaneously. Consequently, as the axial interface rotationally constrains the locking member or locking feature and the locking member or locking feature is also coupled to the release member via the helical interface, rotation of the release member may be converted into an axial displacement of the locking member or locking feature, which can be used to move the locking member or locking feature axially from the locked position to the unlocked position and/or vice versa.

In an embodiment, the assembly is configured such that, when the block member rotates in the decrementing direction, the locking feature cooperates with the unlocked section and is axially displaced towards the locked position until the locking feature interacts with the locked section or a different locked section of the guide track to re-establish the releasable locking interface.

In an embodiment, the assembly comprises a clutch member. The clutch member may be configured to provide an interface with the locking feature.

In an embodiment, the clutch member comprises an interface slot, particularly for one of the interfaces via which the locking feature is operatively connected to the release member.

In an embodiment, the release member comprises an interface slot, particularly for the other interface via which the locking feature is operatively connected to the release member.

In an embodiment, the locking member or locking feature extends through the interface slot of the release member and the interface slot of the clutch member. Specifically, the locking member or locking feature may be simultaneously engaged with an axial slot in the clutch member and with a helical slot in the release member. The clutch member and/or the release member may comprise two oppositely disposed interface slots where the locking member or locking feature extends through both of the oppositely disposed interface slots.

In an embodiment, the clutch member comprises a unidirectional interface feature, which is designed to establish the unidirectional interface, which defines the unit increment, e.g. in cooperation with corresponding features defined in the housing or another static component.

In an embodiment, the clutch member comprises a unidirectional interface feature, e.g. a ratchet feature which is designed to establish a unidirectional interface, e.g. a unidirectional ratchet interface, the unidirectional interface permitting rotational movement with respect to the housing in one direction only, e.g. the incrementing direction, where the unidirectional rotational interface is preferably present in addition to the releasable rotational locking interface.

In an embodiment, the guide track is a closed track, particularly in the angular direction. That is to say, it preferably extends over 360° in the angular direction. In particular, there may be no open angular end of the track.

In an embodiment, the guide track comprises one or more open axial ends. The respective open end may be provided in the locked section of the track. The open ends may provide access to the guide track, e.g. for the locking member. The one or more axial ends may face in the same axial direction or in different axial directions, preferably opposite axial directions.

In an embodiment, at least one of the locked sections, particularly every locked section, has at least one open end in the axial direction, particularly the distal direction. This end is arranged to permit that the locking member or locking feature can leave and/or re-enter the guide track through the open end. In this way, the locking member or locking feature can be disengaged from the guide track, for example in order to switch from the decrementing configuration into the driving configuration of the assembly. The unlocked sections may be closed in both axial directions.

A particularly advantageous embodiment of an assembly for a drug delivery device comprises: a housing, a movable member, which is arranged to be rotatable in two opposite rotational directions with respect to the housing, i.e. in an incrementing direction and a decrementing direction, the movable member being preferably operatively coupled to an energy storage member and biased to rotate into the decrementing direction by energy stored or storable in the energy storage member, wherein rotation of the movable member in the incrementing direction increases the energy stored in the energy storage member, the assembly further comprising a locking system, the locking system comprising a locking feature, a block feature, and a release member, wherein the locking feature is arranged to cooperate with the block feature to form a releasable locking interface, the releasable locking interface being configured such that, when the releasable locking interface is established, rotational movement of the movable member relative to the housing is blocked in the decrementing direction, preferably only in the decrementing direction, and wherein, when the releasable locking interface is released, the movable member is rotatable in the decrementing direction, e.g. at least in a limited way, preferably only in a limited way or in a non-limited way, wherein the release member is rotatable relative to the housing and/or the locking feature, e.g. at least in a limited way, preferably only in a limited way or in a non-limited way, between a first angular position and a second angular position, wherein, in the first angular position, the releasable locking interface is established, and, in the second angular position, the releasable locking interface is released at least temporarily, preferably only temporarily or permanently, where the assembly is configured such that the rotation of the release member from the first angular position to the second angular position causes the release of the releasable locking interface.

The term "medicament" or "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, expediencies and advantages of the present disclosure will become apparent from the following description of the exemplary embodiments in conjunction with the drawings.

FIG. 5b shows a detail of the embodiment of FIG. 5a.

In the figures, identical elements, identically acting elements, and elements of the same kind may be referenced using the same reference numerals.

DETAILED DESCRIPTION

Figure 1:
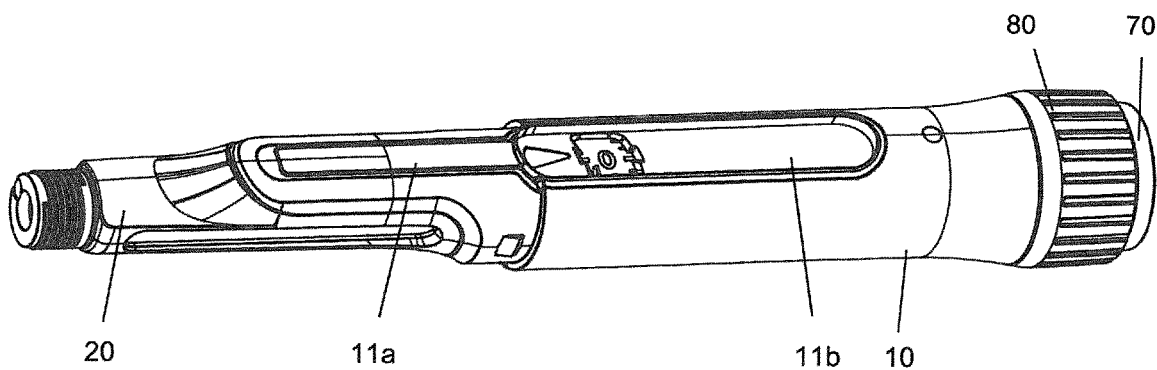
FIG. 1 shows a perspective view of an embodiment of a drug delivery device.
Figure 2:
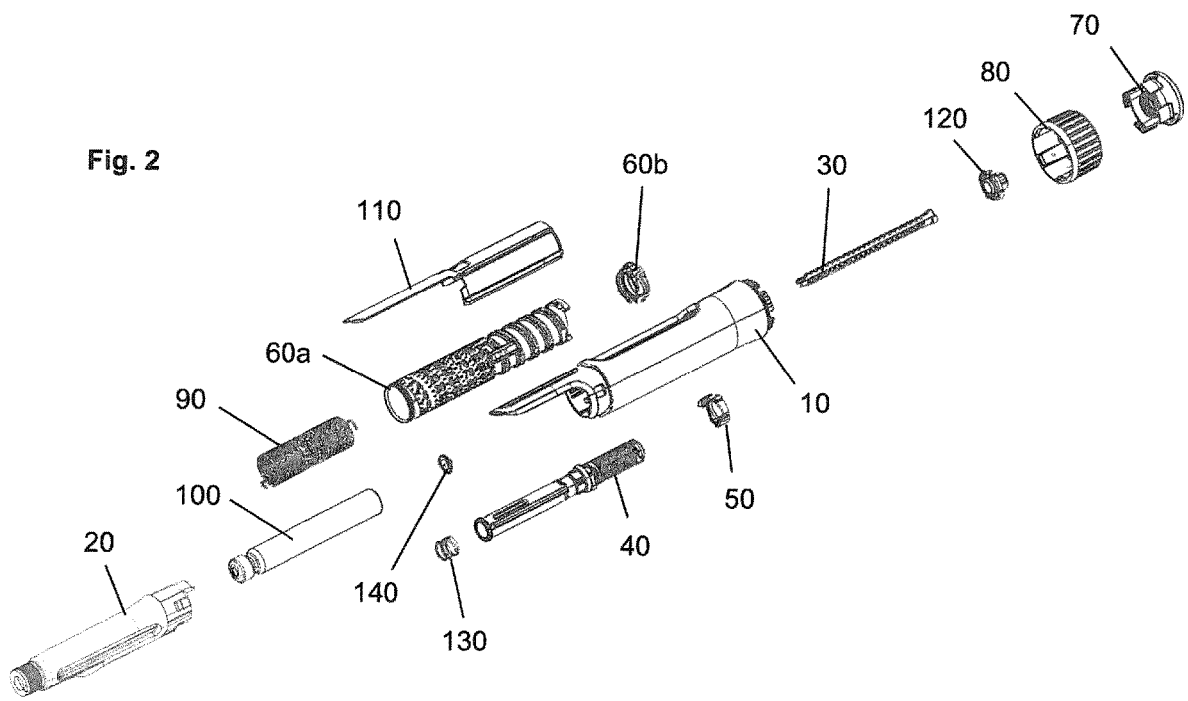
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged. All components are located concentrically about a common principal axis I (FIG. 3b) of the mechanism.

The housing 10 or body is a generally tubular casing element having a proximal end with an enlarged diameter. The housing 10 provides location for the liquid medication cartridge 100 and cartridge holder 20. As shown in FIGS. 1 and 2, the housing comprises a first window 11a and a second window (or lens) 11b which are incorporated into the housing body e.g. by twin-shot moulding. The windows 11a, 11b may be moulded during a first shot in a translucent (and preferably transparent) material, and the outer cover of the housing is moulded during a second shot in an opaque material.

In the embodiment of FIGS. 1 to 3b the housing comprises an insert 12 (best shown in FIG. 4) as an integral part located as an inner wall near the distal end of the housing. The insert 12 may be moulded in the translucent material. As an alternative, the insert or parts thereof may be formed in the opaque material or as a separate component part as depicted in the embodiment of FIG. 4.

The insert 12 is a cup-shaped component part with a sidewall 13 and a tube 14 extending through the insert 12, thus forming an annular space there between. Arms 15 extend radially outwards from the sidewall 13. A bottom wall 16 connects the sidewall 13 and the tube 14 on the distal side of the insert 12, whereas the opposite proximal side is open. The insert 12 has various interfaces. For example, the tube 14 of insert 12 comprises an inner thread 17 engaging the piston rod 30. In addition the radial space between the tube 14 and the outer sidewall 13 may provide a bearing area receiving the drive spring 90 and the clutch spring 130. Further, spline teeth 18 are provided on the insert 12 engaging corresponding spline teeth 41 at the distal end of drive sleeve 40. Teeth 18 interact with drive sleeve 40 to rotationally couple and de-couple the drive sleeve and the housing 10.

Figure 4:
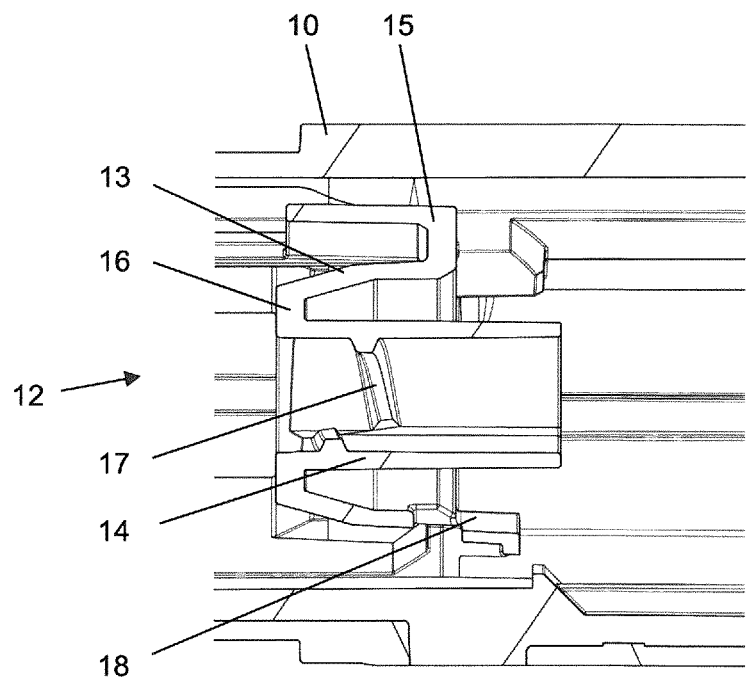
FIG. 4 shows, in a sectional view, a detail of a device according to another embodiment.

In the embodiment of FIG. 4, the insert is an integral part of an inner housing shell which inner shell is partially surrounded by an external housing shell. The shells may be formed by two consecutive shots of injection moulding such that the shells are permanently attached to each other. For example, the inner shell is formed from a transparent or translucent material, whereas the outer shell is formed from an opaque material.

Figure 5A:
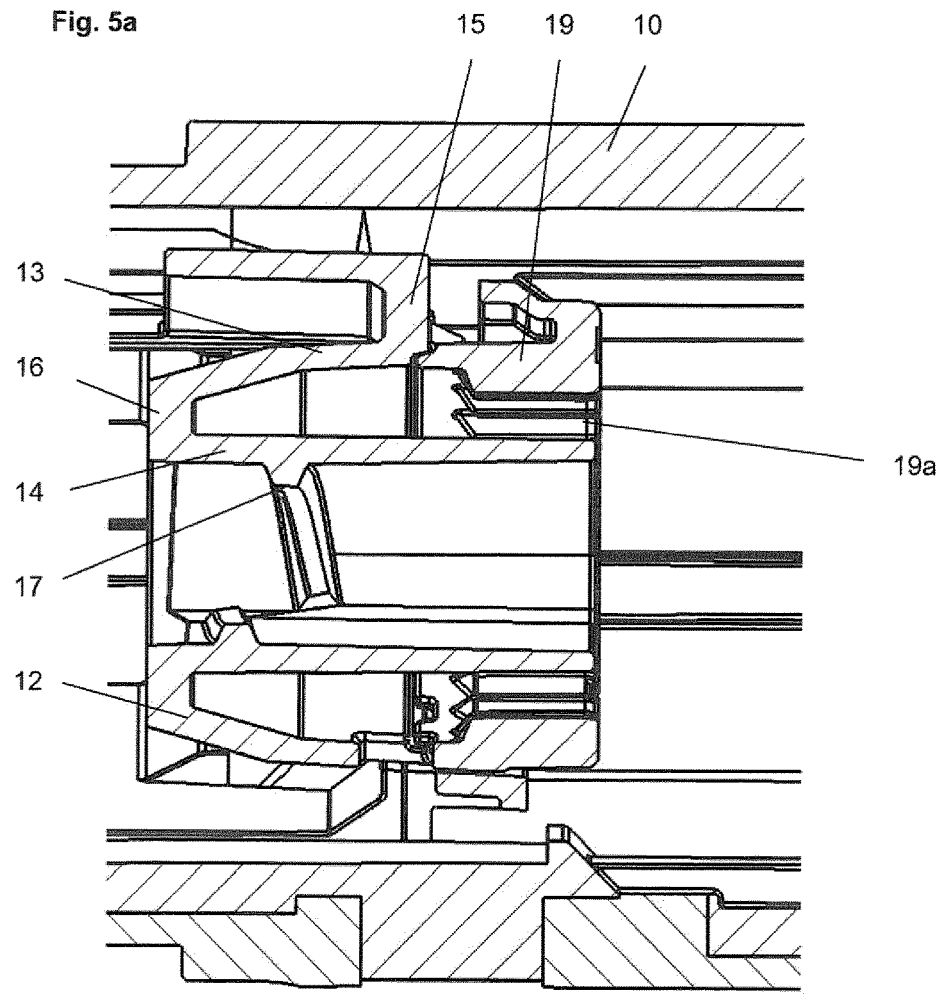
FIG. 5a shows, in a sectional view, a detail of a device according to yet another embodiment.
Figure 5B:
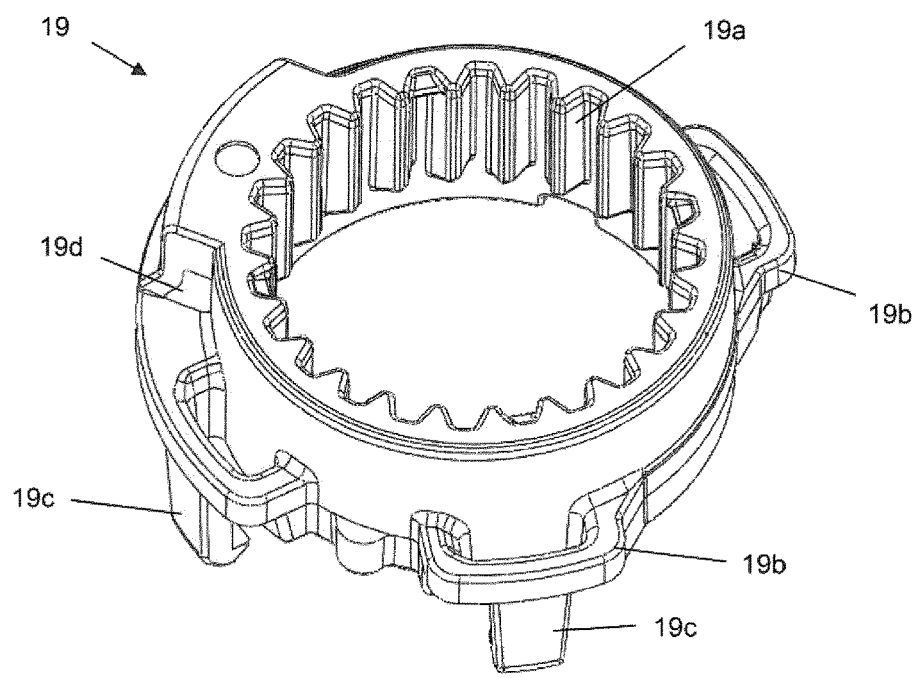

In the embodiment of FIGS. 5a and 5b, the insert 12 is partially formed as one single component part with the housing 10 and partially as a separate component part 19. The cup-shaped body 13 and the threaded tube 14 with the annular space for a compression spring are integrally formed with the housing 10 an connected thereto via arms 15, whereas the clutch feature 18 for rotationally constraining the drive sleeve 40 is a separate ring-shaped component part 19 which is axially and rotationally constrained to the housing 10. Thus, according to the embodiment of FIGS. 5a and 5b, the ring-shaped insert part 19 does not have the thread 17 as an integral part. As shown in FIG. 5b in more detail, the ring-shaped insert part 19 comprises axially orientated splines 19a on an inner surface to rotationally restrain the drive sleeve 40. The ring-shaped insert part 19 further comprises arms or splines 19b on its outer surface for rotational retention within the housing 10. Further, several hook-like arms 19c are provided to form a snap clip for axial retention of the ring-shaped insert part 19 within the housing 10. The ring-shaped insert part 19 comprises a hole or pocket 19d for receiving and fixing the hook end 91 of the drive spring 90. In addition, there are features on the ring-shaped insert part 19 that bias the insert parts 12, 19 axially and rotationally to remove free play.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert 12 of housing 10. The lead screw 30 is an elongate member with an outer thread engaging the corresponding thread of the insert 12 of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

Figure 3A:
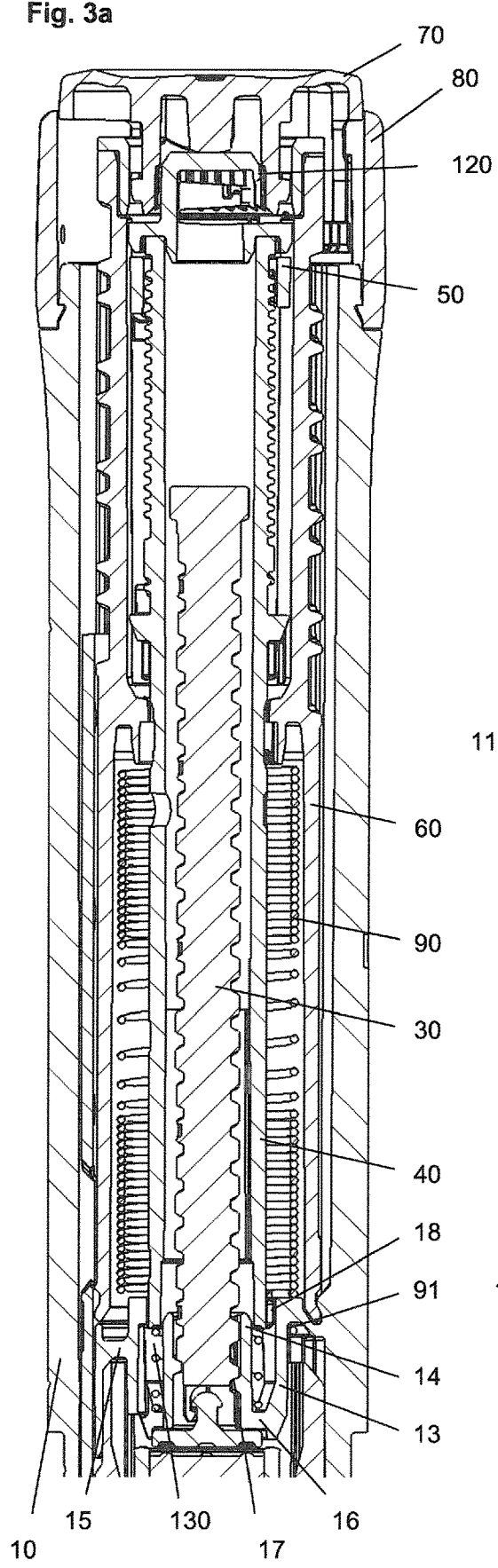
FIG. 3a shows a sectional view of the proximal end of the device of FIG. 1 in a dose setting state.

A splined tooth interface 18 with the insert 12 prevents rotation of the drive sleeve 40 during dose setting. This interface comprises a ring of radially extending outer teeth 41 at the distal end of drive sleeve 40 and corresponding radially extending inner teeth 18 of the housing component 10 (insert 12). When the button 70 is pressed (FIG. 3b), these drive sleeve to housing insert spline teeth are disengaged allowing the drive sleeve 40 to rotate relative to the insert and, thus, to housing 10. Clutch spring 130 biases the drive sleeve 40 into a position engaging with its teeth 41 the teeth 18 of the insert (FIG. 3a). A further splined tooth interface with the number sleeve 60 is not engaged during dialling, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialling only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament or drug in the cartridge 100.

The dose indicator or number sleeve 60 is a tubular element. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in the Figures comprises a number sleeve lower 60*a* which is rigidly fixed to a number sleeve upper 60*b* during assembly to form the number sleeve 60. Number sleeve lower 60*a* and number sleeve upper 60*b* are separate components only to simplify number sleeve 60 mould tooling and assembly. As an alternative, the number sleeve 60 may be a unitary component. The number sleeve 60 is constrained to the housing 10 by snap engagement to allow rotation but not translation. The number sleeve 60 comprises an annular recess or groove near its distal end which engages a corresponding bead on an inner surface of the housing 10. The number sleeve lower 60*a* is marked with a sequence of numbers, which are visible through the gauge element 110 and the openings 11*a*, 11*b* in the housing 10, to denote the dialled dose of medicament.

Further, the number sleeve lower 60*a* has a portion with an outer thread engaging the gauge element 110. End stops are provided at the opposite ends of thread to limit relative movement with respect to the gauge element 110.

Clutch features which have the form of a ring of splines are provided inwardly directed on number sleeve upper 60*b* for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline. Further, number sleeve lower 60*a* comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60*b*. Thus, it is also splined via splines to the number sleeve upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialled. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end by a hook 91 to the insert 12 and, thus, to the housing 10 and at the other end to the number sleeve 60. The torsion spring 90 is located inside the number sleeve 60 and surrounds a distal portion of the drive sleeve 40. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60*a*. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface.

The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIGS. 1 and 3*a*, the number sleeve 60 is positioned against its zero dose abutment with the gauge element 110 and the button 70 is not depressed. Dose marking '0' on the number sleeve 60 is visible through the window 11*b* of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges either side of the window area which cover the numbers printed on the number sleeve 60 adjacent to the dialled dose to ensure only the set dose number is made visible to the user.

A specific feature of this embodiment is the inclusion of a visual feedback feature in addition to the discrete dose number display typical on devices of this type. The distal end of the gauge element 110 creates a sliding scale through the small window 11*a* in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect or decrement any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

Figure 3B:
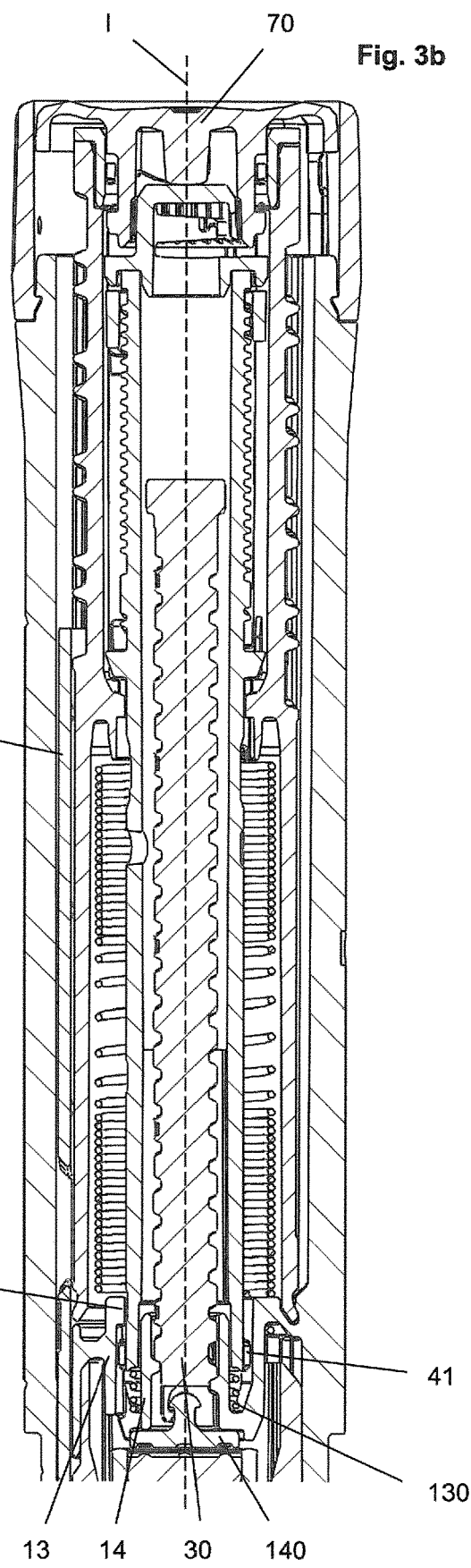
FIG. 3b shows a sectional view of the proximal end of the device of FIG. 1 in a dose dispensing state.

With the mechanism in a state in which a dose has been selected, the user is able to activate the mechanism to commence delivery of a dose. Delivery of a dose is initiated by the user depressing the button 70 axially in the distal direction (FIG. 3b).

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface 18, 41 between the drive sleeve 40 and the housing insert 12 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialled back to, or away from, the zero position.

The drug delivery device discussed above is configured to deselect or decrement any number of dosage increments of a dose which has been set previously by incrementing the mechanism. The mechanism as disclosed above utilizes overhauling of a ratchet to decrease the set dose. This ratchet has to be able to withstand the continuously increasing torque exerted by the spring which increases with the size of the set dose, i.e. with the number of unit increments the dose comprises. Consequently, overhauling the ratchet may require significant force and/or generate significant noise.

In the following text, several embodiments are disclosed for ratchet or ratchet-type mechanisms which permit incrementing and decrementing rotations, the mechanisms being able to withstand the drive torque exerted by the spring and being decrementable easily, i.e. without considerable effort. The noise associated with the decrementing operation may be reduced. Preferably, the force required for incrementing and decrementing the mechanism may be tuned individually. These mechanisms can be used to substitute the ratchet mechanism discussed above. However, as is immediately apparent for a person of skill in the art, these mechanisms are not only applicable in the drug delivery device described above but can also be used in other drug delivery devices or even in systems which are not designed to deliver drugs.

Instead of addressing the features in a general way as was done in the introductory section, in the following the features are addressed by using the more specific designations of the device discussed above. However, it should be noted that the features of the exemplary embodiments do apply also to the more general concepts disclosed above and vice versa. In the following, for some of the components of the embodiments, it is specified to which of the more general terms they correspond: The movable member corresponds to the dose indicator or number sleeve 60 or an element rigidly coupled thereto rotationally and, preferably, axially. The release member corresponds to the button 70 and/or the dose selector 80 or an element rigidly coupled thereto rotationally and, preferably, axially. The driven member corresponds to the drive sleeve 40. The energy storage member corresponds to the drive spring 90. The decrementing configuration of the mechanisms discussed below is when it is allowed to set or select (increment) and correct or deselect (decrement) a dose of drug. The driving configuration is the configuration where the number sleeve is allowed to rotate freely in order to release the energy stored in the drive spring in order to dispense the set dose. Particularly, in the driving configuration, the number sleeve and the drive sleeve are coupled such that rotation of the number sleeve is transferred to the drive sleeve. However, the enumeration above should not be understood as reciting the corresponding elements for all elements discussed in the introductory section. Thus, referrals to the more specific features in the exemplary embodiments should also be understood to refer to the more general features of the introductory section and vice versa.

Further, if a component has to be rotationally locked with respect to the housing in the decrementing configuration, a component which is permanently rotationally locked to the housing or only temporarily, e.g. in the decrementing configuration but not in the driving configuration, can be used as a counterpart for the component to achieve the rotational locking. For the latter, the drive sleeve 40 qualifies for example. However, a permanently static component could be used as well for this purpose as well as another component which is rotatable in the driving configuration.

When in the present disclosure it is referred to an "axial", "angular", "circumferential", or "radial" direction, the axis with respect to which these directions are specified may be an axis of the respective component or member, an axis of the housing, particularly a main longitudinal axis of the housing, the rotation axis around which the components or members rotate, and/or an axis of the drug delivery device, particularly the main longitudinal axis of the device. The axis may be oriented such that it extends through the proximal end and/or distal end of the device. Particularly, the proximal or distal direction may be parallel to and/or along the axis.

The housing is expediently static such that, if a component rotates, it always rotates relative to the housing. The members may be arranged such that they rotate about a common rotation axis. The rotation axis may extend through the respective member.

An exemplary embodiment of an incrementing and decrementing mechanism or assembly is described below with reference to FIGS. 6 through 9.

Figure 6:
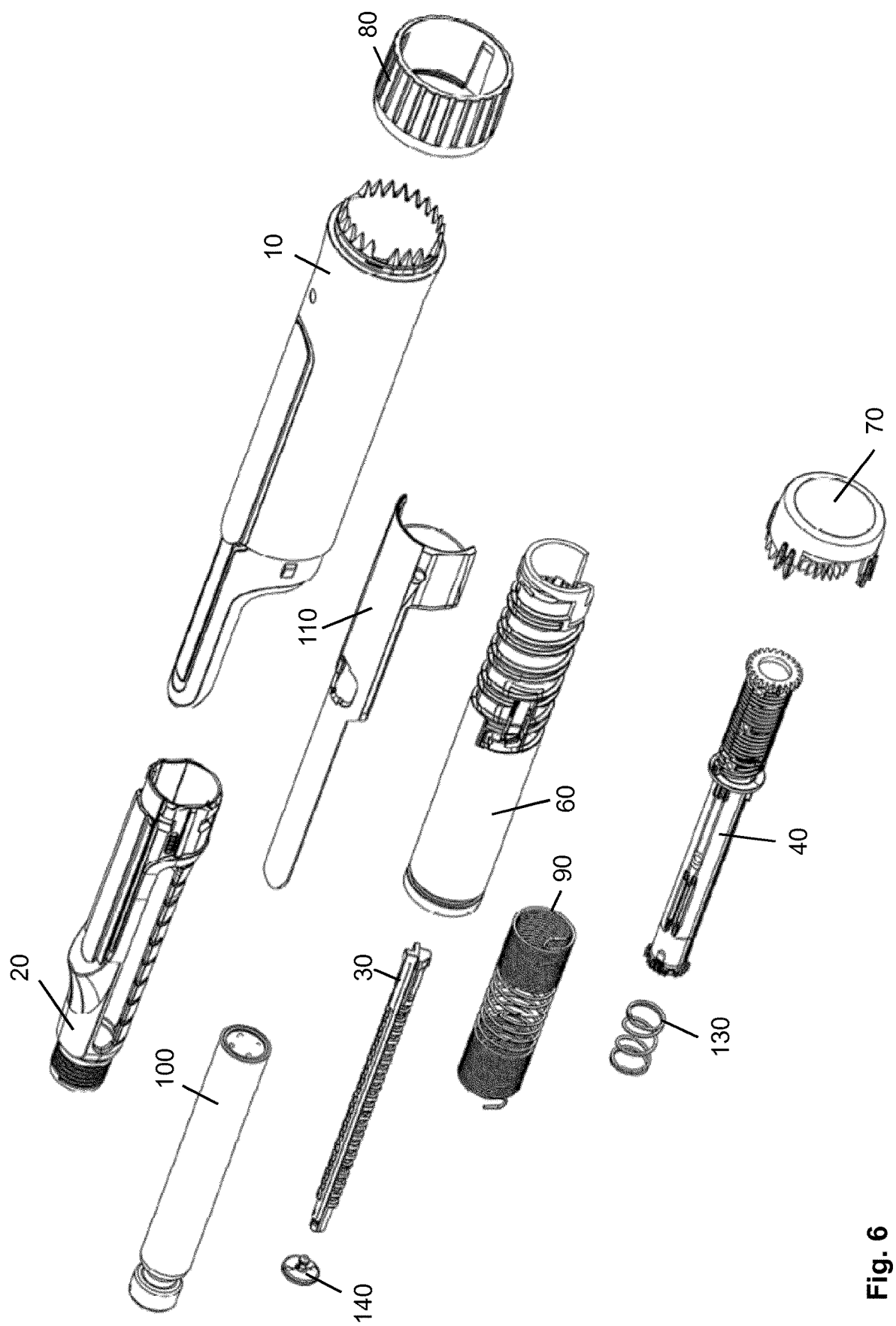
FIG. 6 shows parts of a drug delivery device which comprises a first embodiment of an incrementing and decrementing mechanism in a perspective view.
Figure 7:
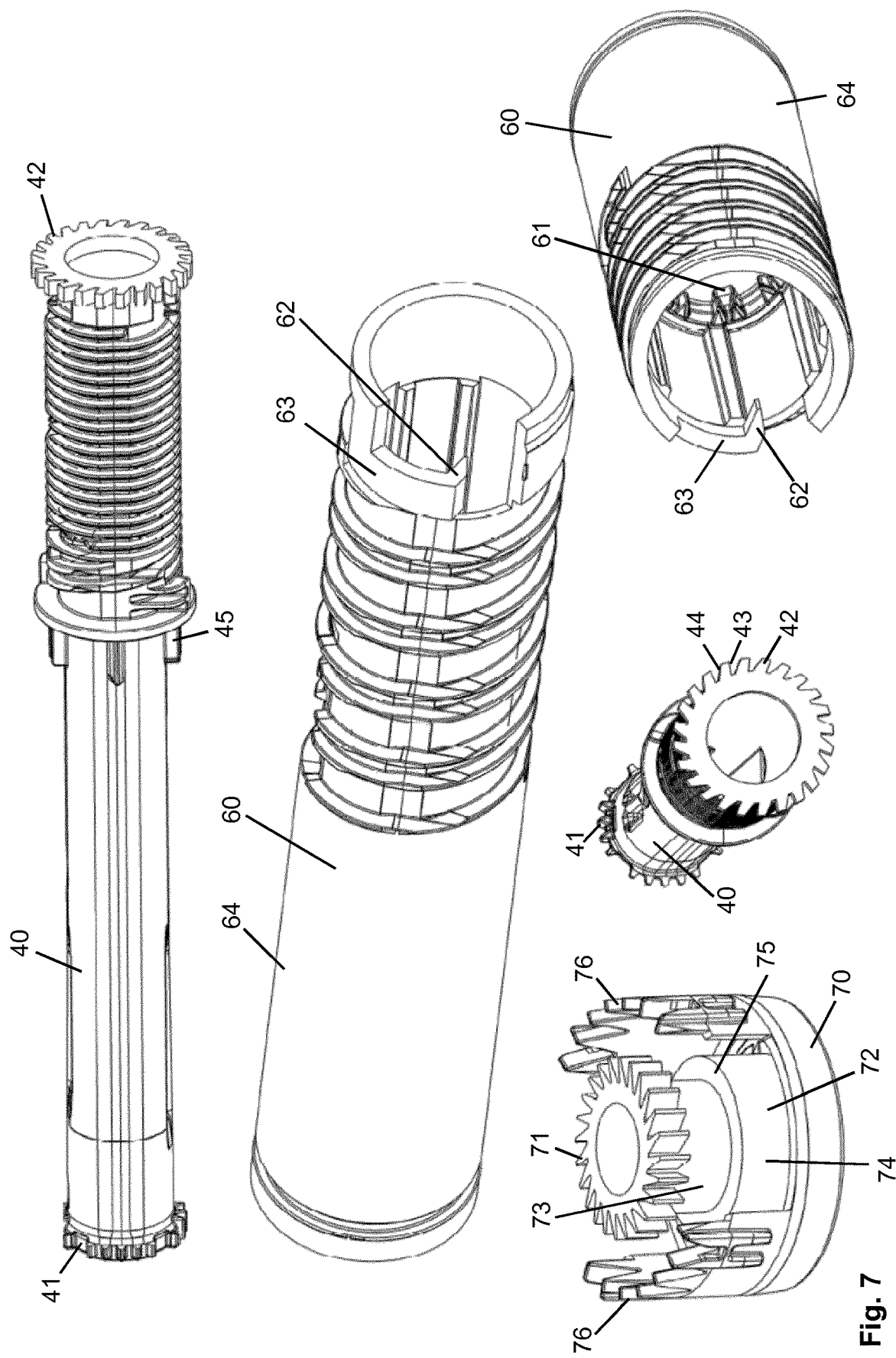
FIG. 7 shows components of the device of FIG. 6 which are involved in the incrementing and decrementing mechanism according to this embodiment in various views.

FIG. 6 shows the parts of a drug delivery device which implements the mechanism according to this embodiment in a perspective view. The device essentially corresponds to the device described in conjunction with FIGS. 1 through 5, which is slightly modified as explained below. The dose indicator 60 or number sleeve is depicted as a single part in FIG. 6. However, instead of being unitary, the number sleeve may also be formed of a plurality of parts as explained previously. Further, the indices on the number sleeve are not explicitly shown. Although the nut 50 is not shown in FIG. 6, it may well be present in the device. The decrementing functionality which, in the embodiment described in conjunction with FIGS. 1 through 5, is realized utilizing clutch plate 120, is realized differently in this embodiment. For this purpose, some of the components have been modified. Further, clutch plate 120 is not present in this embodiment. FIG. 7 shows the components of the device of FIG. 6 which have been modified for the embodiment of the incrementing and decrementing mechanism in various views. Components which participate in the ratchet-type mechanism and have been modified are: drive sleeve 40, number sleeve 60, and button 70.

The drive sleeve 40 is provided with one or a plurality of block features or ratchet features 42, e.g. teeth. The ratchet features 42 are oriented in the radial direction, particularly in the radial outward direction. The ratchet features 42 are uniformly distributed in the circumferential or angular direction. Preferably, all ratchet features are designed alike. The ratchet features 42 are rigid and rigidly connected to the drive sleeve 40 or formed integrally with the drive sleeve 40. The ratchet features 42 are designed to form a unidirectional radial ratchet interface which, when established, permits relative rotational movement only in one rotational direction. For doing so, the respective ratchet feature may, for example, comprise asymmetric angular side faces. For example, the respective ratchet feature may comprise a steep side face 43 and/or an inclined side face 44 which may be less steep than the steep side face with respect to the radial direction. Consequently, a radially deflectable feature which rests in a particular ratchet pocket which is formed between two adjacent ratchet features 42 can, preferably, only be moved in one direction out of the ratchet pocket, e.g. along the inclined side face, into the adjacent ratchet pocket. In this way, a unidirectional ratchet interface is realized. The ratchet features 42 are expediently formed in a proximal end section or at the proximal end of the drive sleeve. The ratchet features 42 expediently define the unit increment of the mechanism or the minimum dose which can be set to be delivered from the device incorporating the mechanism. The drive sleeve 40 may comprise more than 10 or more than 20 ratchet features 42.

Furthermore, the drive sleeve 40 comprises at least one or a plurality of spline features 45. The respective spline feature extends axially and is designed to form a splined interface, expediently with corresponding spline features 61 provided on the number sleeve 60, in the dose delivery or driving configuration of the mechanism. In this way, the number sleeve 60 and the drive sleeve 40 may be rotationally locked to one another in the driving configuration, whereas, in the setting configuration, which is also designated as decrementing configuration herein, relative rotation between the number sleeve 60 and the drive sleeve 40 is allowed.

The button 70 comprises one or a plurality of ratchet features, member features or release features 71. The features are oriented in the radial direction, particularly in the radial outward direction. The features 71 protrude radially from a support 72. The support 72 may be configured as a stem or pillar-like structure arranged in the center of the button. The support 72 may protrude from a proximal inner end surface of the button 70. The features 71 may be arranged in a distal end section of the support 72. A distal end face of the support may be arranged to abut a proximal end face of the drive sleeve 40, when the parts shown in FIG. 7 are assembled. Axially offset from the ratchet features 71, particularly in the proximal direction, is a region 73. In the axial direction, particularly in the proximal direction, this region 73 is followed by another region 74 of the support 72. The radial width of region 74 may be greater than the one of region 73. Region 73 is preferably free of radially extending protrusions or ratchet features. Region 73 may be configured to allow smooth and/or unhindered rotational movement of a feature relative to the button 70 when that feature is guided in the region 73. The release features 71 and the region 73 may be configured to allow a transition of a feature from a ratchet pocket formed between adjacent ratchet features 71 into the region 73 and vice versa. For doing so, a transition between the bottom of a ratchet pocket, for example the radial end wall delimiting the pocket, and the region 73 may be smooth in order to allow a transition from a ratchet pocket into the region 73 and vice versa. The step 75 provided between regions 73 and 74 of the support 72 may form an axial stop for the feature when the feature is relocated from the ratchet pocket into the region 73. The feature may be in contact with the support 72 in region 73 or arranged at a radial distance with respect to the region 73 when the axial positions of the feature and the region 73 overlap. The axial extension of region 73 is expediently greater than the axial extension of the region where the features 71 are applied and/or greater than the axial extension of the features 71.

The button 70 further comprises spline features or spline teeth 76. These features are designed to interact with corresponding teeth on the housing or body 10 in order to rotationally lock the button and/or the dose selector 80 when the mechanism is switched from its decrementing configuration to the driving or dispensing configuration when the energy of the spring is released in order to drive the drive sleeve 40 as disclosed further above.

The features 71 and the ratchet features 42 are adjusted to one another. Although it is discussed below that, for certain purposes, it may be sufficient to have a reduced number of features 71 it is preferred that the number of features 71 equals the number of ratchet features 42. Specifically, features 71 and 42 are adjusted such that when the features 71 and 42 are arranged axially with respect to one another such that the features 71 are arranged subsequent in the axial direction to the features 42 and when, in this arrangement, the features 71 and 42 are aligned with respect to another in the angular direction, pockets, particularly all pockets formed between two adjacent features 71 and 42, respectively, are aligned. This enables that a feature such as a locking feature 62 of the number sleeve 60 which is described in more detail below can at the same time engage features 71 and 42. Particularly, feature 62 can be arranged in a pocket defined by features 71 and a pocket defined by features 42 at the same time. With respect to the inclination of the side faces of the respective features, the features 42 and 71 may be formed alike. The same holds with respect to the angular positions. Consequently pockets are formed having the same or at least similar widths in regions where the pockets defined by features 42 and 71 overlap, particularly when seen along the axial direction.

As compared to the radial extension of features 42, the radial extension of features 71 is greater. Particularly, features 71 may protrude further in the radial direction than features 42. It is preferred that at least the radial end of features 71 is arranged further away from an axis, which may be defined by the rotation axis around which associated components rotate, than the radial end of features 42. This facilitates the function of features 71 as release features as will be explained further below. The length of the features 71 may be two-times the length of the features 42 or more.

The number sleeve 60 comprises a locking feature 62. It should be appreciated that, instead of a single locking feature as illustrated, a plurality of locking features 62 could be provided. In case a plurality of locking features is provided, they are expediently uniformly distributed in the angular or circumferential direction over the number sleeve 60. The locking feature 62 is flexibly, preferably resiliently, connected to the remainder of the number sleeve 60. The locking feature 62 may be flexibly displaceable relative to a number sleeve body 64. The locking feature 62 may be formed unitarily with the number sleeve body and/or may be connected to the number sleeve body via a flexible arm 63, which, particularly, extends in the angular direction. The locking feature 62 extends in the radial direction, particularly in the radial inward direction, e.g. from the flexible arm 63, such as in a region near or at a free end of the arm 63. Consequently, the locking feature 62 can be displaced resiliently or elastically, inwardly and/or outwardly, in the radial direction relative to the number sleeve body 64. The locking feature 62 may be provided in the proximal end region of the number sleeve 60. The axial extension of the locking feature is expediently greater than the axial extension of the ratchet features 42 and/or the axial extension of the features 71. This facilitates simultaneous engagement of aligned ratchet pockets defined by features 42 and 71 by the same locking feature 62. As the locking feature 62 is radially and resiliently deflectable it can be moved out of one ratchet pocket and re-engage the subsequent ratchet pocket on account of its resiliency easily. The axial extension of the region 73 is expediently at least equal to or preferably greater than the axial extension of the locking feature 62. A free rotational movement of the locking feature within the region 73 in the driving configuration of the mechanism is facilitated in this way. The features 71 preferably protrude with respect to the features 42 by a length which is greater than or equal to one of the following values: radial extension of the locking feature 62, radial extension of the features 42.

Figure 8:
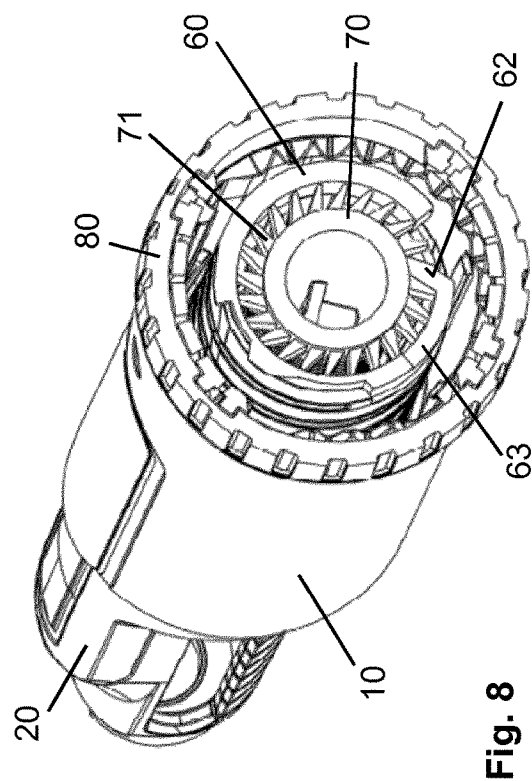
FIG. 8 shows a perspective and partial sectional view on the device of FIG. 6 in an assembled state.

As explained further above, in the incrementing and decrementing configuration, the drive sleeve 40 is rotationally locked with respect to the housing 10, whereas the button 70 is rotatable in both rotational directions. Consequently, the proposed mechanism comprises a fixed ratchet, realized by ratchet features 42 and a rotatable ratchet realized by means of features 71. FIG. 8 shows a perspective and partial sectional view on the device of FIG. 6, where some components of the incrementing and decremented mechanism are illustrated in an assembled state. As they are arranged beneath the features 71, ratchet features 42 on the drive sleeve 40 are not visible in FIG. 8.

Figure 9:
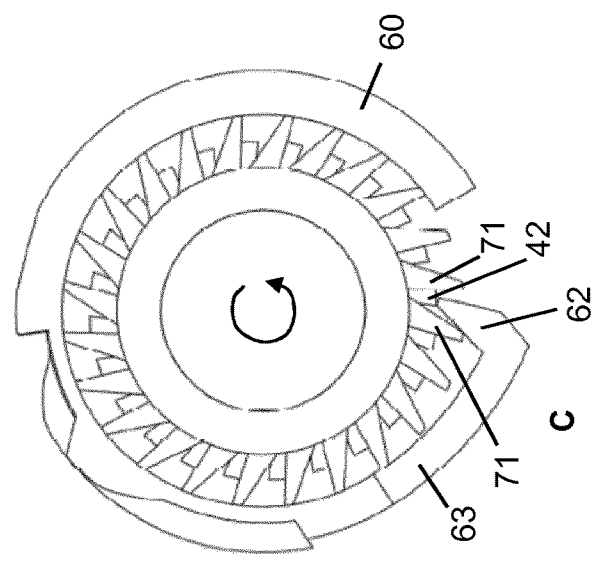
FIG. 9 shows in representations A through C the incrementing and decrementing mechanism according to this embodiment in different situations.
Figure 9:
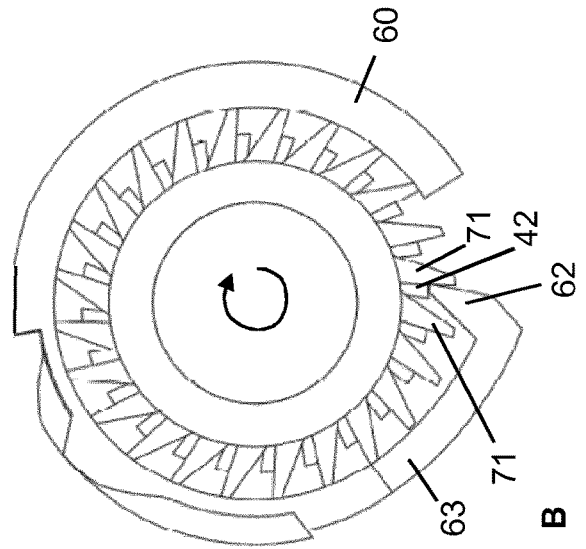
Figure 9:
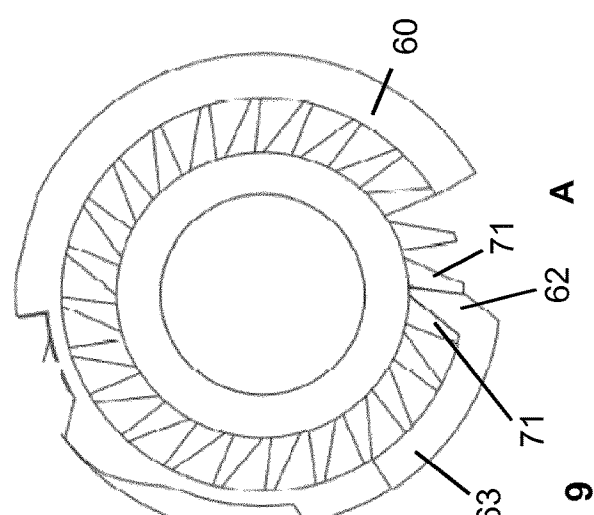

In the following, incrementing and decrementing operation of the proposed mechanism is described in conjunction with FIG. 9. FIG. 9 shows in representations A through C the incrementing and decrementing mechanism in different situations. In FIG. 9A, the mechanism is in a rest position, which may, for example be the situation when a zero dose or a non-zero dose has been set and the dispense operation has not yet been triggered by pressing the button 70 in the axial direction. FIG. 9B illustrates the incrementing operation of the mechanism, that is to say the operation to increase the dose. FIG. 9C illustrates the decrementing operation of the mechanism, i.e. how the dose is decreased.

When, starting from the situation shown in FIG. 9A, the features 71 are rotated in an incrementing direction by rotating the button 70, for example in the clockwise direction, one of the features 71 abuts the locking feature and carries the locking feature 62 with it as is depicted in FIG. 9*b*. In the incrementing direction, the unidirectional ratchet realized by features 42 allows relative rotation between the locking feature 62 and the ratchet features 42. Consequently, the locking feature 62 is displaced radially outwardly as it slides along the inclined side face of the feature 42 delimiting the ratchet pocket in the incrementing direction and again inwardly, e.g. on account of the elastic restoring force, into the next ratchet pocket of the unidirectional ratchet realized by ratchet features 42 while being driven by the feature 71 throughout the rotation. The locking feature 62 stays in the same pocket defined by features 71. When the button 70 is rotated in the incrementing direction, the locking feature 62 is radially displaced out of the ratchet pocket of the unidirectional ratchet but, on account of the greater radial length, stays in contact with one of the features 71 expediently the one delimiting the ratchet pocket in the decrementing direction. While passing from one ratchet pocket into the next ratchet pocket, the locking feature 62 may contact and slide along the radial end of the feature 42 separating the two ratchet pockets as shown in FIG. 9*b*. When the next ratchet pocket of the unidirectional ratchet is reached, on account of its resiliency, the locking feature automatically re-engages with the unidirectional ratchet, expediently by a radial inward movement, and the mechanism has been incremented by one unit increment as the number sleeve 60 has been rotated relative to the ratchet features 42 in the incrementing direction. The increased drive torque in the drive spring 90 is still reacted by the drive sleeve 40 and the unidirectional ratchet. After the incrementing movement the mechanisms is, again, in the situation shown in FIG. 9A.

When, starting from the situation in FIG. 9A, the mechanism has already been incremented and the features 71 are rotated in a decrementing direction, e.g. the anti-clockwise direction, by rotating the button 70, one of the features 71 abuts the locking feature 62 and during continued rotation in the decrementing direction slides along the feature 62 which, on account of its resiliency is displaced radially, in particular radial outwardly. The locking feature 62, eventually, leaves the ratchet pocket of the unidirectional ratchet, as the features 71 have a greater radial extension than the features 42. FIG. 9C shows a situation after the locking feature has been disengaged from of the unidirectional ratchet. As long as the button 70 and along with it the feature 71 which moved the locking feature radially is kept in the position shown in FIG. 9C, which it may be by the user, the locking feature 62 is kept disengaged from the unidirectional ratchet. In the situation depicted in FIG. 9C, the locking feature contacts the radial end of the feature 42. Consequently the locking feature and the unidirectional ratchet have just disengaged. As the drive torque exerted by drive spring 90 tends to drive the number sleeve 60 and, together with it, the locking feature 62 in the decrementing or driving direction, the situation depicted in FIG. 9C is only present temporarily. From this situation, the drive torque rotates number sleeve and the locking feature into the decrementing direction relative to the release member 71 until the locking feature abuts with the subsequent feature 71, in particular that feature delimiting the pocket in the decrementing direction. This feature blocks further rotational movement of the locking feature 62 relative to the features 71 and button 70. When the locking feature 62 abuts the feature 71, the drive torque is transferred to the user as long as the user reacts the torque.

When the torque is no longer reacted, the button 70 can be rotated again and, the locking feature is allowed to engage the next ratchet pocket of the unidirectional ratchet formed by features 42. It will do so on account of its resiliency and move radial inward in order to re-engage with the unidirectional ratchet. Accordingly, features 71 do serve as release features for releasing the unidirectional locking interface which is formed by the ratchet features 42 in cooperation with the locking feature 62 by radially displacing the locking feature 62 outwardly in order to release the rotational lock in the decrementing direction temporarily. When the gap between the feature 71 which delimits the ratchet pocket in the decrementing direction and the locking feature 62 which is present in FIG. 9C has been closed on account of the torque exerted on the number sleeve 60 by the drive spring, the drive torque exerted by the drive spring assists the decrementing movement until the subsequent ratchet pocket of the unidirectional ratchet is engaged. In this way, the mechanism can be decremented by one unit. The mechanism can be decremented unit increment by unit increment. After the locking feature 62 has re-engaged with the unidirectional ratchet, the mechanism is again in the situation depicted in FIG. 9A. While the locking feature 62 is disengaged from the features 42, the user could actively rotate the number sleeve 70 via the interaction between number sleeve and button 70 in the decrementing direction by an arbitrary number of increments, provided the locking feature 62 is maintained in abutment with the feature 71. This may, for example be achieved by a radial stop which abuts the locking feature 62 or the arm 63 radially and is arranged on the opposite side of the feature 71. However, using the drive torque to decrement the mechanism unit by unit as disclosed above is also advantageous, of course.

It should be noted, that in the situations depicted in FIGS. 9A through 9C, the locking feature 62 is at all times arranged between the same two features 71 that is to say within the same pocket defined by features 71. For the incrementing and decrementing functionality the number of features 71 could be one, or less than the number of features 42, or equal to the number of features 42. Thus, it would also be possible to construct a mechanism, which allows to decrement by more than one unit increment. However, as will be apparent from the description below, it is advantageous to have the same number of features 42 and 71.

When the mechanism is switched from the decrementing configuration which permits incrementing and decrementing rotation and is shown in FIG. 9, for example, into the driving configuration by pressing on the button 70 in the distal direction, the unidirectional interface which prevented rotation of the number sleeve 60 in the decrementing direction is released by relative axial movement between the locking feature 62 and the ratchet features 42. Specifically, it is the drive sleeve 40 which is distally displaced relative to the number sleeve such that the locking feature 62 disengages from the unidirectional ratchet formed by ratchet features 42. Also, the button 70 is displaced relative to the number sleeve 60 in the distal direction such that the locking feature 62 also disengages from features 71 and, particularly, is able to rotate freely. The distal movement of the drive sleeve 40 is used to rotationally lock the drive sleeve and the number sleeve 60 to one another such that they co-rotate with each other. The locking feature 62 can now rotate in the region 73 of the button 70 which enables free rotational movement of the number sleeve 60 and, together with it, the drive sleeve 40 which is now in the driving configuration in order to dispense the dose which has been previously set.

Once the user releases the button 70, the button 70 is displaced in the proximal direction. This displacement is achieved by the clutch spring 130 which exerts a force in the proximal direction on the drive sleeve 40 which is transferred to the button 70 as the drive sleeve 40 abuts the button. This permits re-engagement of the unidirectional ratchet realized by features 42 and the locking feature 62. Also, as the features 71 are preferably matched with respect to number and/or angular configuration to the features 42, the locking feature 62 also engages, again, with features 71. However, the features 71 between which the locking feature is now arranged can be different than the ones before the dose dispensing operation has been commenced. If the number of features 71 is less than the number of features 42 then the relative angular position between the locking feature 62 and the features 71 may not be suitable for an incrementing movement. The button 70 may be rotated into the incrementing or the decrementing direction until the locking feature 62 engages, again, with features 71. The mechanism has now returned to the situation depicted in FIG. 9A.

It should be noted, that for the operation of the incrementing and decrementing mechanism, it is sufficient that the unidirectional ratchet is rotationally fixed relative to the housing in the decrementing configuration of the mechanism. Consequently, instead of with the drive sleeve 40, a unidirectional ratchet interface with another component which is permanently secured to or formed by the housing 10 could be realized. However, integrating the unidirectional ratchet to a component which, like drive sleeve 40, is rotationally constrained with respect to the housing 10 in the incrementing configuration and is driven in the driving configuration by means of the drive spring together with the number sleeve enables a highly integrated way of implementing the mechanism.

In slightly different words, this embodiment relates to a double ratchet which controls both the incrementing and decrementing of the dose. Ideally this is symmetric in torsional force and increment size for the end user, however this is challenging due to the variable loading options (via variable dose size) and the torsional drive spring which is always driving to decrement the dose. Another challenge is in preventing unintended decrement or slippage of components under the action of the drive spring in all use scenarios, which, if not prevented, would result in inaccurate dosing. The basis of this embodiment is a double radial ratchet. One ratchet is rotationally fixed at least in the decrementing configuration of the assembly, the other one is rotatable in both angular directions in the decrementing configuration.

The button/rotating ratchet component is linked to the user during decrementing so any impact noise and vibration is damped by the user's hand. It is stable in the new position until further torsional load is applied by the user which would then repeat the process. The torsional load required to decrement by a unit is tuned by adjusting the radial flexibility in the locking feature. The force required to increment the dose can be tuned by adjusting the cam angle between the fixed ratchet element face and the flexible locking feature. When the dose is dispensed by pressing axially on the button, the ratchets both disengage, providing rotational freedom for the drive sleeve to advance the lead screw and dispense the dose.

The independent asymmetric mechanism allows a unique, independent tuning of the forces required to both increment and decrement the dose. This is of particular benefit as the torsional drive load encountered by the ratchet elements can vary with both angular direction and dose size. By tuning both, the incrementing and the decrementing independently the user experience can be adjusted to an acceptable, optimized feel and sound, whilst minimising the risk of the slippage due to constant application of the drive torque. The present embodiment offers great design freedom and can be tuned to precisely meet the user needs. The present embodiment is also space efficient and fits within very limited space constraints. It may also be adaptable to changes with respect to different dose increments. Damping of impact forces, via the user, reduces noise and vibration when decrementing dose.

Another exemplary embodiment of an incrementing and decrementing mechanism or assembly is described below with reference to FIGS. 10 through 12.

Figure 10:
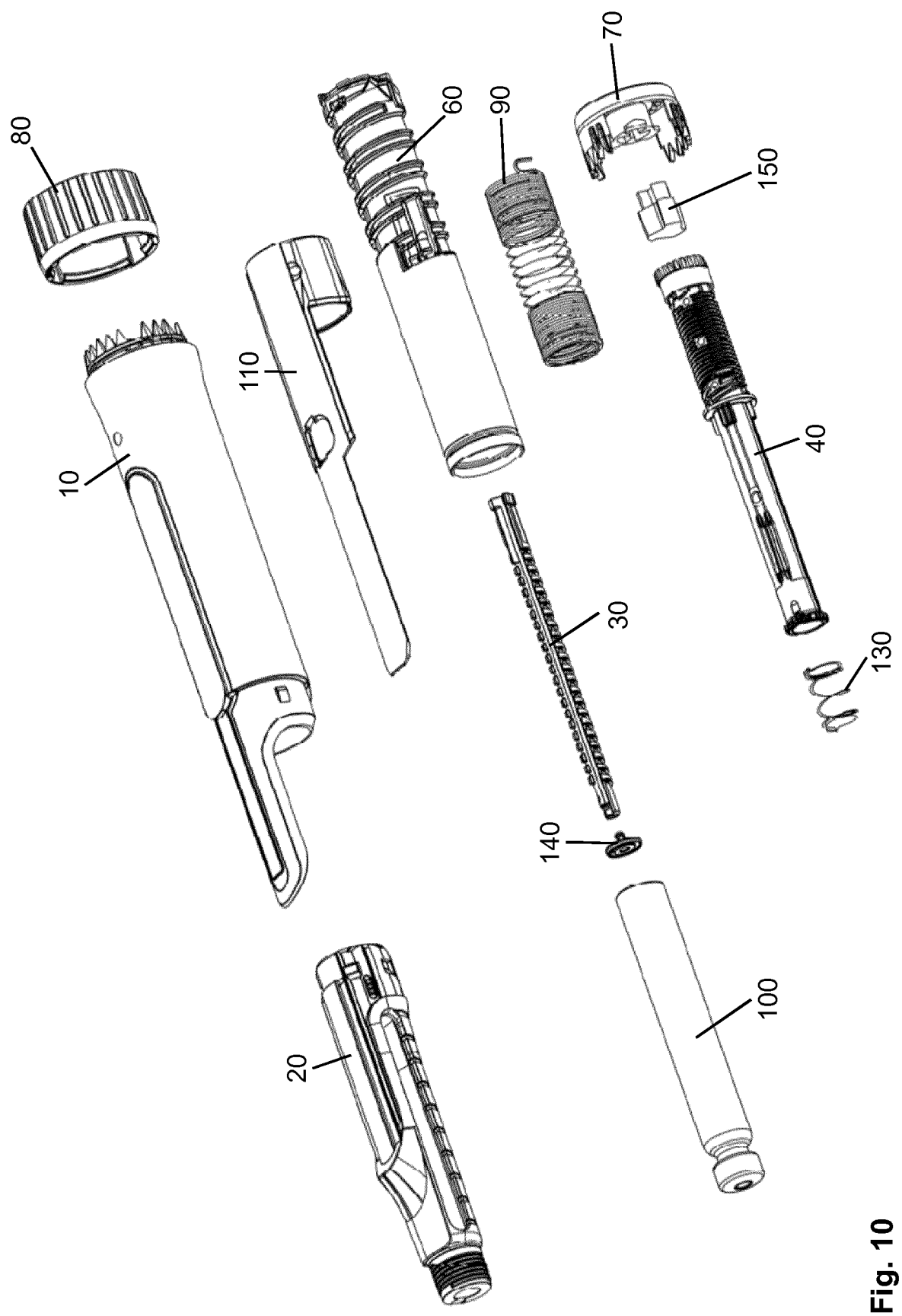
FIG. 10 shows the parts of a drug delivery device which comprises the mechanism according to another embodiment in a perspective view.

FIG. 10 shows the parts of a drug delivery device which comprises the mechanism according to this embodiment in a perspective view. The device essentially corresponds to the device described in conjunction with FIGS. 1 through 5, which is slightly modified as explained below. The dose indicator or number sleeve 60 is depicted as a single part in FIG. 10. However, instead of being unitary, the number sleeve may also be formed of a plurality of parts as explained previously. Further, the indices on the number sleeve are not explicitly shown. Although the nut 50 is not shown in FIG. 10, it may well be present in the device. The decrementing functionality which, in the embodiment described in conjunction with FIGS. 1 through 5, is realized utilizing clutch plate 120 is realized differently in this embodiment. Consequently, clutch plate 120 is not present in this embodiment. Rather, for this embodiment, some of the components have been modified and a new component has been added, i.e. a support member 150.

Figure 11:
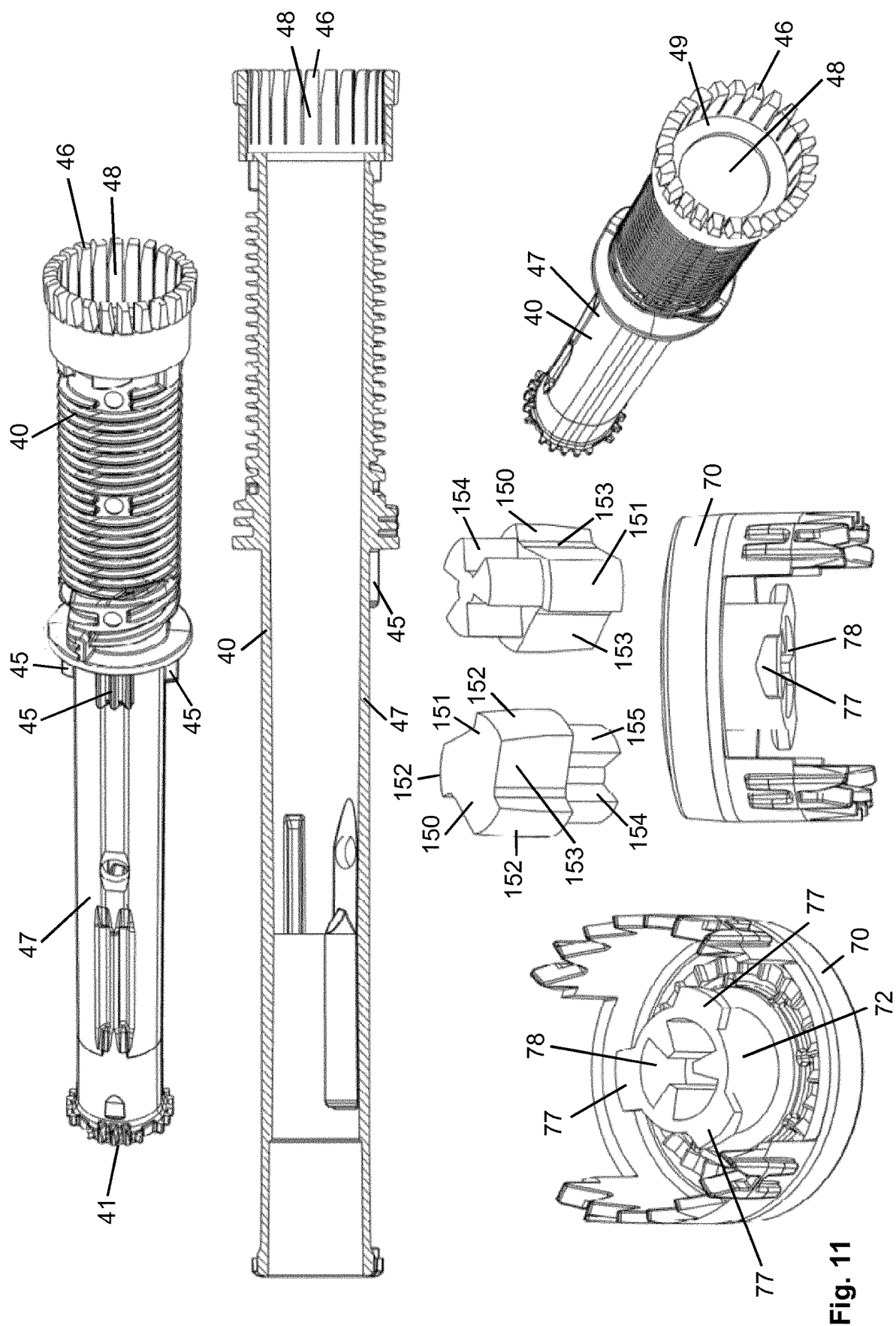
FIG. 11, on the basis of various views, shows components which are involved in the incrementing and decrementing mechanism according to this embodiment in various views.

FIG. 11, on the basis of various views, shows components of the mechanism. FIG. 11, in particular, shows components which have been modified for the present embodiment as compared to the embodiment shown in FIGS. 1 through 5 and also the additional support member 150 in various views. The components shown in FIG. 11 are described below.

The drive sleeve 40 comprises a plurality of locking features 46. The locking features 46 are arranged in a proximal section of the drive sleeve 40. The locking features are arranged and configured in a comb-like manner. The locking features 46 are axially oriented. The locking features 46 are further flexible in the radial direction. That is to say, they can be radially displaced with respect to a drive sleeve body 47. Particularly, the locking features 46 may, from the position shown in FIG. 11 be displaced radially inwardly. From an inward end position, they may, again, be displaced radially outwardly. The locking features 46 may be resilient or resiliently mounted to the drive sleeve 40. Thus, once having been radially displaced the locking features may tend to resume their original position on account of the resilient restoring force. All locking features 46 may be formed alike. The locking features 46 are uniformly distributed in the angular direction over the drive sleeve 40. The distance between two locking elements, particularly, between two faces of adjacent locking elements 46 which delimit the locking element in the same angular direction, may define the unit increment by which the number sleeve 60 can be rotated in the incrementing direction. Apart from being radially displaceable the locking features are expediently rigid. Particularly, the connection between the locking features 46 and the drive sleeve body 47 may be configured such that it can withstand significant angular or tangential forces. The locking features 46 may be stable against angular displacement under the action of the torque exerted by the drive spring 90, when the drive torque is transferred to an angular face of the locking member 46. Thus, the locking features 46 can be used to lock the number sleeve 60 against rotation in an incremented way. The locking features, in particular the angular pitch in which they are arranged, define the unit increment.

The locking features 46 define a holding space 48, where the locking features form the outer boundary of the holding space. The holding space 48 is delimited in the distal direction by a radial, step-like protrusion 49. The holding space 48 is arranged to receive at least a section of the support member 150. Protrusion 49 provides a bearing surface for the support member 150 as will be explained below.

The support member 150 comprises a support region 151. The support member 150 is designed to be received within the holding space 48 of the drive sleeve. The maximum outer diameter of the support region 151 may correspond to the inner diameter of the holding space, particularly when the locking features 46 are in their un-deflected state. The support member 150 comprises one or a plurality of support features 152. These features may be distributed uniformly in the angular direction. The support features 152 may define the maximum outer diameter of the support region 151. The support region 151 is designed to be retained, at least partly, within the holding space 48 such that the support member 150 is rotatable relative to the locking features 46. Locking features 46, of which the angular position overlaps with the angular position of a support feature 152, cannot be radially displaced easily. Rather, they are supported against radial displacement as they are contacted mechanically by a support feature 152. In the angular region between two support features 152, the support member 150 comprises a section 153 of reduced radial extension. When the support member 150 is received in the holding space, locking features which are arranged in the region of section 153 may be radially displaced, particularly in the inward direction.

Accordingly, by means of the support member 150 with the support features 152, some locking features 46 may be selectively supported against radial displacement while the non-supported locking features 46 may be displaced radially.

The support member 150 further comprises a coupler region 154. The coupler region 154 and the support region 151 may be arranged in axial succession. The axial extensions of the coupler region 154 and support region 151 may be different, e.g. the support region 151 may be of greater axial extension. Expediently, the support region 151 and the coupler region 152 are designed such that, when the support region 151 is received in the holding space 48, the coupler region 154 protrudes, expediently entirely, from the drive sleeve 40. In this way, achieving a coupling between the support member 150 and the button 70 is facilitated. The coupler region 154 is designed to couple the support member 150 rotationally to the button 70. Consequently, the support member 150 is designed to follow rotational movement of the button 70 in both rotational direction. However, the rotational coupling between the button 70 and the support member 150 is configured such that it permits a limited relative rotational movement of the button 70 relative to the support member 150, expediently in both rotational directions, before button 70 and support member 150 are locked in rotation, i.e. rotate together. The maximum angle of relative rotation which is allowed between the support member 150 and the button 70 is expediently greater than or at least equal to the rotation angle required for incrementing the mechanism by one increment or two increments. The coupler region 154 has a plurality of coupler features 155 which are provided to couple the support member 150 rotationally to the button 70.

The button 70 has one or more features 77. The features 77 are designed to interact with the number sleeve 60 or a component firmly attached thereto in order to drive rotational movement of the number sleeve 60, expediently in the incrementing direction only. If there is a plurality of features 77, the features are preferably uniformly distributed in the angular direction as depicted. The features 77 protrude radially from the support 72. The support 72 may be arranged in a central region of the button 70 and protrude in the distal direction. The button 70 further comprises a receiving section 78. This section is designed to receive the coupler region 154 of the support member. The shape of the receiving section 78 may be complementary to the one of the coupler region 154, where the receiving section is designed to allow limited relative rotation of support member and button 70 as explained above and will be further explained below. The features 77 may extend further in the radial direction than the support features 152 of the support 150.

A step is provided in the support member 150 between the support region 151 and the coupler region 154. The radial width of support region 151 may be greater than the one of coupler region 154. The step may provide a bearing surface for the button 70, particularly for the distal face of the support 72.

Figure 12:
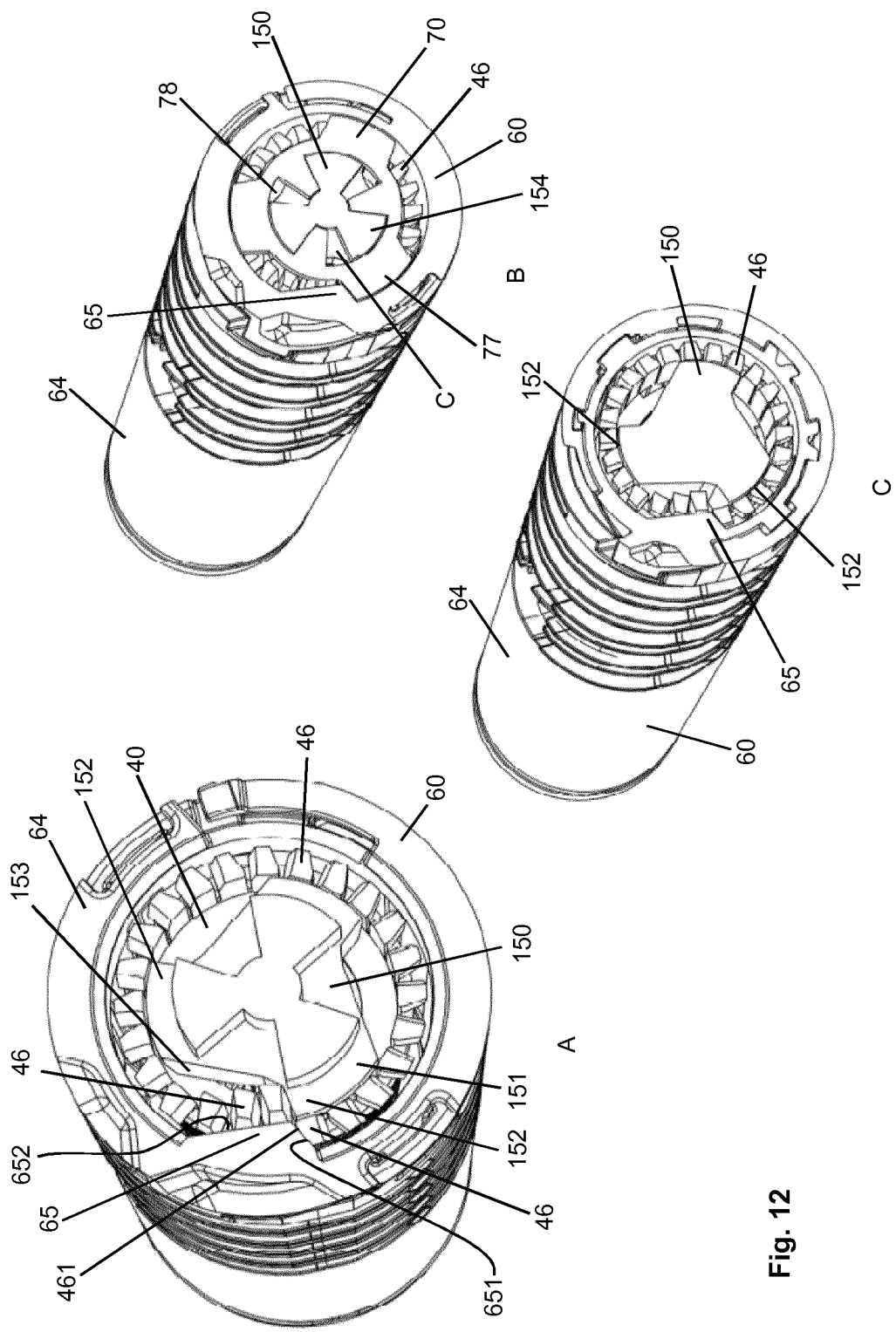
FIG. 12 shows components of the incrementing and decrementing mechanism according to this embodiment in an assembled state in different situations and in different views in representations A through C.

FIG. 12 shows components of the mechanism in an assembled state in different situations and in different views in FIGS. 12A through 12C. Therein, the support member 150 and, particularly, its support region 151 is arranged between the locking features 46. Further, in FIG. 12B, the button 70, in particular the features 77 thereof, are shown and the receiving section 78, in which the button 70 is coupled to the support member 150. FIGS. 12A and 12C do not show the button 70 for the purpose of better illustration. It is, however, immediately apparent from FIG. 12B that the feature 77 does radially overlap with the locking features 46. Particularly, the features 77 may protrude radially further than the support member and/or protrude radially over the locking features 46.

In addition to the components discussed in conjunction with FIG. 11, FIG. 12 shows the number sleeve 60. The drive sleeve 40 with the locking features 46 is received within the number sleeve 60. The number sleeve 60 has a block feature or feature 65. The feature 65 protrudes from the number sleeve body 64, particularly in the inward direction. The feature 65 is arranged to radially displace one or more locking features 46, in particular in the inward direction. Preferably, the feature 65 is always in contact with one or more locking features 46. The feature 65 overlaps, as seen in the angular direction, with section 153 of the support member 150 such that the locking features 46 can be radially deflected into the recess defined by the section 153. In the angular direction, feature 65 is delimited by two surfaces, a first surface 651 and a second surface 652. The first surface 651 delimits the feature 65 preferably in the decrementing direction, e.g. the anti-clockwise direction. The second surface 652 delimits the feature preferably in the incrementing direction. The surfaces 651 and 652 may be inclined, particularly with respect to the radial direction. The angles of inclination may be different for the surfaces 651 and 652. Surface 652 may be longer than surface 651. The surface 651 is expediently arranged to mechanically cooperate with an angular surface 461 of one, expediently only one, locking feature 46. Surface 652 may cooperate with a plurality of locking features and, particularly, retain them in a radially displaced or deflected state. Surface 652 may be arranged to cooperate with radially facing surfaces of the locking features 46. Surface 651 is expediently arranged to cooperate with angularly or tangentially facing surfaces of the locking features 46. The geometry of each locking feature 46 is expediently designed such that a force applied tangentially around the main axis of the device in the direction of the drive spring torque to the feature, e.g. to its tip, will cause the feature to displace radially out of the rotational path of the rigid feature 65 on the number sleeve 60.

In the situation shown in FIG. 12A, the feature 65 abuts one locking feature 46 as seen in the angular direction. This locking feature 46 is radially supported by support feature 152. Consequently, although the contact interface between the feature 65 and the locking feature 46 which it abuts is configured such that, if the feature 65 were rotated in the decrementing direction this rotation would result in a radial displacement of the locking feature 46, particularly in the inward direction, this displacement is prevented by the support feature 152. In the situation depicted in FIG. 12A, a non-zero dose may have been set already. The number sleeve 60 is under the influence of the torque of the drive spring 90. Consequently, the support member 150 and that locking feature 46 which the feature 65 abuts cooperate to prevent or block rotation of the number sleeve 60 in the decrementing direction in the situation depicted in FIG. 12A.

When, starting from the situation depicted in FIG. 12A, the number sleeve 60 and the support member 150 are rotated together in the incrementing direction, the deflected locking features 46 are sequentially displaced radially, in particular outwardly, for example by cooperation with the support member and/or on account of their resiliency, such that the feature 65, particularly surface 651 thereof, may engage the angular surface delimiting a subsequent, particularly the next, locking feature 46 in the incrementing direction. The number sleeve 60 may, in the incrementing direction, be rotated by cooperation with feature 77 of the button 70. This is apparent from FIG. 12B. Feature 77 may abut feature 65 to transfer the incrementing torque or force from the button to the number sleeve. Alternatively, a different feature may be applied, preferably at a different angular position, in order to transfer the incrementing torque to the number sleeve 60. However, it is apparent that having one feature which simultaneously interacts with the locking features 46 and also with feature 77, which as compared to the locking features 46 is arranged at a different axial position, is advantageous. The feature 65 may have an axial extension which is greater than the one of the locking features 46 and/or the feature 77.

As already mentioned above, the coupling between button 70 and support member 150 has a rotational clearance. Thus, the button 70 can be rotated relative to the support member 150, before the support member follows rotation of the button. For incrementing, the button 70 does preferably move the feature 65 in the incrementing direction before the support member 150 follows its rotation. In this way, rotation of the support member in the incrementing direction is not blocked by one of the locking features, as the locking feature can be displaced radially, particularly outwardly, because the feature 65 has been moved already and does no longer block this movement. Consequently, in FIG. 12B, as compared to FIG. 12A, the number sleeve 60 may have been rotated already, e.g. by one increment in the incrementing direction on account of the rotational clearance C depicted in FIG. 12B. The rotational clearance may be greater than or equal to an angular range defined by at least one locking feature or one unit increment, e.g. by at least two or exactly two adjacent locking features or two unit increments. The rotational clearance may be less than an angular range defined by three succeeding locking features or three unit increments. The rotational clearance may be less than an angular range defined by two succeeding locking features or two unit increments. In the situation in FIG. 12A, a rotational clearance may be present in both directions between button 70 and support member 150, where in FIG. 12B the clearance which allows relative rotational movement, in particular of the button 70 relative to the support member 150, in the incrementing direction has already been closed. The rotational clearance is used during the incrementing rotation to displace feature 65 relative to the locking features 46 before the support member 150 is rotated in the incrementing direction such that movement of locking features 46 which were deflected into section 153 out of the section 153 is facilitated. When the button 70 is rotated by the user in the incrementing direction, e.g. in the clockwise direction, the feature 65 is also rotated in this direction relative to locking features 46. Consequently, surface 652 is rotated in the incrementing direction and the locking features 46, in particular the ones that are in angular alignment with surface 652, can deflect radially, in particular inwardly, for example by cooperation with surface 652 and/or on account of their resiliency. The drive torque exerted by the spring 90 is reacted by the user.

In an embodiment, which is not explicitly illustrated, the support member 150 may be operatively coupled to the number sleeve 60. Particularly, the coupling may be configured such that the coupling tends to establish and maintain an angular relative position between a support feature and the block feature, in which the block feature and the support feature are separated by an angle less than the angle corresponding to one unit increment. For establishing the coupling, a spring may be connected to the number sleeve 60 and the support member 150. When the number sleeve 60 is rotated by the button in the incrementing direction, even before the rotational clearance between button 70 and support member 150 has been closed, the spring is preferably biased or was biased already and moves the support member in the incrementing direction to follow rotation of the number sleeve 60. In this way, it can be avoided that, once the button is released, the number sleeve rotates back by one unit increment until the rotation is stopped by the block feature abutting a locking feature which is supported by the support member. Rather, it can be guaranteed that always the locking feature which corresponds to the currently selected unit increment is supported as the support member follows rotation of the movable member in the incrementing direction more closely. This increases the user's confidence that the dose which he selected and which was indicated by the number sleeve 60 stays the same even after he has released the button 70.

Starting from the situation shown in FIG. 12A, if the mechanism shall be decremented, e.g. in order to decrease the set dose, the button 70 is rotated in the decrementing direction, e.g. anti-clockwise, relative to the housing 10. Until the rotational clearance relative to the support member is closed, the button rotates relative to the support member 150 in the decrementing direction. While doing so, the feature 77 is displaced away from feature 65. The drive torque of the spring 90, however, is still reacted by the feature 46 which is still supported by the support member 150 in the radial direction, as the support member 150 has not been rotated yet. When the support member 150 and the button 70 are rotationally coupled to co-rotate in the decrementing direction, the support member 150 is rotated relative to the locking features 46 such that the locking feature which the feature 65 abuts becomes radially displaceable. This situation is shown in FIG. 12C. In this situation, the releasable locking interface formed by feature 65 and locking feature 46 has been released, preferably only temporarily. On account of the drive torque exerted on the number sleeve 60 the locking feature is radially deflected or displaced such that the number sleeve is rotated in the decrementing direction, e.g. by one unit increment, until the feature 65 engages with the angular surface of a locking feature 46 which is supported by the support member 150, preferably the subsequent locking feature 46 in the decrementing direction. Then the mechanism is, again, in the situation shown in FIG. 12A. Decrementing can be performed unit-wise by continuing rotation of the button 70 in the decrementing direction. The number sleeve 60 automatically follows movement of the button using the drive torque of the drive spring.

In order to switch the mechanism to the driving configuration, starting from the situation depicted in FIG. 12A, the button 70 is axially displaced in the distal direction and together therewith the drive sleeve 40 with the locking features 46. This results in a relative axial movement between feature 65, which serves as a block feature in the decrementing configuration, and locking feature 46, thereby allowing free rotation of the number sleeve 60 in the decrementing or driving direction under the influence of the drive spring 90. This also results in a relative axial movement between feature 65 and feature 77, thereby allowing free rotation of the number sleeve 60 relative to the button 70. Splines on the button 70 may engage with splines on the housing 10, preventing rotation of the button 70 during dispense as previously described. In the driving configuration, the drive sleeve 40 is rotationally coupled to the number sleeve 60 such that drive sleeve 40 and number sleeve 60 rotate together. Preferably, the drive sleeve 40 follows axial movement of the button 70 to disengage the splined connection with respect to the housing 10 and enter into the splined connection with the number sleeve 60. When the dose has been delivered, the user releases the button and the clutch spring 140 displaces the drive sleeve 40 and the button 70 proximally, so as to switch the mechanism back into the decrementing configuration. If the relative angular position between the support feature 152 and the feature 65 is not suitable yet for an incrementing movement, as the angular distance between the support feature and the feature 65 is this too large, the button 70 and together with it the support member 150 may be rotated in the incrementing direction relative to the number sleeve 60, until the number sleeve 60 follows rotation of the button 70 or dose selector in the incrementing direction. When this is done, the user can be sure that the features 77 abuts feature 65 again and also that, once he releases the button 70 of the dose selector, the selected dose stays as it is and is the correct dose as indicated by the number sleeve 60.

Similar as for the embodiment described further above, instead of using locking features 46 provided on the drive sleeve 40, the locking features 46 could also be provided on a component which is static relative to the housing 10 in the driving configuration and in the decrementing configuration of the assembly.

The general configuration of the locking features is similar to the teeth of a comb and the general way of operation of the mechanism is similar to the one of a radial ratchet mechanism as angular faces are used to block movement of a component temporarily and radial deflection is used to increment and/or decrement the ratchet mechanism.

The mechanism has a variety of advantages: The feature 65 is unable to rotate and release its torsional load unless an external torque is applied to the dialling component/button 70. This ensures that the ratchet does not slip under the torsional load exerted constantly via the feature 65. The rotational clearance between button 70 and support member 150 further avoids that external torque is immediately transferred to the support member which further prevents unintentional decrementing.

The torque required to increment and decrement the dose depends on the drive spring torque, the radial stiffness of the locking features and the angles between contact faces at the engagements between the feature 65 and the locking features. The rotational locking strength of the mechanism under the action of the drive spring torque is independent of these factors. The rotational locking strength is dependent on the tangential or angular stiffness of the flexible connection between the locking features and the drive sleeve 40 and on the geometry of the support feature surface. This allows the torque required to increment and decrement the dose to be tuned without affecting the locking strength. This is of particular benefit as the torsional drive load encountered by the locking features can vary with both angular direction and dose size. Keeping the applied torque requirements and locking action independent means that the user experience can be adjusted to an acceptable, optimized feel and sound, whilst minimizing the risk of the slippage due to constant application of the drive torque. The advantage over what is currently in the field is that this embodiment offers more design freedom to be tuned to precisely meet the user needs and the essential engineering requirement for no slippage (which can affect dose accuracy). The mechanism may be adaptable to change to different dose increments. Ideally the increment and decrement actions are symmetric in torsional force and increment size for the end user. However this might be challenging due to the variable loading options (via variable dose size) and the torsional drive spring which is always driving to decrement the dose. Unintended decrement or slippage of components under the action of the drive spring, which would result in inaccurate dosing, is prevented by the proposed mechanism.

It should be noted that, instead of using axially oriented locking features 46, the mechanism described above could also be realized using radially oriented features which are axially deflectable. In this case, references to "radial" in the general part of the description and above are expediently substituted by "axial" as necessary. For example, the support member 150 would then have to support the locking features 46 against axial displacement and an axial surface of the respective locking feature would be contacted by the support feature. Likewise, the block feature would extend axially but still contact an angular face of the respective locking feature. For drug delivery devices, however, the configuration with the axially extending locking features is particularly advantageous, which is why the above description focuses on this implementation.

Another exemplary embodiment of an incrementing and decrementing mechanism or assembly is described below with reference to FIGS. 13 through 17.

Figure 13:
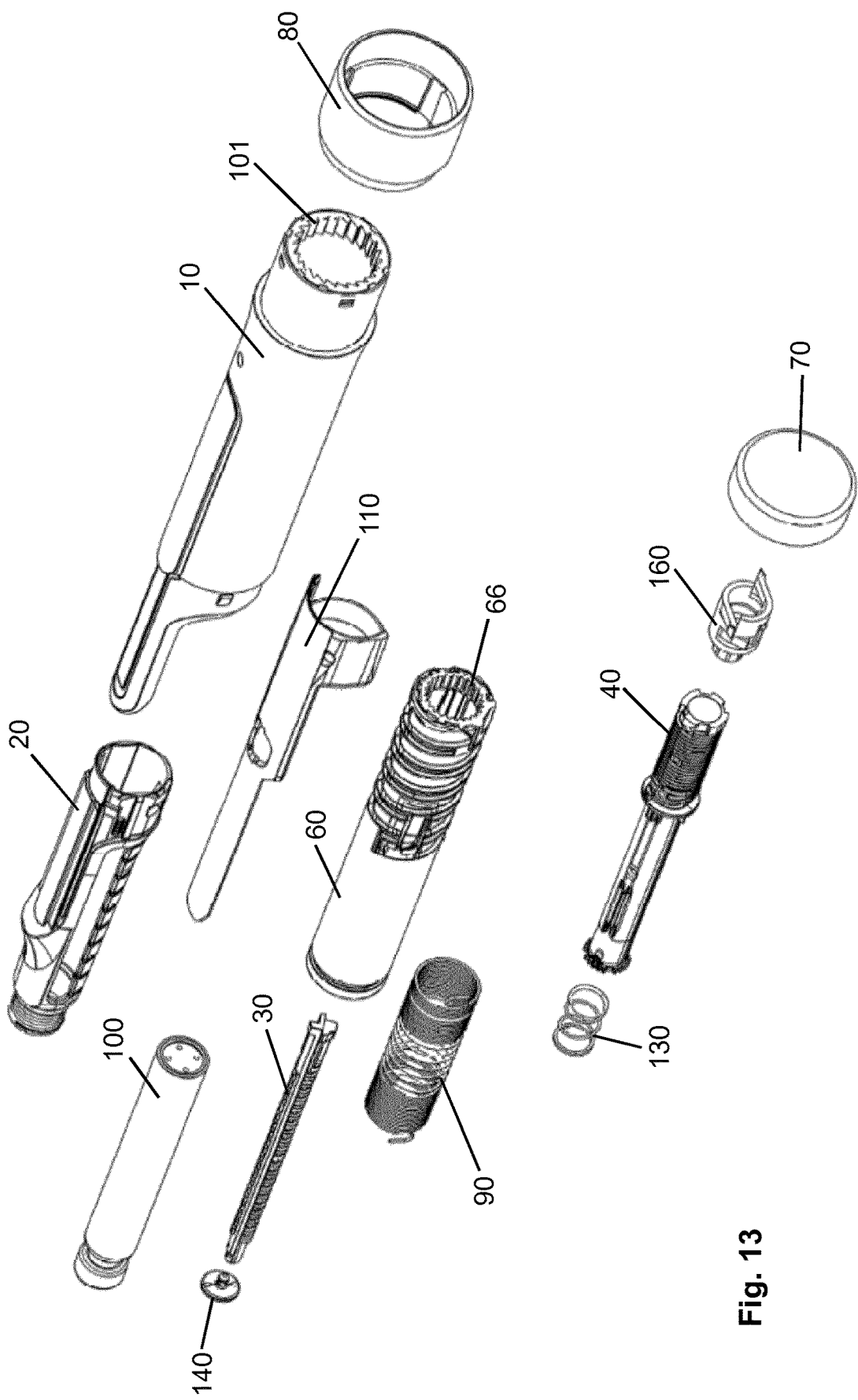
FIG. 13 shows the parts of a drug delivery device which comprises the mechanism according to yet another embodiment in a perspective view.

FIG. 13 shows the parts of a drug delivery device which comprises the mechanism according to this embodiment in a perspective view. The device essentially corresponds to the device described in conjunction with FIGS. 1 through 5, which is slightly modified as explained below. The dose indicator or number sleeve 60 is depicted as a single part in FIG. 13. However, instead of being unitary, the number sleeve may also be formed of a plurality of parts as explained previously. Further, the indices on the number sleeve 60 are not explicitly shown. Although the nut 50 is not shown in FIG. 13, it may well be present in the device. The decrementing functionality which, in the embodiment described in conjunction with FIGS. 1 through 5, is realized utilizing clutch plate 120 is realized differently in this embodiment. Consequently, clutch plate 120 is not present in this embodiment. Rather, for this embodiment, some of the components have been modified and a new component has been added, i.e. a locking member or clutch member 160.

Figure 14:
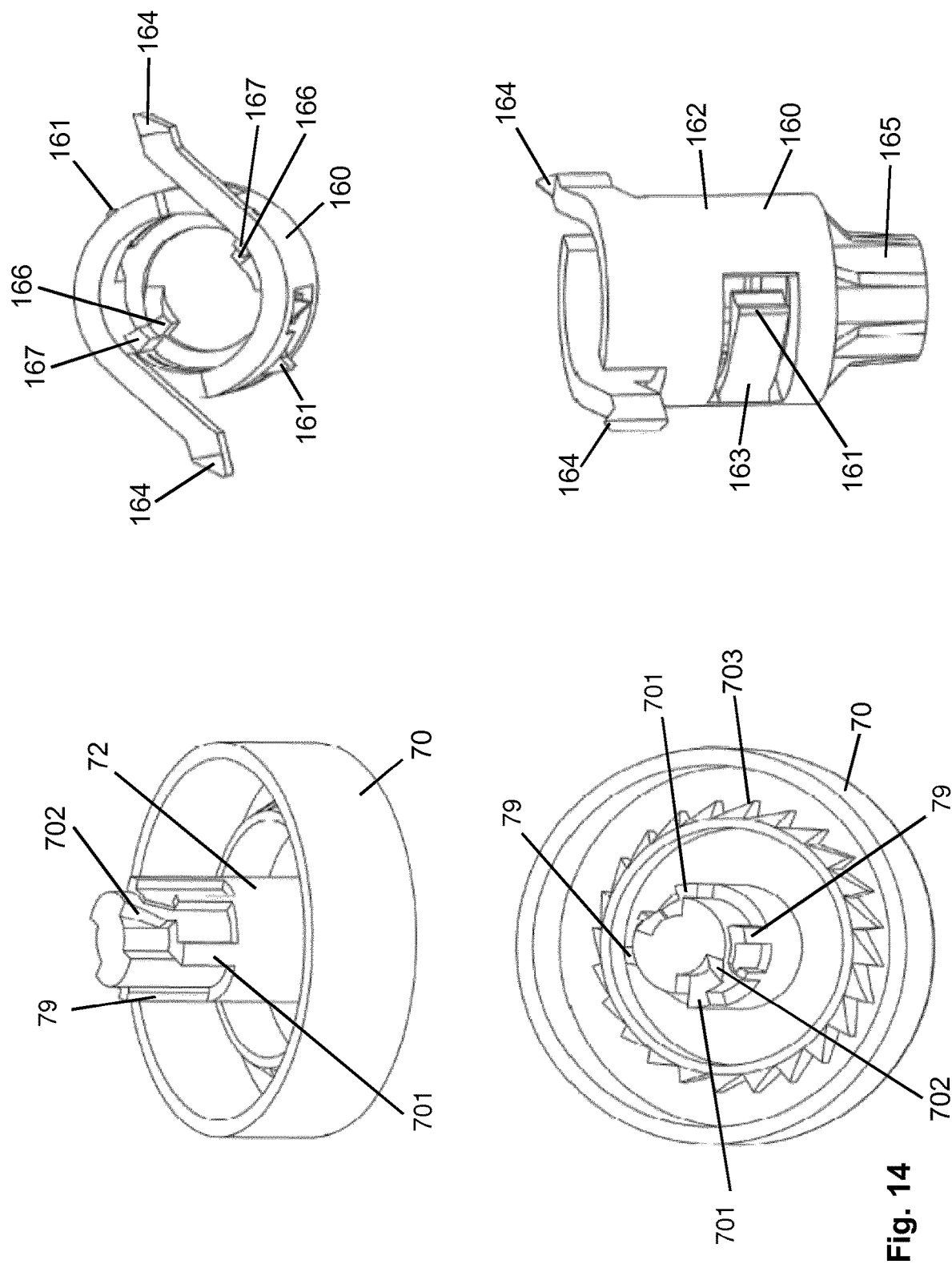
FIG. 14, on the basis of various views, shows components which are involved in the incrementing and decrementing mechanism according to this embodiment in various views.

FIG. 14, on the basis of various views, shows the button 70 and the locking member 160. These components participate in the incrementing and decrementing mechanism of this embodiment. Further components, which have been modified as compared to the device shown in FIGS. 1 through 5, are the housing 10 and the number sleeve 60.

The locking member 160 comprises one or a plurality of locking features 161. In the present embodiment, the locking member 160 comprises two locking features which are preferably uniformly distributed in the circumferential direction over the locking member. One locking feature might, however, be sufficient to achieve the desired functions, whereas two or even more than two locking features may be beneficial with respect to a broader distribution of the load. The locking features 161 are designed to selectively lock the locking member 160 and the number sleeve 60 rotationally. Particularly, for an incrementing rotational movement, the rotational lock may be established whereas for the decrementing movement the rotational lock may be released. For achieving the releasable rotational locking, the number sleeve 60 comprises a plurality of block features 66. The block features may be uniformly distributed in the angular direction over the number sleeve 60. Of course, instead of being integrated into the number sleeve 60, a separate component with the block features may be rigidly attached to the number sleeve 60 such that the block features 66 are rotationally and axially locked to the number sleeve 60. The block features 66 are expediently provided in the proximal section of the number sleeve 60. The locking features 161 are connected to a locking member body 162 in a flexible manner. Consequently, the locking features may be flexibly displaced with respect to the locking member body in the radial direction. For this purpose, the locking features are connected to the locking member body via a flexible arm 163, which may be oriented in the angular direction. The locking features 161 are expediently resiliently connected to the main body. Particularly, the flexible arm 163 may be elastically displaced with respect to the locking member body 162. The locking member 160 may be a unitary component.

The locking member 160 further comprises one or a plurality of unidirectional interface features 164. The interface features 164 are expediently uniformly disposed in the angular direction over the locking member. In the depicted embodiment, the locking member 160 comprises two interface features 164 which are preferably uniformly distributed in the circumferential direction over the locking member. One interface feature might, however, be sufficient to achieve the desired functions, whereas two or even more than two interface features may be beneficial with respect to a broader distribution of the load. The respective interface feature 164 may be oriented in the radial direction. The respective interface feature 164 is designed as a flexible and elastically deflectable ratchet arm in this embodiment. The interface features are designed to cooperate with corresponding interface features to form a unidirectional interface which allows rotation of the locking member 160 relative to the housing 10 in the incrementing direction only, presently the clockwise direction. In this embodiment, the corresponding interface features which cooperate with features 164 are realized by ratchet teeth 101 which are provided on the housing 10 or a component rigidly secured thereto. The interface features 164 are expediently offset from the locking features 161 in the axial, e.g. proximal, direction. The locking member 160 further comprises a region 165, which may have a reduced radial width. This region 165 of the locking member 160 is expediently axially, e.g. distally, offset from the locking features 161 and arranged to be guided into the drive sleeve 40. The number of block features 66 may correspond to the number of unit increments, which is expediently defined by the ratchet teeth 101. Specifically, the number of block features 66 may be equal to the number of ratchet teeth 101.

The locking member 160 further comprises one or more button interface features 166. The features may be provided on an interior surface of the locking member. These features are designed to interact with features of the button 70 as will be explained further below. The interface features 166 expediently are configured to establish a helical interface to the button which, when the button is rotated in the decrementing direction results in a displacement of the button 70 relative to the locking member 160 in the proximal direction. The button interface features 166 are expediently provided in the interior of the locking member 160. The button interface features 166 may be offset from the locking features 161 axially, e.g. in the distal direction.

The locking member 160 further comprises one or a plurality of features 167. The features may be provided on an interior surface of the locking member. These features may be designed to transfer drive torque, particularly in the incrementing direction from the button 70 and/or the dose selector 80 to the number sleeve 60. The features 167 can therefore also be called drive features. The features 167 are expediently uniformly disposed in the circumferential direction over the locking member 160. The features 167 may, as compared to the interface features 166, be offset in the proximal direction. In terms of their axial position the features 167 may overlap with the locking features 161.

The button 70 comprises the support 72. The support 72 comprises one or a plurality of support features 79. The support features 79 may be uniformly disposed in the angular direction. The support features expediently extend in the axial direction. The support features 79 expediently protrude radially from the support 72. The support features 79 are arranged to selectively support the locking features 161 against radial displacement, particularly in the inward direction. Accordingly, when the locking feature 161 is supported, the engagement of the locking feature with the block features 66 cannot be released as radial displacement, particularly in the inward direction, which would be required to release this engagement is prevented by means of the support feature 79.

The button 70 further comprises one or more features 701 which are provided on the support 72. Features 701 are expediently designed to engage features 167 of the locking member 160 in order to transfer drive torque from the button 70 to the locking member 160. Features 701 are angularly separated from features 79. Features 701 overlap axially with features 79. The features 701 expediently protrude radially from the support 72. The axial extension of features 701 may be greater than the one of the support features 79.

Furthermore, the button 70, particularly on the support 72, comprises one or more locking member interface features 702. The interface features 702 are provided to interact with interface features 166, particularly to provide a helical interface between button 70 and locking member 160. The interface features 702 may extend helically for this purpose. The interface features 702 may be distally offset from or extend more distally than the support features 79. By means of the helical interface, it can be achieved that the button maintains a defined angular position relative to the locking member, this position being preferably the one where the support features 79 block radial movement of the locking features 161.

The button 70 further comprises a set of teeth 703. The teeth 703 are oriented in the radial direction and are designed to mesh with ratchet teeth 101 in the housing in order to prevent rotational movement of the button 70 in the driving configuration of the mechanism. Consequently, as compared to the previously described embodiments spline features 76 which were provided for this purpose on the button can be dispensed with.

When assembled, the support 72 is received within the locking member 160 such that features on the support can interact with the associated features of locking member.

Figure 16:
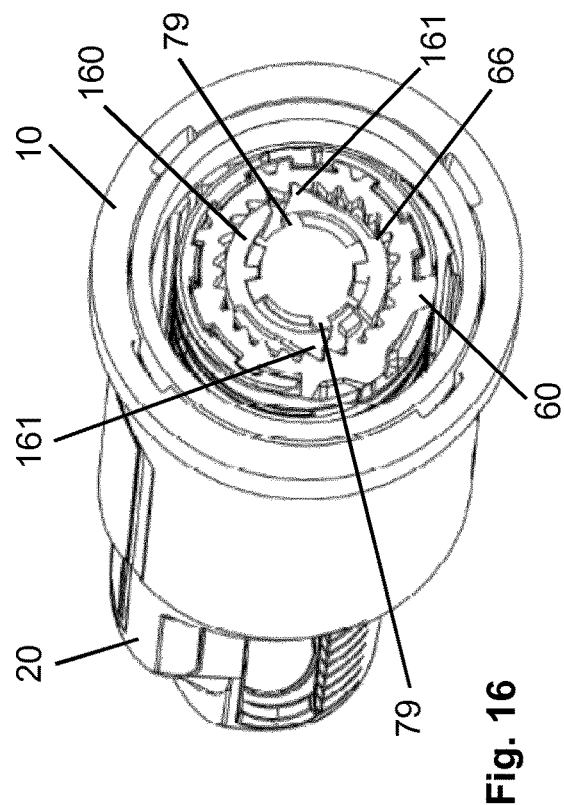
FIG. 16 shows parts involved in the incrementing and decrementing mechanism according to this embodiment in an assembled state.
Figure 15:
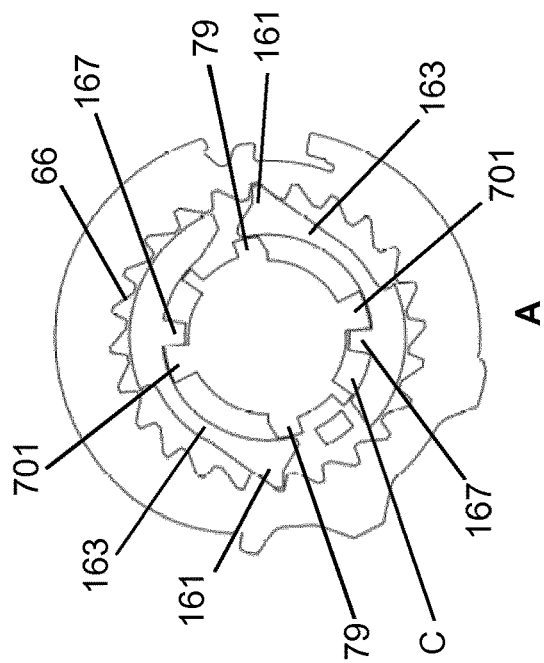
FIG. 15 shows parts involved in the incrementing and decrementing mechanism according to this embodiment in an assembled state.
Figure 15:
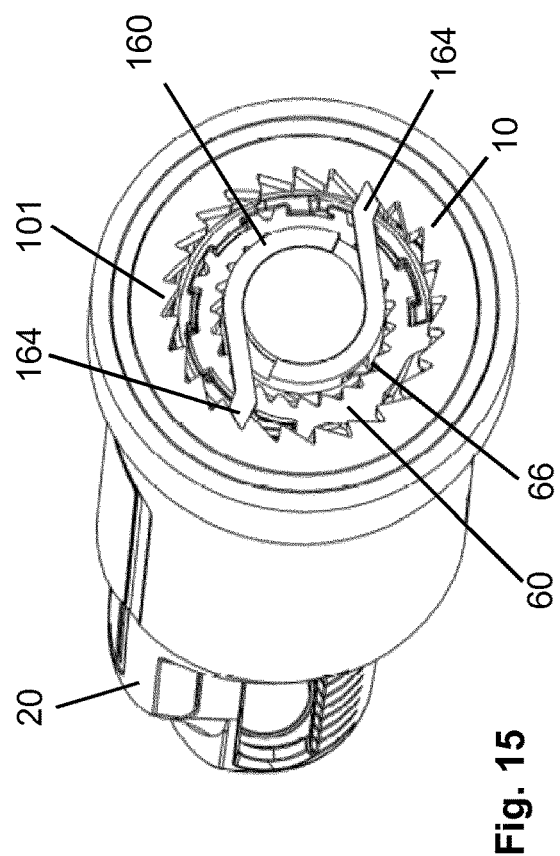

FIGS. 15 and 16 show parts involved in the incrementing and decrementing mechanism in an assembled state. In FIG. 15 the unidirectional ratchet realized by the ratchet teeth 101 and the unidirectional interface features 164 is shown. It is readily apparent for a person of skill in the art, that the ratchet arms could also be provided on the housing and the circumferentially arranged ratchet teeth could be provided on the locking member without changing the way of operation of the unidirectional interface. The ratchet teeth 101 have, with respect to the radial direction asymmetric angular side faces which delimit the respective tooth in the angular direction. Specifically, the side faces have different inclinations. The steeper side face is designed to block relative rotation between the locking member 160 and the housing 10 in the decrementing direction, whereas the more inclined side face is configured to allow rotation of the locking member 160 relative to the housing 10 in the incrementing direction.

In FIG. 16, the locking interface which is established between the locking member 160 and the number sleeve 60 is shown. The locking interface is established and maintained as long as the support features support the locking features which ensures that the locking features 161 are kept in engagement with the block features 66. The support features 79 may support the locking features 161 such that they are resiliently deflected from an undeflected state. Thus, the locking features may tend to disengage from the block features on account of their resiliency. As is apparent from FIG. 16, the block features 66 are realized as teeth which may have asymmetric angular side faces which delimit the respective tooth in the angular direction. Preferably, a side face delimiting one tooth in the decrementing direction may be more inclined relative to the radial direction than the angular side face delimiting that tooth in the incrementing direction. When established, the locking interface expediently prevents any relative rotational movement between the locking features 161 and the block features 66.

In contrast to the previously described embodiments of incrementing and decrementing mechanisms, in the present mechanism, the unidirectional interface is operative during incrementing and decrementing. However, the additional rotational locking interface between the locking member 160 and the number sleeve 60 may be released by changing the angular position of the support features 79 with respect to the locking features 161. Once the locking features are no longer supported, they may be displaced inwardly which releases the locking interface.

Figure 17:
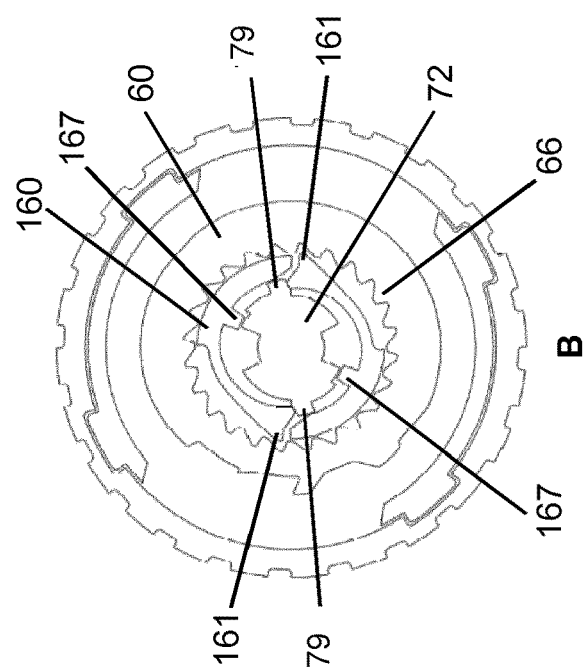
FIG. 17 shows components of the incrementing and decrementing mechanism according to this embodiment in different situations in representations A and B.

In the following, operation of the mechanism for incrementing and decrementing is described, in particular with reference to FIGS. 15 through 17. FIG. 17 illustrates the situation when the mechanism can be incremented in FIG. 17A, which essentially is the same situation depicted in FIG. 16. In this situation a zero or non-zero dose can be set. As shown in FIG. 17A, the support features 79 support the locking features 161 against radial inward displacement and consequently, the locking member 160 is rotationally locked with respect to the number sleeve 60 in both rotational directions. Features 701 of the button 70 abut drive features 167 such that drive torque can be transmitted from the button 70 to the locking member 160 in the incrementing direction. If the button is rotated in the incrementing direction, so is the locking member 160 and, along therewith, the number sleeve 60 as rotation in this direction is permitted by the unidirectional interface provided via interface features 164 (see FIG. 15). The drive torque exerted by the drive spring 90 is reacted by the unidirectional ratchet interface and transferred to this interface by the locking features 161 which engage the block features 66.

The button 70 is coupled to the locking member 160 such that there is a rotational clearance, which permits relative rotation between the button 70 and the locking member 160, particularly in the decrementing direction. Thus, when the mechanism is in the decrementing configuration shown in FIG. 17A a rotation of the button 70 relative to the locking member 160 in decrementing direction, i.e. the anticlockwise direction in the exemplary embodiment, is allowed. The rotational clearance is preferably at least great enough such that the support features 79 can be moved angularly such that the locking features 161 are no longer supported by the support features 79. This situation is shown in FIG. 17B. Once the radial support has been removed, the locking features 161 on their own cannot react the load of the drive torque and, consequently are, under the influence of the drive torque and by cooperation of the locking features with the angular face delimiting the associated block feature in the decrementing direction, displaced radially, e.g. inwardly, and the number sleeve 60 is allowed to rotate freely in the decrementing direction. In other words, the drive torque is used to disengage the locking features 161 and the block features 66. Alternatively or additionally the resiliency of the locking features may assist the disengagement from the block features 66. The button 70 may be secured in the position shown in FIG. 17B by the locking features 161 which may abut an angular face of the button 70, e.g. of feature 79 as depicted, to prevent an unintentional movement of the button relative to the locking member in the incrementing direction.

The number sleeve 60 is allowed to rotate in the decrementing direction until the button is rotated again in the incrementing direction relative to the locking features such that the locking features 161 are re-engaged with the block features 66 or until the number sleeve reaches its initial position, e.g. a zero dose position. In order to facilitate re-engagement of the locking features 161 with the block features 66, the interface between the support 72 and the locking feature 161 is expediently configured such that rotation of the button 70 in the incrementing direction is converted into radial movement of the locking feature 161 back into engagement with the block features 66. For example, the feature 701 may have an inclined surface which abuts the locking feature 161 for this purpose. The number of unit increments which are decremented during the decrementing operation is independent of the unidirectional interface and may vary between one unit increment and all unit increments which have been set.

While the button is rotated in the decrementing direction it may, on account of the helical interface provided by cooperation of features 702 and 166 be displaced axially, particularly proximally relative to the locking member 160. This is why the cross-sections shown in FIGS. 17A and 17B look different. However, the proximal movement is not absolutely necessary for the mechanism to operate. Via the helical interface the button may be biased towards the position in which the support features 79 support the locking features 161 as the incrementing operation is the primary operation for the mechanism. In an alternative embodiment, this bias could also be provided by a torsional load applied to the button in the incrementing direction such as by a biasing spring, for example.

When, e.g. from the situation shown in FIG. 16, the button 70 is depressed, such as for dispensing a set dose, the mechanism is switched from the decrementing configuration to the driving configuration. In this configuration the locking features 161 are disengaged from the block features 66 due to the relative axial movement between the locking features 161 and the number sleeve 60. Specifically, the locking member 160 is displaced in the distal direction relative to the number sleeve 60 and the block features and the housing 10. This releases the releasable locking interface. Also, the drive sleeve 40 is displaced in the distal direction and rotationally disengaged from the housing 10 and, instead, coupled rotationally to the number sleeve 60. Thus, the number sleeve 60 may rotate freely in the decrementing or driving direction under the influence of the torque exerted by the drive spring 90. The drive sleeve 40, which is now rotationally coupled to the number sleeve rotates with the number sleeve and may drive the dispensing movement. When the force on the button 70 is removed, the clutch spring 140 moves the drive sleeve again in the proximal direction and the locking features and the block features are re-engaged. In the driving configuration, teeth 703 provided circumferentially around the support 72 of the button may mesh with ratchet teeth 101 in the housing 10 in order to prevent rotation of the button 70 and/or the transfer of drive torque via the button to the user. In this configuration, the unidirectional interface is not released and/or established as well. Thus, the locking member 160 may not rotate relative to the housing 10. The drive sleeve 40, however, is not coupled rotationally to the locking member 160 and may rotate freely relative to the locking member 160.

It is readily apparent that, instead of providing the ratchet teeth 101 on the housing 10 and the interface features 164 on the locking member 160, the teeth could be provided on the locking member and the interface features on the housing. The unidirectional interface would still function in the same way.

In other words, this mechanism uses a radial ratchet to enable active increment of unit dose adjustment on a cartridge based, torsionally driven pen injector in conjunction with a mechanism for releasing a rotational lock between two components to allow automatic decrement of the selected dose under the internal torsional load. The present mechanism has a variety of advantages. Dose increment is achieved by the user applying torsion to an external dose dialling component (button 70) which is free to move in the increment angular direction. Rotation of this dialling component increments the dialled dose in units by unit increments. Dose decrement is achieved by the user applying torsion to the dialling component. This component rotates through a small angle, e.g. less than 90° or less than 45°, in the decrementing direction and then, preferably locks in place. This rotation releases one or more locking features which allows the internal torsional load to rotate an internally driven component (number sleeve 60) in the dose decrement direction until the user removes the external torque. The decrementing mechanism is separate from and independent of the incrementing mechanism. This enables fine tuning of the increment mechanism features to meet the user force/displacement requirements without affecting the decrementing process. The incrementing mechanism (comprising the unidirectional ratchet) is not required to be released in the decrementing direction. This allows optimization of the ratchet features 101 and/or features 164 to ensure that the ratchet does not slip under the torsional load applied to the clutch component.

The proposed independent, particularly asymmetric, mechanism allows a unique, independent tuning of the forces required to both increment and decrement the dose. This is of particular benefit as the torsional drive load encountered by the ratchet and locking features can vary with both angular direction and dose size. By tuning both the incrementing and decrementing independently the user experience can be adjusted to an acceptable, optimized feel and sound, whilst minimizing the risk of the slippage due to constant application of the drive torque. The advantage over what is currently in the field is that this embodiment offers more design freedom to be tuned to precisely meet the user needs and the essential engineering requirement for no slippage (which can affect dose accuracy). The mechanism may also be adaptable to change to different dose increments. An advantage of the decrement mechanism is that it is very easy for the user to dial the dose down to zero from any dialed in or set dose.

Figure 18:
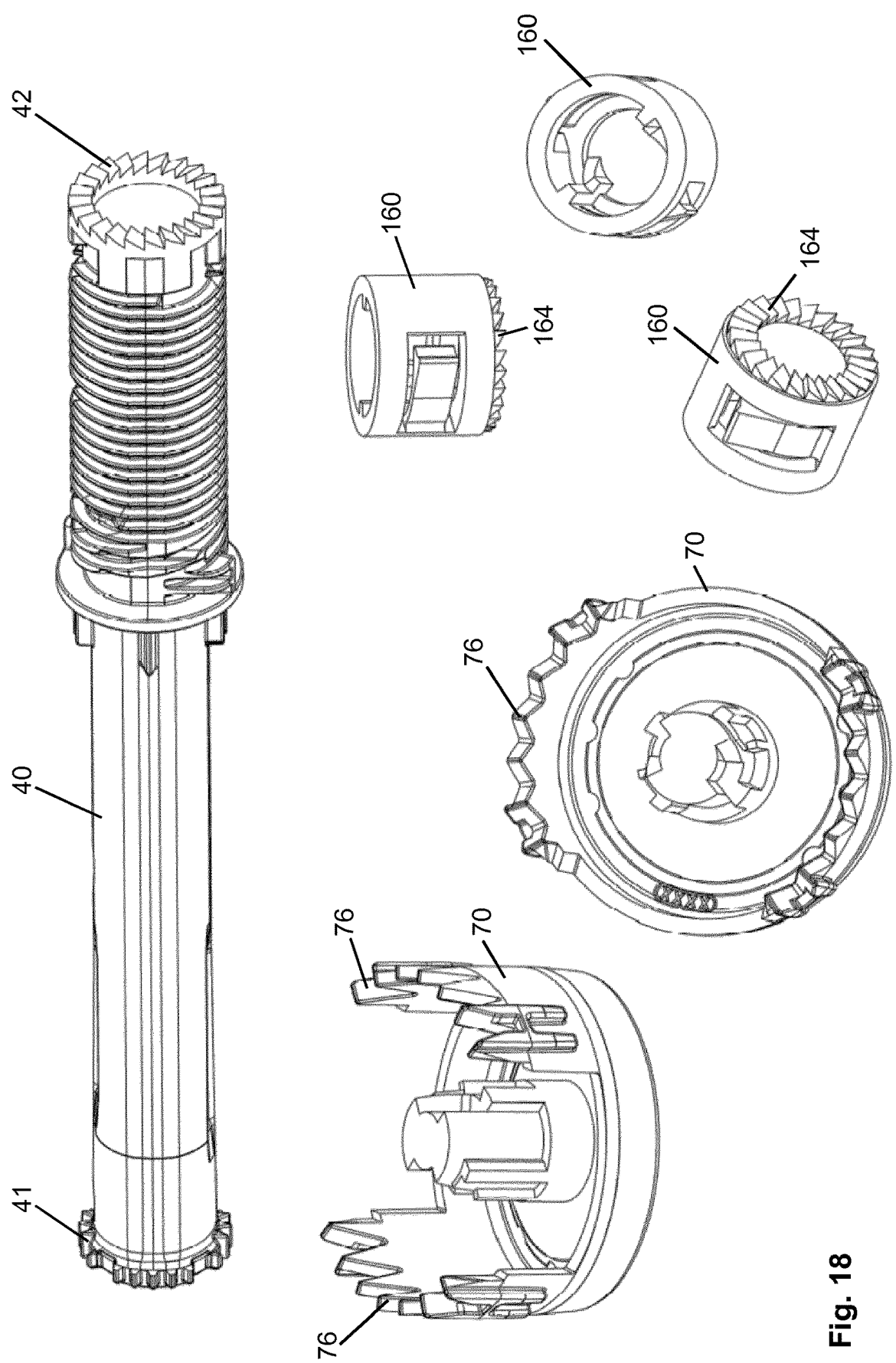
FIG. 18 shows components of an incrementing and decrementing mechanism which were modified as compared to the previous embodiment in order to provide a modified embodiment of the incrementing and decrementing mechanism in different views.

In the embodiment which has been described previously, the unidirectional interface which prevents rotation of the number sleeve 60 in the decrementing direction in the decrementing configuration has been realized by way of a unidirectional ratchet interface between the housing 10 or a component rigidly attached thereto and the locking member 160. Thus, the unidirectional interface is realized between a component which is permanently static and does not move at all during operation of the device and the locking member 160. However, also a component which is rotatable in the driving configuration, e.g. in the decrementing direction, but is rotationally locked with respect to the housing 10 in the decrementing configuration can be used to provide the counterpart for the unidirectional interface in addition to the locking member 160. Such a component is the drive sleeve 40, for example. FIG. 18 illustrates some components of the device described in the previous embodiment, which are modified for using the drive sleeve 40 as one component of the unidirectional interface.

For this purpose, the drive sleeve 40 is provided with a plurality of ratchet features 42, which are oriented in the axial direction in the shown embodiment. The unidirectional interface features 164 on the locking member 160 are realized by likewise axially oriented teeth which are configured to mesh with the ratchet teeth 42 provided on the drive sleeve 40. Consequently, rotation of the locking member 160 relative to the drive sleeve 40 in the decrementing direction is prevented, when features 42 and 164 are engaged. The unidirectional interface features extend in the distal direction, e.g. from a distal section of the locking member 160. Region 165 which was received in the drive sleeve 40 in the previously described embodiment is not present in the locking member 160 according to this modification. Further, as the housing 10 is no longer provided with ratchet teeth 101, spline features 76 are again provided on the button 70 which ensure that the button 70 is splined to the housing when depressed.

The unidirectional interface allows rotation of the drive sleeve 40 in the decrementing or driving direction relative to the locking member 160 such that the ratchet teeth ride over each other in the driving configuration, when the number sleeve 60 and the drive sleeve 40 rotate. This relative rotation may be used to provide an audible and/or tactile dispense or drive feedback to the user. The clutch spring 140 tends to keep the ratchet teeth on the drive sleeve 40 and the ones on the locking member 160 in permanent abutment.

Instead of using axially extending ratchet teeth for the unidirectional interface, a radial ratchet which utilizes radially oriented teeth in conjunction with a radially oriented ratchet arm which is flexible could also be applied between the drive sleeve 40 and the locking member 160.

Apart from the modifications which enable to use the drive sleeve 40 as temporarily rotationally fixed base for the unidirectional locking interface, the mechanism functions as discussed further above in connection with the previous embodiment.

It should be noted that, instead of radially deflectable locking features 161, the mechanism described above, including the modification discussed in conjunction with FIG. 18 could also be realized using axially deflectable locking features. In this case, references to "radial" in the general part of the description and above are expediently substituted by "axial" as necessary. For example, the support features 79 would then have to support the locking features against axial displacement and an axial surface of the respective locking feature would be contacted by the support feature. For drug delivery devices, however, the configuration with the radially deflectable locking features is particularly advantageous, which is why the above description focuses on this implementation.

Another exemplary embodiment of an incrementing and decrementing mechanism or assembly is described below with reference to FIGS. 19 through 22.

Figure 19:
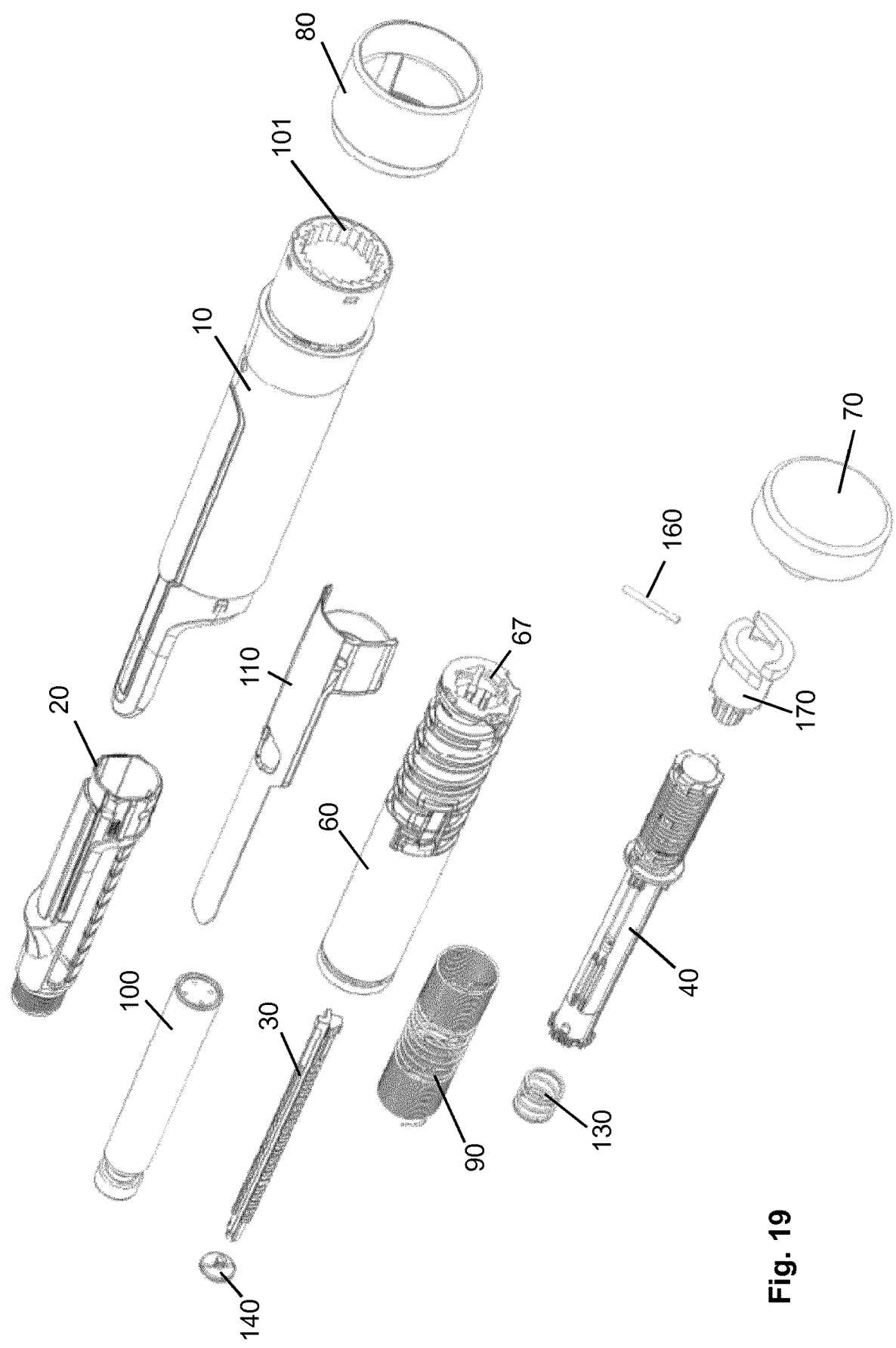
FIG. 19 shows the parts of a drug delivery device which comprises the mechanism according to yet another embodiment in a perspective view.

FIG. 19 shows the parts of a drug delivery device which comprises the mechanism according to this embodiment in a perspective view. The device essentially corresponds to the device described in conjunction with FIGS. 1 through 5, which is slightly modified as explained below. The dose indicator or number sleeve 60 is depicted as a single part in FIG. 19. However, instead of being unitary, the number sleeve may also be formed of a plurality of parts as explained previously. Further, the indices on the number sleeve are not explicitly shown. Although the nut 50 is not shown in FIG. 19, it may well be present in the device. The decrementing functionality which, in the embodiment described in conjunction with FIGS. 1 through 5, is realized utilizing clutch plate 120 is realized differently in this embodiment. Consequently, clutch plate 120 is not present in this embodiment. Rather, for this embodiment, some of the components have been modified and two new components have been added, i.e. a clutch member 170 and a locking member 160.

Figure 20:
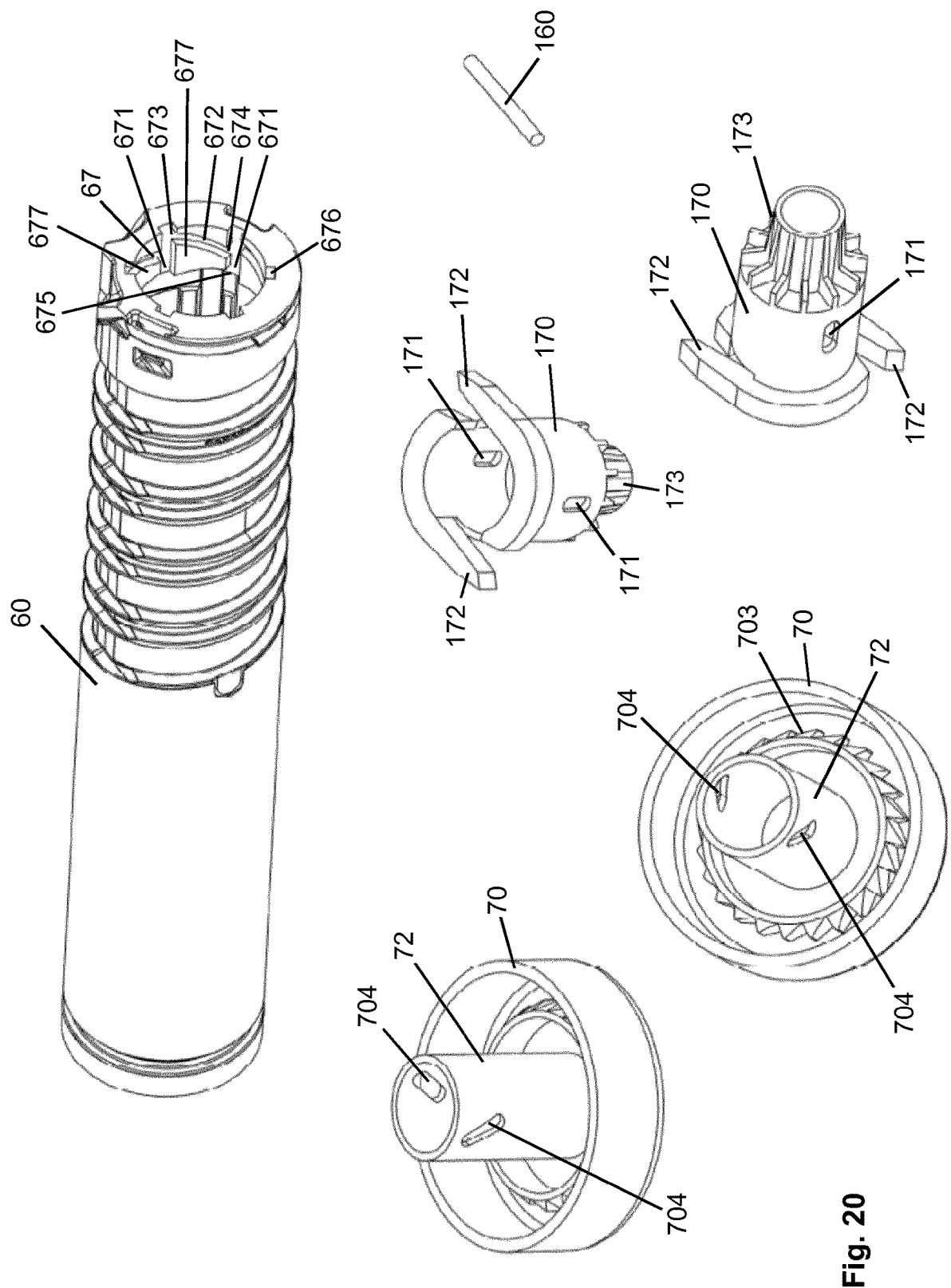
FIG. 20, on the basis of various views, shows components which are involved in the incrementing and decrementing mechanism according to this embodiment in various views.

FIG. 20, on the basis of various views, shows components which are involved in the incrementing and decrementing mechanism according to this embodiment.

The locking member 160 is, in this embodiment, embodied as a pin, particularly a straight pin. Locking member 160 is expediently rigid and, particularly, can withstand the load transferred to it by the drive spring 90 during operation of the device in order to prevent rotational movement of the number sleeve 60 in the decrementing direction. The locking member 160 has a length which is great enough such that the locking member can interact with a guide track 67 defined in the number sleeve 60. Particularly, the length of the locking member may be greater than the outer diameter of the drive sleeve 40 and/or less than or equal to the inner diameter of the number sleeve 60 particularly in that section where the guide track 67 is arranged or greater than or equal to the inner diameter of the number sleeve 60, especially in the section where the guide track 67 is arranged. Particularly, the length of the locking member 160 may be greater than a minimum inner diameter of the number sleeve in the section with the guide track 67 and/or less than or equal to the maximum inner diameter of the number sleeve 60. In the section with the guide track 67, profiled features may delimit the guide track and define the minimum inner diameter of the number sleeve 60. The locking member 160 is established to provide the releasable locking interface which prevents movement of the number sleeve 60 in the decrementing direction, particularly preferably by cooperation with the guide track 67 which is explained later on more detail. In order to release the releasable locking interface, the pin may be axially displaceable relative to the number sleeve 60. The locking member 160, in the assembled mechanism, extends oblique, in particular perpendicular to the longitudinal axis or rotation axis of the number sleeve.

As already noted above, the number sleeve 60 comprises a guide track 67. The guide track 67 may be provided in a proximal region of the number sleeve 60. The guide track 67 expediently extends over the entire circumference of the number sleeve 60. The guide track 67 is further configured as a closed track. Thus, after having travelled 360° in the angular direction in the track, the point of origin is reached again. The guide track 67 has at least two different types of sections, a locked section 671 and an unlocked section 672. The guide track 67 comprises at least one locked section 671 and at least one unlocked section 672. Preferably, the guide track comprises a plurality of locked sections 671 and unlocked sections 672. As seen along the guide track 67, the locked sections 671 and the unlocked section 672 are alternatingly disposed. Accordingly, as seen in the angular or circumferential direction, a locked section 671 is followed by an unlocked section 672 which, again, is followed by a locked section 671 and so on. The sections may be defined by profiled features which protrude from the number sleeve 60, in particular in the radial inward direction. The locked sections 671 are axially oriented, expediently only axially, whereas the unlocked sections 672 extend in the axial direction and the angular direction, which results in a helical configuration or arrangement of the unlocked sections 672. Via a transition region 673, which is arranged expediently near or at the proximal end of the locked section 671, a locked section 671 may be connected to the subsequent unlocked section 672. As seen from the transition region 673, particularly in the incrementing direction, e.g. the clockwise direction, the unlocked section extends in the axial direction away from the transition region 673, particularly in the distal direction, and in the angular direction until the next locked section 671 is reached. The transition region 674 between the unlocked section and the subsequent locked section is axially offset, particularly in the distal direction, from the transition region 673. Expediently, the locked sections are, as seen in the angular direction, on one side or both sides bounded by a profiled feature 677 which may serve as block feature(s). As seen in the axial direction, the unlocked sections are expediently bounded on the proximal side and/or on the distal side by a profiled feature. The locked sections 671 and/or the unlocked sections 672 are uniformly distributed in the angular direction and/or formed alike.

When the locking member 160 is arranged in the locked section 671, relative rotation between locking member 160 and number sleeve 60 is prevented, at least in one rotational or angular direction, preferably in both rotational directions. For this purpose, the locking member abuts a wall delimiting the locked section in the angular direction. The wall is formed by a profiled feature 677. When the locking member is arranged in the locked section 671, rotation of the locking member in the incrementing direction relative to the housing 10 is transferred to the number sleeve 60. Rotation of the number sleeve 60 in the decrementing direction relative to the locking member 160 is blocked when the locking member 160 cooperates with the locked section 671. The locking member 160 is axially displaceable, particularly in the distal and the proximal directions, relative to the number sleeve 60 and, particularly relative to the guide track 67. Thus, the locking member can be moved to be brought into cooperation with the different sections of the guide track 67. When the locking member 160 cooperates with the unlocked section 672, the number sleeve 60 can rotate with respect to the housing 10 and also with respect to the locking member 160 and, while doing so, displaces the locking member 160 in the axial direction, particularly the distal direction, on account of the helical configuration of the unlocked section, until the locking member is arranged in the subsequent locked section 671 of the guide track 67. Then relative rotation is blocked again. The angular extension of the unlocked sections may be or may be defined by a whole-number multiple of the angular distance which has to be covered to increment the mechanism by one unit increment.

The locked sections 671 have at least one open axial end 675, particularly an open distal end, end. Via this end, the locking member 160 may leave the guide track 67. When the locking member is removed from the guide track 67 via the open end, the mechanism is switched from the decrementing configuration into the driving configuration. In the driving configuration, the number sleeve 60 can rotate freely in the decrementing direction relative to the housing 10 and/or locking member 160 under the influence of the torque exerted by drive spring 90. Via the open end 675, the locking member 160 may also re-enter the guide track in order to switch the mechanism from the driving configuration into the decrementing configuration.

At least one of the locked sections, preferably all of the locked sections, do have another open axial end 676, particularly a proximal open end. Via the proximal open end, the locking member 160 may be inserted into the guide track.

The clutch member 170 comprises one or a plurality of slots 171, e.g. two oppositely disposed slots. The slots are arranged to receive locking member 160 such that the locking member 160 can extend from the interior of the clutch member 170 to the exterior of the clutch member. Specifically, the locking member may extend through the entire clutch member 170, e.g. by protruding through both slots. The slots 171 are expediently oppositely disposed. In the exemplary embodiment, the slots extend in the axial direction such that the locking member 160 can travel axially within the slots 171. The slots 171 are axially oriented, preferably only axially.

The clutch member 170 comprises one or a plurality of unidirectional interface features 172. These features do cooperate with ratchet teeth 101 which are provided in the housing. Ratchet teeth 101 define the unit increment. The features 172 are configured in the same way as features 164 of the locking member 160 in the previously described embodiment, particularly as radially extending elastically deflectable ratchet arms. In this way, a unidirectional ratchet interface is provided, which, when the interface is established, enables relative rotation of the clutch member 170 with respect to the housing 10 in the incrementing direction only. As compared to the slots 171, the unidirectional interface features 172 are arranged more proximally on the clutch member 170. In the same way as discussed above with respect to the features 164, the unidirectional ratchet interface could also be realized by providing the teeth on the clutch member and the interface features on the body or housing 10. Furthermore, the clutch member 170 comprises a receive region 173, which is designed and arranged to be received in the drive sleeve 40 when the parts are assembled. The receive region 173 is expediently arranged distally offset from the slots 171.

The button 70, in particular the support 72 is provided with one or a plurality of slots 704. Slots 704 are expediently oppositely disposed. Slots 704 do extend helically. Slots 704 extend in the same sense of rotation. The slots 704 are expediently designed to receive the locking member 160 such that the locking member 160 can protrude from the support 72 through the respective slot, particularly on opposite sides. The support 72 is expediently received within the clutch member 170 when the parts are assembled. Then, the locking member 160 extends through the clutch member 170 through slots 171 which are axially oriented and through slots 704 in the support 72 which are helically oriented. Consequently, if the button 70 is rotated relative to clutch 170 this results in an axial displacement of the locking member 160. This axial displacement can be used to displace the locking member 160 out of the locked section 671 and enable cooperation of locking member 160 and unlocked section 672. In the first angular position of the button which is suitable for incrementing a dose, the locking member 160 expediently cooperates with the distal end of the helical slot 704 such that rotation of the button 70 in the incrementing direction does not result in relative axial displacement between locking member 160 and clutch member 170. Rotation in the decrementing direction between clutch member 170 and button 70 does result in relative axial displacement between locking member 160 and clutch member 170. It is readily apparent for a skilled person that, instead of using the helical slot on the button 70 and the axial slot on the clutch member 170 the helical slot could be provided on the clutch member and the axial slot on the button with similar functionality.

Figure 21:
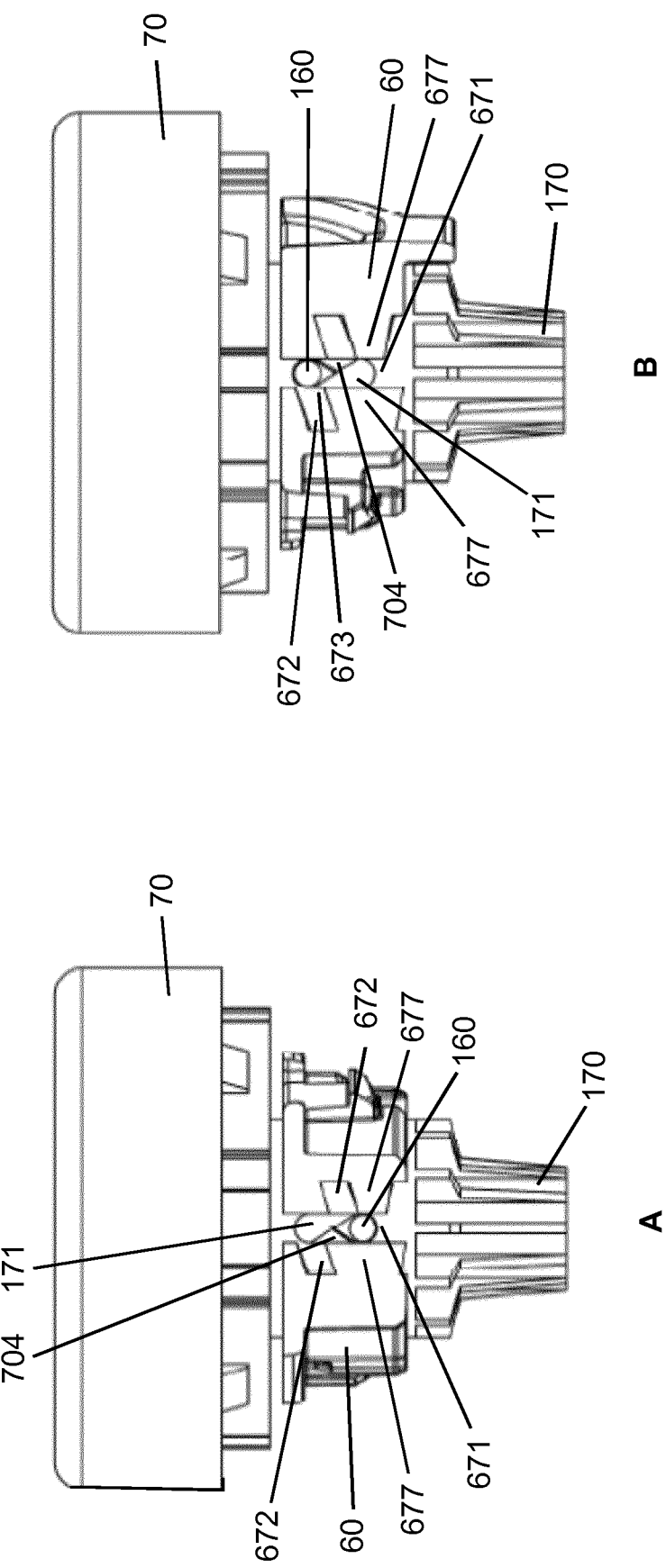
FIG. 21 shows components of the incrementing and decrementing mechanism according to this embodiment in different situations in representations A and B.

In the following, the operation for incrementing and decrementing the mechanism and also the driving operation are described in conjunction with FIG. 21 which shows two different situations of the mechanism in FIGS. 21A and 21B which show partially sectional side views of components of the mechanism in an assembled state.

When the device is ready for setting a dose, that is to say it is at a zero dose position, or a dose has already been set and should be dispensed or decremented, then mechanism is in a situation as illustrated in FIG. 21A. Particularly, the locking member 160 is arranged within a locked section 671 of the guide track 67. The locking member 160 is expediently in the distal end position relative to the slots 704 and/or 171 in the button or the clutch member 170 respectively. When the dose should be incremented, the button is rotated in the incrementing direction, which is, for example, the clockwise direction and/or to the left in FIG. 21A.

As the locking member 160 abuts a profiled surface of the track 67 in the locked section 671, and also because relative rotation between clutch member 170 and button 70 is not permitted on account of the locking member being prevented from moving distally, rotation of the button 70 is transferred to the number sleeve 60 via the locking member 160. Thus, the number sleeve is incremented by the desired number of unit increments. The increasing load in the drive spring 90 is reacted by the unidirectional interface formed between features 172 and ratchet teeth 101.

When, starting from the situation in FIG. 21A, the button 70 is rotated in the decrementing direction, e.g. to the right, the button 70 rotates, particularly by a limited amount, relative to the clutch member 170 which results in an axial displacement of the locking member 160. The axial displacement is achieved as the locking member is axially guided by slot 171 and helically guided by slot 704. Thus, when the button is rotated in the decrementing direction, the locking member 160 is displaced in the proximal direction relative to the number sleeve 60. This achieves that the locking member is now axially aligned with the start of the unlocked section 672 of the guide tracks 67 as depicted in FIG. 21B. Particularly locking member 160 is arranged in the transition region 673 of the guide track. When the locking member 160 has arrived in this axial position, the number sleeve 60 can rotate in the decrementing direction relative to the housing 10. Thus, once the locking member 160 is in this position, the drive spring 90 can rotate the number sleeve 60 into the decrementing direction. If the user then is still connected to the button 70, load of the drive spring is transferred to the user which suggests to the user that he has successfully triggered decrementing of the dose. The number sleeve 60 now rotates relative to the clutch member 170 and also relative to the locking member 160. Thereby, on account of the helical configuration of the unlocked section which is guided along the locking member 160, the locking member 160 is displaced back towards its axial starting position, particularly in the distal direction until it cooperates with the subsequent locking section. Consequently, the torque exerted by the drive spring is used to move the locking member axially back into the locked position, i.e. the position in which the locking member 160 is arranged within a locked section of the guide track 67. The axial displacement of the locking member 160 also returns the button 70 back to the angular start position due to the helical coupling between button and locking member. Thus, the mechanism is automatically switched back to the situation depicted in FIG. 21A.

The number of units by which the dose can be decremented is determined by the angular extension of the unlocked section. Preferably, the angular extension of the unlocked section 672 is greater than or equal to the angular extension or angle corresponding to one unit increment, preferably greater than the angular extension or angle corresponding to five unit increments.

When, after a dose has been set, from the situation depicted in FIG. 21A, the button 70 is depressed in the distal direction, the locking member 160 is disengaged from the guide track 67 as the locked section 671 is open at the distal end via which the locking member 160 leaves the guide track. The button is rotationally locked by features 703 which cooperate with teeth 101 relative to the housing 10. When the button 70 is displaced distally the releasable locking interface formed by means of the locking member 160 is released by this axial movement of the button. This allows the number sleeve 60 to rotate freely in the decrementing direction or driving direction in order to drive rotational movement of the drive sleeve 40 which is rotationally locked to the number sleeve in the driving configuration as explained previously already in conjunction with other embodiments. The drive sleeve 40 is not coupled rotationally to the clutch member 170 and may rotate freely relative to the clutch member 170. In this way, the dose which was previously set can be administered. When the pressure on the button 70 is released, the clutch spring 140 moves the drive sleeve and, together with it, the clutch member 170 in the proximal direction and the locking member 160 re-enters the guide track 67 through the distal end of one of the locked sections 671. Then, after delivery, the mechanism is again in the situation depicted in FIG. 21A. In case, the locking member is not angularly aligned with an open end, via which it can re-enter the guide track 67, after the delivery operation has been completed, the user may rotate the button 70 in the incrementing direction relative to the number sleeve 60 until the locking member 160 is aligned with an open end of the guide track 67 and re-engages the guide track. Then, the user may have a visual confirmation that the device is, again, in the decrementing configuration when the dose indicated on the number sleeve is incremented again.

In slightly different words, this embodiment uses a radial ratchet to enable active increment of unit dose adjustment on a cartridge based, torsionally driven pen injector in conjunction with a mechanism for releasing a rotational lock between two components to allow controlled decrement of the selected dose under the internal torsional load. Dose increment is achieved by the user applying torsion to an external dose dialling component (button 70) which is free to move in the increment angular direction. Rotation of this dialling component increments the dialled dose by unit increments. Dose decrement is achieved by the user applying torsion to the dialling component. This component rotates through a limited angle in the decrement direction. A pin (locking member) located in helical slots in the dialling component is moved in a direction parallel to the pen injector axis by the rotation in the decrement direction. The pin is also engaged in the radial ratchet component and in a profiled track in a component resolving the internal torsional load. The axial movement of the pin moves it from a region of the profiled track where the internal torsional load is held, to one where it is released allowing limited rotation and hence limited reduction in set dose. The decrement mechanism is separate from and independent of the increment mechanism. This enables fine tuning of the increment mechanism features to meet the user force/displacement requirements without affecting the decrement process. As the increment mechanism is not required to release in the decrement direction this allows optimisation of the ratchet elements to ensure that the ratchet does not slip under the torsional load applied to the clutch component.

The independent asymmetric mechanism allows a unique, independent tuning of the forces required to both increment and decrement the dose. This is of particular benefit as the torsional drive load encountered by the ratchet and locking elements can vary with both angular direction and dose size. By tuning both the increment and decrement independently the user experience can be adjusted to an acceptable, optimized feel and sound (within the working range), whilst minimizing the risk of the slippage due to constant application of the drive torque. The advantage over what is currently in the field is that this embodiment offers more design freedom to be tuned to precisely meet the user needs and the essential engineering requirement for no slippage (which can affect dose accuracy). It may also be adaptable to change to different dose increments. An advantage of the decrement mechanism is that it reduces the set dose by a fixed number of units, the number being determined by the design of the profiled track. An additional advantage of the decrement mechanism is that as the mechanism releases the fixed number of units the pin is translated by the track profile causing small movement of the dialing component providing tactile/haptic feedback to the user.

This embodiment relates to two separate mechanisms which in conjunction control the incrementing and decrementing of the dose. Ideally the mechanism is symmetric in torsional force and increment size to promote logical usability cues, however. The basis of the embodiment is a radial ratchet and an additional rotational locking system. The radial ratchet allows rotation in the dose increment direction. Disengagement of the locking system allows controlled dose decrement under the torsional drive spring load. This embodiment utilizes a profiled track in a component that is rigidly coupled to the rotating end of the torsional drive spring. This may be implemented by rigidly attaching a track component to the number sleeve component that is coupled to the rotating end of the torsional drive spring, or by integrating the profiled track directly into this component. The profiled track consists of "locking" regions parallel to the axis of the device and "decrementing" regions that are helical in nature.

In a similar way as in the previously described embodiment which utilizes the locking member 160 with the locking features 161, instead of using an element which is permanently static for the unidirectional rotational interface, also the drive sleeve 40 can be utilized for this purpose.

Figure 22:
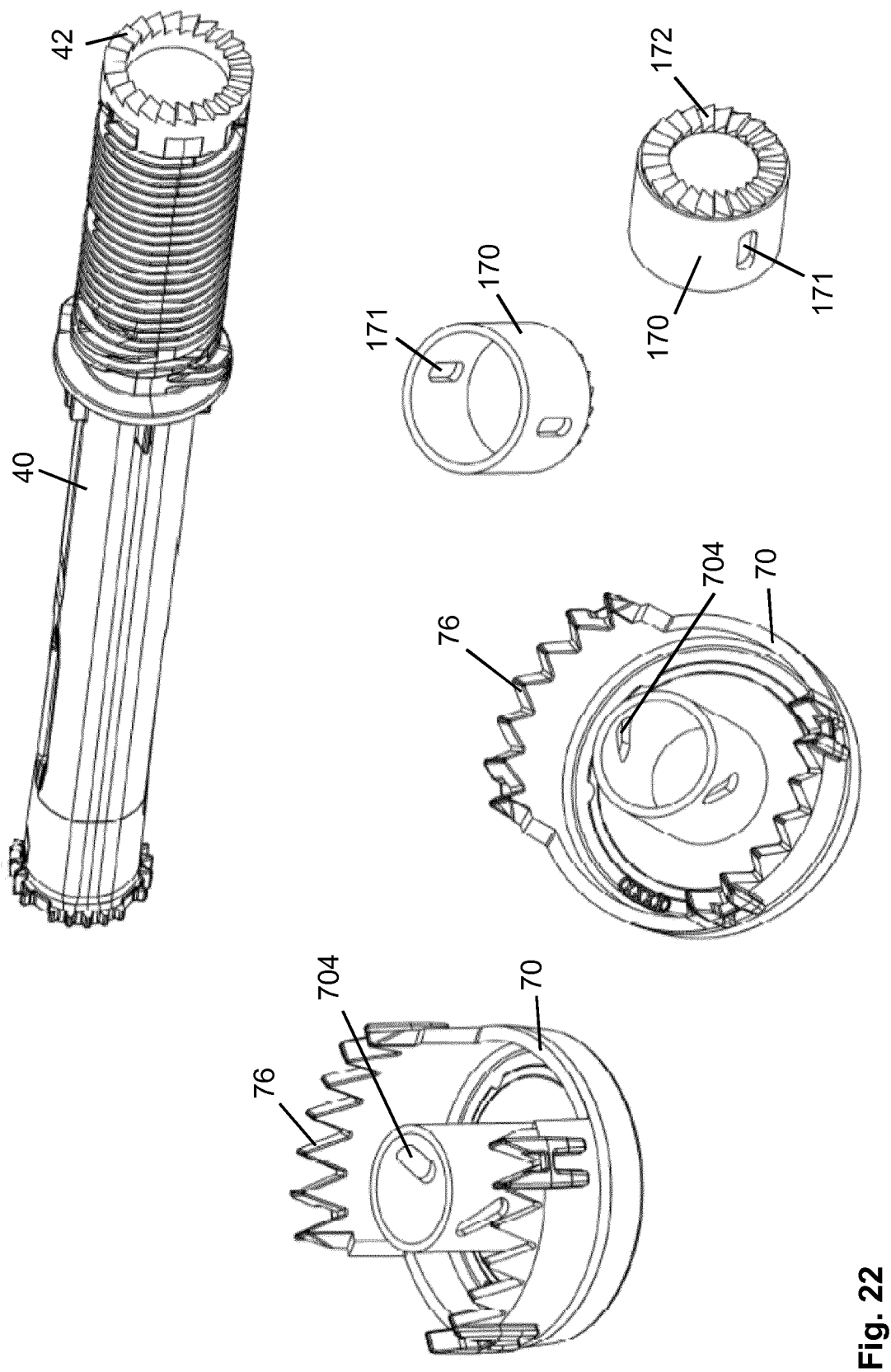
FIG. 22 shows components of an incrementing and decrementing mechanism which were modified as compared to the previous embodiment in order to provide a modified embodiment of the incrementing and decrementing mechanism in different views.

Components of the device which are modified for this embodiment are shown in FIG. 22. Specifically, teeth 703 in the button are replaced with teeth 76 which achieve a splined engagement relative to the housing in the driving configuration. In a similar way as described previously, the unidirectional rotational coupling is achieved between the drive sleeve 40 and the clutch member 170. For this purpose the unidirectional rotational interface features 172 are provided as axially oriented teeth which extend in the axial direction and mesh with ratchet features 42 provided on the drive sleeve in order to establish the unidirectional rotational coupling, which permits rotation of the clutch member 170 relative to the drive sleeve 40 in the incrementing direction only. Of course, it is also possible, instead of using axially extending teeth to establish the unidirectional coupling, to apply a radial ratchet for the unidirectional interface.

In the driving configuration, the drive sleeve 40 rotates in the driving or incrementing direction relative to the clutch member 170 such that the teeth providing the unidirectional rotational interface ride along each other which does create an audible and/or tactile feedback as explained already previously with respect to FIG. 18, which as far as the modifications are concerned is similar to the present embodiment.

Aside from the modifications illustrated in the FIG. 22 and explained above, the mechanism of this embodiment functions as explained in conjunction with the previous embodiment.

The scope of protection is not limited to the examples given herein above. The disclosure is embodied in each novel characteristic and each combination of characteristics, which particularly includes every combination of any features which are stated in the claims, even if this feature or this combination of features is not explicitly stated in the claims or in the examples.

REFERENCE NUMERALS 10 housing
11a, b window
12 insert
13 sidewall
14 tube
15 arm
16 bottom wall
17 thread
18 spline teeth
19 ring-shaped second part
19a spline teeth
19b arm (spline)
19c arm (snap clip)
19d opening
101 ratchet teeth
20 cartridge holder
30 piston rod (lead screw)
40 drive sleeve
41 spline teeth
42 ratchet feature
43 side face
44 side face
45 spline feature
46 locking feature
461 surface
47 drive sleeve body
48 holding space
49 protrusion
50 nut
60 dose indicator/number sleeve
60a number sleeve lower
60b number sleeve upper
61 spline feature
62 locking feature
63 flexible arm
64 number sleeve body
65 feature
651 surface
652 surface
66 block feature
67 guide track
671 locked section
672 unlocked section
673 transition region
674 transition region
675 end
676 end
677 block feature
70 button
71 release feature
72 support
73 region
74 region
75 step
76 spline feature
77 feature
78 receiving section
79 support feature
701 feature
702 interface feature
703 teeth
704 slot
80 dose selector
90 torsion spring
91 hook
100 cartridge
110 gauge element
120 clutch plate
130 clutch spring
140 bearing
150 support member
151 support region
152 support feature
153 section
154 coupler region
155 coupler feature
160 locking member
161 locking feature
162 locking member body
163 flexible arm
164 unidirectional interface feature
165 region
166 button interface feature
167 drive feature
170 clutch member 171 slot
172 unidirectional interface feature
173 receive region
I axis
C clearance

The invention claimed is:

1. A drug delivery device for delivering a number of pre-settable doses of a liquid drug formulation out of an undivided reservoir, the drug delivery device comprising:
a housing,
a movable member arranged to be rotatable in an incrementing direction and a decrementing direction with respect to the housing, the incrementing direction being opposite the decrementing direction, the movable member being operatively coupled to an energy storage member and biased to rotate into the decrementing direction by energy stored in the energy storage member, wherein rotation of the movable member in the incrementing direction increases the energy stored in the energy storage member,
a locking system comprising a locking feature, a block feature, and a release member,
wherein the locking feature is arranged to cooperate with the block feature to form a releasable locking interface, the releasable locking interface being configured such that, when the releasable locking interface is established, a rotational movement of the movable member relative to the housing is blocked in the decrementing direction, and when the releasable locking interface is released, the movable member is rotatable in the decrementing direction,
wherein the release member is rotatable relative to the housing and/or the locking feature between a first angular position and a second angular position, wherein, in the first angular position, the releasable locking interface is established, and, in the second angular position, the releasable locking interface is released at least temporarily,
wherein the drug delivery device is configured such that the rotation of the release member from the first angular position to the second angular position causes the release of the releasable locking interface,
wherein, when the release member is in the first angular position, the drug delivery device is switchable between a decrementing configuration and a driving configuration, the decrementing configuration and the driving configuration being two different axial configurations,
wherein in the decrementing configuration, the releasable locking interface is established, and in the driving configuration, the releasable locking interface is released, and
wherein, the locking feature and the block feature are axially displaceable relative to one another for switching between the driving configuration and the decrementing configuration.

2. The drug delivery device of claim 1, wherein the movable member is rotatable in the incrementing direction relative to the housing by multiples of a unit increment,
wherein the drug delivery device comprises at least one unidirectional interface which defines the unit increment and when the release member is in the first angular position, the at least one unidirectional interface permits rotation of the movable member relative to the housing in the incrementing direction only, wherein (i) the at least one unidirectional interface is the releasable locking interface, or (ii) the at least one unidirectional interface is different from the releasable locking interface.

3. The drug delivery device of claim 1, wherein the releasable locking interface blocks relative rotational movement between the locking feature and the block feature in both rotational directions.

4. The drug delivery device of claim 1, wherein the locking feature mechanically cooperates with the release member to releasably lock the release member in the second angular position.

5. The drug delivery device of claim 1, wherein the drug delivery device comprises a driven member which is rotationally locked relative to the housing in the decrementing configuration and rotatable relative to the housing in the driving configuration, wherein in the driving configuration the driven member is rotationally locked to the movable member, and/or wherein the locking feature is part of, firmly connected to, or formed by a locking member and the block feature is part of or firmly connected to a block member.

6. The drug delivery device of claim 5, wherein the locking member comprises a plurality of resilient locking features which are circumferentially and uniformly disposed on the locking member, wherein the plurality of resilient locking features are oriented in an axial direction, and wherein each resilient locking feature is flexible or mounted flexibly in such a manner that it can be radially deflected but react a rotational, angular or tangential load or force, and wherein the block feature is arranged to contact an angular face of one of the resilient locking features.

7. The drug delivery device of claim 5, wherein the locking member comprises, in addition to the locking feature, a unidirectional interface feature for establishing a unidirectional interface which defines a unit increment.

8. The drug delivery device of claim 7, wherein the locking feature is radially displaceable relative to the unidirectional interface feature.

9. The drug delivery device of claim 5, wherein the locking feature is resiliently displaceable in a radial direction, and wherein the block member has comprises the block feature, the block feature being a plurality of block features, which extend in the radial direction and are uniformly distributed in an angular direction, wherein the plurality of block features are designed to cooperate with the locking feature to form a unidirectional radial ratchet interface as the releasable locking interface which permits rotation of the movable member relative to the block member in the incrementing direction but blocks rotation of the movable member relative to the block member and/or the housing in the decrementing direction.

10. The drug delivery device of claim 9, wherein the release member comprises a plurality of radially extending member features which are circumferentially disposed on the release member, wherein the plurality of radially extending member features protrude radially with respect to the plurality of block features, and wherein the drug delivery device is configured such that, when the release member is rotated relative to the block member, the movable member, the housing and/or the locking feature towards the second angular position, the locking feature is displaced radially on account of its operative coupling with a member feature of the plurality of radially extending member features, until the releasable locking interface is released, thereby allowing rotation of the movable member relative to the housing and/or the block member in the decrementing direction.

11. The drug delivery device of claim 9, wherein, when the release member is in the first angular position, the locking feature is arranged in a first pocket defined between two block features and, simultaneously, in a second pocket defined between two member features, and wherein, when the release member is rotated towards the second angular position, the locking feature is radially displaced out of the first pocket but remains in the second pocket, and wherein the release member and the block member are axially displaceable relative to the locking feature in order to switch into the driving configuration of the drug delivery device.

12. The drug delivery device of claim 1, wherein the drug delivery device comprises a support feature which is rotatable relative to the locking feature between a first position and a second position such that it radially supports the locking feature in the first position but allows radial movement of the locking feature relative to the block feature in a second position, wherein the drug delivery device is configured such that (i) the support feature is in the first position when the release member is in the first angular position, such that the support feature stabilizes the locking feature against radial displacement on account of a torque transferred from the energy storage member via the block feature to the locking feature, and (ii) the support feature is in the second position when the release member is in the second angular position, such that the locking feature is radially displaced relative to the block feature on account of the torque.

13. The drug delivery device of claim 12, wherein the drug delivery device comprises a support member which comprises the support feature, the support member being rotatable relative to a locking member wherein the block feature is arranged to contact an angular face of the locking feature such that the locking feature is supported radially by the support feature to form the releasable locking interface.

14. The drug delivery device of claim 13, wherein the support member is coupled with the release member via a coupling to follow rotation of the release member in both rotational directions wherein the coupling is configured to have a rotational clearance such that the release member is rotatable relative to the support member before the support member follows rotation of the release member, and wherein, when the release member is rotated in the decrementing direction from the first angular position towards the second angular position, the support member rotates in the same direction, thereby removing support from the locking feature, such that rotation of the movable member in the decrementing direction is allowed, thereby displacing the locking feature radially.

15. The drug delivery device of claim 1, wherein the locking feature is axially displaceable from a locked position to an unlocked position relative to a block member for releasing the releasable locking interface.

16. The drug delivery device of claim 15, wherein the block member comprises a guide track which is provided to interact with the locking feature, the guide track comprising at least two different types of sections, a locked section, which is defined by one or more block features, and an unlocked section, the locked section extending axially and the unlocked section extending helically, where, as seen along the guide track, the locked section and the unlocked section are alternatingly disposed and the guide track comprises one or more locked sections and one or more unlocked sections, and wherein the drug delivery device is configured such that, when the release member is in the first angular position, the locking feature is in the locked position and interacts with the locked section of the guide track and, when the release member is rotated towards the second angular position, the locking feature is displaced axially towards and into the unlocked position where it can cooperate with the unlocked section.

17. The drug delivery device of claim 15, wherein the locking feature is operatively connected to the release member via at least a helical interface and an axial interface, where the helical and axial interfaces are established simultaneously.

18. The drug delivery device of claim 1, wherein the block feature is part of or firmly connected to a block member, wherein the locking feature is axially displaceable from a locked position to an unlocked position relative to the block member for releasing the releasable locking interface, and wherein the locking feature is operatively coupled to the release member, such that the rotational movement of the release member from the first angular position towards the second angular position is converted into axial movement of the locking feature from the locked position towards the unlocked position.

19. A drug delivery device for delivering a number of pre-settable doses of a liquid drug formulation out of an undivided reservoir, the drug delivery device comprising:

a housing, a movable member arranged to be rotatable in an incrementing direction and a decrementing direction with respect to the housing, the incrementing direction being opposite the decrementing direction, the movable member being operatively coupled to an energy storage member and biased to rotate into the decrementing direction by energy stored in the energy storage member, wherein rotation of the movable member in the incrementing direction increases the energy stored in the energy storage member, a locking system comprising a locking feature, a block feature, and a release member, wherein the locking feature is arranged to cooperate with the block feature to form a releasable locking interface, the releasable locking interface being configured such that, when the releasable locking interface is established, a rotational movement of the movable member relative to the housing is blocked in the decrementing direction, and when the releasable locking interface is released, the movable member is rotatable in the decrementing direction, wherein the release member is rotatable relative to the housing and/or the locking feature between a first angular position and a second angular position, wherein, in the first angular position, the releasable locking interface is established, and, in the second angular position, the releasable locking interface is released at least temporarily, wherein the drug delivery device is configured such that the rotation of the release member from the first angular position to the second angular position causes the release of the releasable locking interface, wherein the drug delivery device further comprises a support feature which is rotatable relative to the locking feature between a first position and a second position such that the support feature radially and/or axially supports the locking feature in the first position but allows radial and/or axial movement of the locking feature relative to the block feature in the second position, wherein the drug delivery device is configured such that the support feature is in the first position when the release member is in the first angular position, and the support feature is in the second position when the release member is in the second angular position, wherein the movable member is rotatable in the incrementing direction relative to the housing only by multiples of a unit increment, wherein the drug delivery device comprises at least one unidirectional interface which defines the unit increment and, when the release member is in the first angular position, permits rotation of the movable member relative to the housing in the incrementing direction only, wherein the at least one unidirectional interface is different from the releasable locking interface.

20. A drug delivery device for delivering a number of pre-settable doses of a liquid drug formulation out of an undivided reservoir, the drug delivery device comprising:
a housing,
a movable member arranged to be rotatable in an incrementing direction and a decrementing direction with respect to the housing, the incrementing direction being opposite the decrementing direction, the movable member being operatively coupled to an energy storage member and biased to rotate into the decrementing direction by energy stored in the energy storage member, wherein rotation of the movable member in the incrementing direction increases the energy stored in the energy storage member,
a locking system comprising a locking feature, a block feature, and a release member,
wherein the locking feature is arranged to cooperate with the block feature to form a releasable locking interface, the releasable locking interface being configured such that, when the releasable locking interface is established, a rotational movement of the movable member relative to the housing is blocked in the decrementing direction, and when the releasable locking interface is released, the movable member is rotatable in the decrementing direction,
wherein the release member is rotatable relative to the housing and/or the locking feature between a first angular position and a second angular position,
wherein a locking member comprises a plurality of locking features,
wherein each of the plurality of locking features is flexible or mounted flexibly such that each of the plurality of locking features can be radially and/or axially deflected in an elastic way in order to release the releasable locking interface but react a rotational, angular or tangential force,
wherein in the first angular position, the block feature is arranged to contact an angular face of one of the plurality of locking features, wherein the one of the plurality of locking features is supported by a support feature against deflection in the first angular position, and
wherein when the release member is rotated towards the second angular position, the support feature is arranged and configured to rotate relative to the one of the plurality of locking features such that support is removed from the one of the plurality of locking features and the one of the plurality of locking features can deflect to release the release the releasable locking interface.

* * * * *

UNITED STATES PATENT AND TRADEMARK OFFICE
CERTIFICATE OF CORRECTION

PATENT NO. : 11,524,116 B2  
APPLICATION NO. : 16/619629  
DATED : December 13, 2022  
INVENTOR(S) : Joshua Bough and Rosemary Burnell Page 1 of 1

It is certified that error appears in the above-identified patent and that said Letters Patent is hereby corrected as shown below:

In the Claims

Column 66, Line 30, Claim 20, delete "release the release the" and insert -- release the --

Signed and Sealed this  
Twenty-fourth Day of January, 2023

Katherine Kelly Vidal  
*Director of the United States Patent and Trademark Office*